US006846834B2

(12) United States Patent
Browner et al.

(10) Patent No.: US 6,846,834 B2
(45) Date of Patent: Jan. 25, 2005

(54) ANTIINFLAMMATION AGENTS

(75) Inventors: Michelle F. Browner, San Francisco, CA (US); David L. Clark, Albany, CA (US); Timothy D. Cushing, Pacifica, CA (US); Xiaolin Hao, So. San Francisco, CA (US); Ronald C. Hawley, Mountain View, CA (US); Xiao He, Foster City, CA (US); Juan C. Jaen, Burlingame, CA (US); Sharada S. Labadie, Sunnyvale, CA (US); Marie-Louise Smith, Half Moon Bay, CA (US); Francisco X. Talamas, Mountain View, CA (US); Nigel P. C. Walker, Burlingame, CA (US); Marc Labelle, Burlingame, CA (US)

(73) Assignees: Amgen Inc., So. San Francisco, CA (US); Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/004,287

(22) Filed: Oct. 23, 2001

(65) Prior Publication Data
US 2002/0161004 A1 Oct. 31, 2002

Related U.S. Application Data
(60) Provisional application No. 60/243,581, filed on Oct. 26, 2000.

(51) Int. Cl.$^7$ .................... C07C 281/08; C07D 215/02; C07D 471/04; A61K 31/175; A81P 19/02
(52) U.S. Cl. .................. 514/307; 514/314; 514/259.14; 546/122; 546/139; 546/152; 546/167; 544/279
(58) Field of Search ................. 546/122, 139, 546/152, 167; 544/279; 514/307, 314, 259.41

(56) References Cited

U.S. PATENT DOCUMENTS

| 6,207,679 B1 | 3/2001 | Cuny et al. |
| 6,258,822 B1 | 7/2001 | Geyer et al. |

FOREIGN PATENT DOCUMENTS

| WO | WO-98/47869 A1 | * 10/1998 |
| WO | WO 01/00610 A1 | 1/2001 |
| WO | WO 01/30774 A1 | 5/2001 |
| WO | WO 01/58890 A1 | 8/2001 |
| WO | WO 01/68648 A1 | 9/2001 |
| WO | WO 02/24679 A1 | 3/2002 |
| WO | WO 02/28860 A2 | 4/2002 |
| WO | WO 02/30353 A2 | 4/2002 |
| WO | WO 02/30423 A1 | 4/2002 |
| WO | WO 02/41843 A2 | 5/2002 |
| WO | WO 02/44153 A1 | 6/2002 |
| WO | WO 02/46171 A2 | 6/2002 |
| WO | WO 02/060386 A2 | 8/2002 |
| WO | WO 02/076985 A1 | 10/2003 |

OTHER PUBLICATIONS

Cecil Textbook of Medicine, edited by Bennet, J.C., and Plum F., 20th edition,vol. 1, 1004–1010, 1996.*
Graninger et al. Curr. Opin. Rhematol. 13(3) 209–13, 2001.*
Shaw et al. Expert Opin. Investig. Drugs 9(7) 1469–1478, 2000.*
Karin, M., 1999, "The Beginning of the End: IκB Kinase (IKK) and NF–κB Activation," *The Journal of Biological Chemistry* 274(39):27339–27342.
Karin, M., 1999, "How NF–κB is activated: the role of the IκB kinase (IKK) complex," *Oncogene* 18:6867–6874.
Karin and Delhase, 2000. "The IκB Kinase (IKK) and NF–κB: key elements in proinflammatory signaling," *Seminars in Immunology* 12(1):85–98 (Abstract).
May et al., 2000, "Selective Inhibition of NF–κB activation by a peptide that blocks the interaction of NEMO with the IκB kinase complex," *Science* 289:1550–1554.
Rossi et al., 2000, "Anti–inflammatory cyclopentenone prostaglandins are direct inhibitors of IκB kinase," *Nature* 403:103–108.
Woronicz et al., 1997, "IκB Kinase–β: NF–κB Activation and Complex Formation with IκB Kinase–α and NIK," *Science* 278:866–870.

* cited by examiner

Primary Examiner—Richard L. Raymond
Assistant Examiner—Venkataraman Balasubramanian
(74) Attorney, Agent, or Firm—Townsend and Townsend and Crew LLP

(57) ABSTRACT

Compounds, compositions and methods that are useful in the treatment of inflammatory, immunoregulatory, metabolic and cell proliferative conditions or diseases are provided herein. In particular, the invention provides compounds which modulate the expression and/or function of proteins involved in inflammation, metabolism and cell proliferation. The subject compounds contain fused carbocyclic or heterocyclic rings.

73 Claims, No Drawings

ět

ANTIINFLAMMATION AGENTS

This application claims the benefit of U.S. Ser. No. 60/243,581 filed Oct. 26, 2000 which is incorporated by reference in its entirety

BACKGROUND OF THE INVENTION

Tumor Necrosis Factor (TNF) and interleukin-1 (IL-1) are cytokines that have been implicated in a wide range of biological processes, including inflammation. The recruitment of immune cells to sites of injury involves the concerted interactions of a large number of soluble mediators. Several cytokines appear to play key roles in these processes, particularly IL-1 and TNF. Both cytokines are derived from mononuclear cells and macrophages, along with other cell types. Physiologically, they produce many of the same proinflammatory responses, including fever, sleep and anorexia, mobilization and activation of polymorphonuclear leukocytes, induction of cyclooxygenase and lipoxygenase enzymes, increase in adhesion molecule expression, activation of B-cells, T-cells and natural killer cells, and stimulation of production of other cytokines. Other actions include a contribution to the tissue degeneration seen in chronic inflammatory conditions, such as stimulation of fibroblast proliferation, induction of collagenase, etc. They have also been implicated in the process of bone resorption and adipose tissue regulation. Thus, these cytokines play key roles in a large number of pathological conditions, including rheumatoid arthritis, inflammatory bowel disease, diabetes, obesity, bone mass loss, cancer, neurological conditions such as ischemic stroke or closed head injuries, etc.

Cytokines trigger a variety of changes in gene expression in their target cells by binding and activating their respective cognate receptors. Receptor activation sets in motion certain biochemical events, including the activation of otherwise latent transcription factors. Members of the NF-κB Rel family of transcription factors represent some of the most prominent of these transcription factors, having been implicated in the regulation of genes involved in inflammation, cell proliferation, apoptosis, and several other basic cellular functions (Verma et al. *Genes Dev.* 9, 2723 (1995); Baichwal & Baeuerle, *Curr. Biol.* 7, 94 (1997)).

The best studied member of this family of transcription factors is NF-κB, which generally exists in cells as a heterodimer of two proteins: p50 (NF-κB1) and p65 (RelA), although homodimers of these individual components are also possible (Baeuerle and Baltimore, *Cell*, 53, 211 (1988); Baeuerle and Henkel, *Annu. Rev. Immunol.* 12, 141 (1994)). NF-κB, in its inactive form, resides in the cytoplasm of cells. In response to various types of stimuli, such as proinflammatory cytokines (e.g. TNF and IL-1), ultraviolet irradiation and viral infection (Verma, 1995; Baichwal, 1997; Cao et al. *Science,* 271, 1128 (1996)) NF-κB migrates to the nucleus. TNF and IL-1 have been shown to be two key proinflammation agents in a wide variety of pathological conditions, including rheumatoid arthritis, septic shock, inflammatory bowel disease, dermal sensitization disorders, neurological trauma such as stroke or closed-head injuries, etc.

In its inactive state, the NF-κB heterodimer is held in the cytoplasm by association with inhibitory IkB proteins. Recently, the three-dimensional structure of a NF-κB/IκB ternary complex has been solved (Huxford et al. *Cell*, 95, 759 (1998); Jacobs et al. *Cell*, 95, 749 (1998)). When cells are treated with the appropriate stimuli, such as IL-1 or TNF, intracellular signal transduction pathways are activated that lead to the eventual phosphorylation of IkB proteins on two specific residues (serines 32 and 36 in IkBα, serines 19 and 23 in IkBβ). Mutation of one or both serine residues renders IkB resistant to cytokine-induced phosphorylation. This signal-induced phosphorylation targets IkB for ubiquitination and proteosome-mediated degradation, allowing nuclear translocation of NF-κB (Thanos and Maniatis, *Cell*, 80, 529 (1995)). The only regulated step in the IkB degradation pathway is the phosphorylation of IkB by IkB kinases (IKK) (Yaron et al. *EMBO J.* 16, 6486 (1997)).

Several intermediate steps in the TNF- and IL-1-activated signaling pathways that result in IkB phosphorylation have been elucidated in recent years. Both pathways appear to merge at the level of the protein kinase NIK (NF-κB-inducing kinase) (Malinin et al. *Nature*, 385, 540 (1997); Song et al. *Proc. Natl. Acad. Sci. USA*, 94, 9792 (1997)). Similarly, the protein kinases MEKK1 and MLK3 have been implicated in the induction of IKK activity (Lee et al. *Proc. Natl. Acad. Sci. USA*. 95, 9319 (1998); Hehner et al. *Mol. Cell. Biol.* 20, 2556 (2000)). While the specific details remain somewhat unclear regarding how these or other intermediate proteins may interact with and/or stimulate IKK activity in cells, significant progress has been made in elucidating the enzymes responsible for IkB phosphorylation. Two IKK enzymes, generally referred to as IKKα and IKKβ (Woronicz et al. *Science*, 278, 866 (1997); Zandl et al. *Cell*, 91, 243 (1997)) or IKK-1 and IKK-2 (Mercurio et al. *Science*, 278, 860 (1997)) have been discovered. Both forms of IKK can exist as homodimers and as IKKα/IKKβ heterodimers. Another recently discovered component of the IkB kinase complex is a regulatory protein, known as IKK-gamma or NEMO (NF-κB-Essential Modulator) (Rothwarf et al. *Nature*, 395, 297 (1998)). NEMO does not contain a catalytic domain, and thus it appears to have no direct kinase activity and it probably serves a regulatory function. Existing data suggest that the predominant form of IKK in cells is an IKKα/IKKβ heterodimer associated with either a dimer or a trimer of NEMO (Rothwarf et al. *Nature* 395, 297 (1998)).

Biochemical and molecular biology experiments have clearly identified IKKα and IKKβ as the most likely mediators of TNF- and IL-1-induced IkB phosphorylation and degradation, which results in NF-κB activation and upregulation of families of genes involved in inflammatory processes (Woronicz et al. *Science* (1997); Karin, *Oncogene* 13, 6867 (1999); Karin, *J. Biol. Chem.* 274, 27339 (1999)). IKKα and IKKβ have very similar primary structures, displaying more than 50% overall sequence identity. In the kinase domain, their sequences are 65% identical.

Based on our present understanding of the critical role played by TNF and IL-1 in the wide array of pathological conditions described above, and the involvement of IKKα and IKKβ in the signal transduction of both cytokines, the discovery of compounds that potently and selectively inhibit either of these kinases would result in a major advancement in the therapy of those conditions. In this application we describe a novel type of compounds which displays such desirable activity.

SUMMARY OF THE INVENTION

In one aspect, the present invention provides compounds useful in the treatment of inflammatory, metabolic or malignant conditions, having the formula:

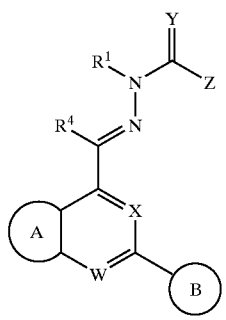

In formula 1, the letters W and X independently represent N or CH; Y represents O, S or N(R), wherein R is H, CN, NO$_2$, (C$_1$–C$_{10}$)alkyl, (C$_3$–C$_{10}$)cycloalkyl, (C$_4$–C$_{10}$) cycloalkyl-alkyl, (C$_3$–C$_{10}$)alkenyl or (C$_2$–C$_{10}$)alkynyl; and Z represents H, (C$_1$–C$_{10}$)alkyl, (C$_3$–C$_{10}$)cycloalkyl, (C$_4$–C$_{10}$)cycloalkyl-alkyl, (C$_2$–C$_{10}$)alkenyl, (C$_2$–C$_{10}$) alkynyl or NR$^2$R$^3$.

The symbols R$^1$, R$^2$ and R$^3$ are independently H, (C$_1$–C$_{10}$)alkyl, (C$_3$–C$_{10}$)alkenyl, (C$_2$–C$_{10}$)alkynyl, (C$_1$–C$_{10}$) heteroalkyl, (C$_3$–C$_{10}$)cycloalkyl, (C$_4$–C$_{10}$)cycloalkyl-alkyl, (C$_4$–C$_{10}$)cycloheteroalkyl-alkyl, (C$_3$–C$_{10}$)cycloheteroalkyl, aryl, aryl(C$_1$–C$_4$)alkyl, aryl(C$_1$–C$_4$)heteroalkyl, heteroaryl (C$_1$–C$_4$)alkyl, heteroaryl(C$_1$–C$_4$)heteroalkyl, or perfluoro (C$_1$–C$_6$)alkyl. Additionally, when Z is NR$^2$R$^3$, R$^2$ and R$^3$ can be combined to form a heterocyclic 5- to 7-membered ring. The symbol R$^4$ represents H, (C$_1$–C$_6$)alkyl, (C$_3$–C$_6$) cycloalkyl, (C$_4$–C$_7$)cycloalkyl-alkyl, (C$_2$–C$_6$)alkenyl or (C$_2$–C$_6$)alkynyl.

In formula I, the letter A represents a substituted or unsubstituted fused carbocyclic or heterocyclic ring system, the A ring system being mono- or bicyclic wherein the mono- or bicyclic rings are five- or six-membered rings that are aromatic or partially or completely saturated. The letter B represents a substituted or unsubstituted five- or six-membered ring which is aromatic or partially or completely saturated, containing at least one nitrogen atom, and from 0 to 3 additional heteroatoms, wherein the B ring substituents are selected from halogen, CF$_3$, CF$_3$O, (C$_1$–C$_6$)alkyl, perfluoro(C$_1$–C$_6$)alkyls(C$_2$–C$_6$)alkenyl, (C$_2$–C$_6$)alkynyl, (C$_1$–C$_6$)heteroalkyl, (C$_1$–C$_6$)alkoxy, (C$_1$–C$_6$)thioalkoxy, amino, (C$_1$–C$_6$)alkylamino, di(C$_1$–C$_6$)alkylamino, (C$_3$–C$_{10}$) cycloalkyl, (C$_4$–C$_{10}$)cycloalkyl-alkyl, (C$_3$–C$_{10}$) cycloheteroalkyl, cyano, nitro, sulfonamido, (C$_1$–C$_6$)acyl, (C$_1$–C$_6$)acylamino, (C$_1$–C$_6$)alkoxycarbonyl, (C$_1$–C$_6$) alkoxycarbonyl(C$_1$–C$_6$)alkyl, carboxamido and (C$_1$–C$_6$) heteroalkoxy.

Unless otherwise indicated, the compounds provided in the above formula are meant to include pharmaceutically acceptable salts and prodrugs thereof.

In another aspect, the present invention provides pharmaceutical compositions comprising one or more compounds of formula I in admixture with a pharmaceutically acceptable carrier or excipient.

In yet another aspect, the present invention provides methods for the treatment of an inflammatory, metabolic or malignant condition, comprising administering to a subject in need of such treatment a compound of formula I.

DETAILED DESCRIPTION OF THE INVENTION

Abbreviations and Definitions

The abbreviations used herein are conventional, unless otherwise defined.

Unless otherwise stated, the following terms used in the specification and claims have the meanings given below:

"Acyl" means the group —C(O)R', where R' is hydrogen, alkyl, cycloalkyl, cycloalkyl-alkyl, aryl, aryl-alkyl, and variations of these groups in which one or more carbon atoms have been replaced with heteroatoms.

"Alkyl" means a linear saturated monovalent hydrocarbon radical or a branched saturated monovalent hydrocarbon radical having the number of carbon atoms indicated in the prefix. For example, (C$_1$–C$_6$)alkyl is meant to include methyl, ethyl, n-propyl, 2-propyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms.

"Perfluoroalkyl" refers to an alkyl group having the indicated number of carbon atoms, in which some of the attached hydrogen atoms have been replaced with fluorine atoms, in a number ranging from 1 to the maximal number of hydrogen atoms on the alkyl group.

"Alkylene" means a linear saturated divalent hydrocarbon radical or a branched saturated divalent hydrocarbon radical having the number of carbon atoms indicated in the prefix. For example, (C$_1$–C$_6$)alkylene is meant to include methylene, ethylene, propylene, 2-methylpropylene, pentylene, and the like.

"Alkenyl" means a linear monovalent hydrocarbon radical or a branched monovalent hydrocarbon radical having the number of carbon atoms indicated in the prefix and containing at least one double bond. For example, (C$_2$–C$_6$) alkenyl is meant to include, ethenyl, propenyl, and the like.

"Alkynyl" means a linear monovalent hydrocarbon radical or a branched monovalent hydrocarbon radical containing at least one triple bond and having the number of carbon atoms indicated in the prefix. For example, (C$_2$–C$_6$)alkynyl is meant to include ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —R$^a$C(O)R$^b$ where R$^a$ is an alkylene group as defined above and R$^b$ is an alkoxy group as defined above, e.g., methoxycarbonylethyl, ethoxycarbonylbutyl, and the like.

"Aryl" means a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$— CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Aralkyl" means a radical —R$^a$R$^b$ where R$^a$ is an alkylene group (having six or fewer main chain carbon atoms)

and $R^b$ is an aryl group as defined herein, e.g., benzyl, phenylethyl, 3-(3-chlorophenyl)-2-methylpentyl, and the like.

"Aralkenyl" means a radical —$R^aR^b$ where $R^a$ is an alkenylene group and $R^b$ is an aryl group as defined herein, e.g., 3-phenyl-2-propenyl, and the like.

"Arylheteroalkyl" means a radical —$R^aR^b$ where $R^a$ is an heteroalkylene group and $R^b$ is an aryl group as defined herein, e.g., 2-hydroxy-2-phenyl-ethyl, 2-hydroxy-1-hydroxymethyl-2-phenyl-ethyl, and the like.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkyl-alkyl" means a radical —$R^aR^b$ where $R^a$ is an alkylene group and $R^b$ is a cycloalkyl group as defined herein, e.g., cyclopropylmethyl, cyclohexylpropyl, 3-cyclohexyl-2-methylpropyl, and the like. The prefix indicating the number of carbon atoms (e.g., $C_4$–$C_{10}$) refers to the total number of carbon atoms from both the cycloalkyl portion and the alkyl portion.

"Haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, —$OR^a$, —$NR^bR^c$, and —$S(O)_nR^d$ (where n is an integer from 0 to 2), with the understanding that the point of attachment of the heteroalkyl radical is through a carbon atom of the heteroalkyl radical. $R^a$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. $R^b$ is hydrogen, alkyl, cycloalkyl, cycloalkyl-alkyl, aryl or aralkyl. $R^c$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. $R^d$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^a$, $R^b$, $R^c$, and $R^d$ can be further substituted by $NH_2$, fluorine, alkylamino, di-alkylamino, OH or alkoxy. Additionally, the prefix indicating the number of carbon atoms (e.g., $C_1$–$C_{10}$) refers to the total number of carbon atoms in the portion of the heteroalkyl group exclusive of the cyano, —$OR^a$, —$NR^bR^c$, or —$S(O)_nR^d$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R" are independently-hydrogen or alkyl, and R is hydrogen, alkyl, cycloalkyl, cycloalkyl-alkyl, phenyl or phenylalkyl), or —$(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkyl-alkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heteroaralkyl" means a radical —$R^aR^b$ where $R^a$ is an alkylene group and $R^b$ is a heteroaryl group as defined herein, e.g., pyridin-3-ylmethyl, 3-(benzofuran-2-yl)propyl, and the like.

"Heteroaralkenyl" means a radical —$R^aR^b$ where $R^a$ is an alkenylene group and $R^b$ is a heteroaryl group as defined herein, e.g., 3-(pyridin-3-yl)propen-2-yl, and the like.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —$(CR'R'')_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —$(CR'R'')_n$—$CONR^aR^b$ (where n is an integer from 0 to 5, R' and R" are independently hydrogen or alkyl, $R^a$ and $R^b$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrolidinyl, and the derivatives thereof. The prefix indicating the number of carbon atoms (e.g., $C_3$–$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —$R^aR^b$ where $R^a$ is an alkylene group and $R^b$ is a heterocyclyl group as defined herein, e.g., tetrahydropyran-2-ylmethyl, 4-methylpiperazin-1-ylethyl, 3-piperidinylmethyl, and the like.

"Heteroalkylene" means a linear saturated divalent hydrocarbon radical of one to six carbons or a branched saturated hydrocarbon radical of three to six carbon atoms with one, two or three substituents independently selected from —OR$^a$, —NR$^b$R$^c$, and —S(O)$_n$R$^d$ (where n is an integer from 0 to 2) where, R$^a$, R$^b$, R$^c$, and R$^d$ are as defined herein for a heteroalkyl radical. Examples include, 2-hydroxyethan-1,2-diyl, 2-hydroxypropan-1,3-diyl and the like.

"Heterosubstituted cycloalkyl" means a cycloalkyl group wherein one, two, or three hydrogen atoms are replaced by substituents independently selected from the group consisting of cyano, hydroxy, alkoxy, amino, acylamino, mono-alkyl amino, di-alkylamino, or —SO$_n$R (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl). Examples include 4-hydroxycyclohexyl, 2-aminocyclohexyl etc.

"Heteroalkyl substituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkyl substituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

The terms "modulate", "modulation" and the like refer to the ability of a compound to increase or decrease the function and/or expression of IKK, where IKK function may include kinase activity and/or protein-binding. Modulation may occur in vitro or in vivo. Modulation, as described herein, includes the inhibition or activation of IKK function and/or the downregulation or upregulation of IKK expression, either directly or indirectly. A modulator preferably activates IKK function and/or upregulates IKK expression. More preferably, a modulator activates or inhibits IKK function and/or upregulates or downregulates IKK expression. Most preferably, a modulator inhibits IKK function and/or downregulates IKK expression. The ability of a compound to inhibit IKK function can be demonstrated in an enzymatic assay or a cell-based assay (e.g., inhibition of IL-1-stimulated NF-κB activation).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrugs" means any compound which releases an active parent drug according to formula I in vivo when such prodrug is administered to a mammalian subject. Prodrugs of a compound of formula I are prepared by modifying functional groups present in the compound of formula I in such a way that the modifications may be cleaved in vivo to release the parent compound. Prodrugs include compounds of formula I wherein a hydroxy, amino, or sulfhydryl group in a compound of formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula I, and the like.

"Protecting group" refers to a grouping of atoms that when attached to a reactive group in a molecule masks, reduces or prevents that reactivity. Examples of protecting groups can be found in T. W. Greene and P. G. Futs, Protective Groups in Organic Chemistry, (Wiley, 2nd ed. 1991) and Harrison and Harrison et al., Compendium of Synthetic Organic Methods, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

"Treating" or "treatment" of a disease includes:
(1) preventing thee disease, i.e., causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, ie., causing regression of the disease or its clinical symptoms.

As used herein, the term "IKK-mediated condition or disease" and related terms and phrases refer to a condition or disorder characterized by inappropriate, e.g., less than or greater than normal, IKK activity. Inappropriate IKK functional activity might arise as the result of IKK expression in cells which normally do not express IKK, increased IKK expression (leading to, e.g., inflammatory and immunoregulatory disorders and diseases) or decreased IKK expression. An IKK-mediated condition or disease may be completely or partially mediated by inappropriate IKK functional activity. However, an IKK-mediated condition or disease is one in which modulation of IKK results in some effect on the underlying condition or disorder (e.g., an IKK inhibitor results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

The compounds of the present invention can also be produced in radiolabeled form and are useful in assays for evaluating the binding capabilities of compounds that interact with IKKα and with INKβ.

Embodiments of the Invention

Compounds

In one aspect, the present invention provides compounds useful in the treatment of inflammatory, metabolic or malignant conditions, having the formula:

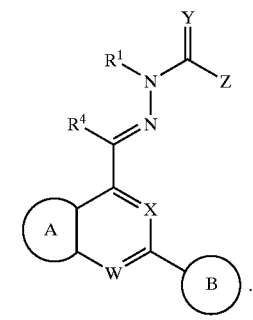

I

In formula I, the letters W and X independently represent N or CH; Y represents O, S or N(R), wherein R is H, CN, $NO_2$, $(C_1-C_{10})$alkyl, $(C_3-C_{10})$cycloalkyl, $(C_4-C_{10})$ cycloalkyl-alkyl, $(C_3-C_{10})$alkenyl or $(C_2-C_{10})$alkynyl; and Z represents H, $(C_1-C_{10})$alkyl, $(C_3-C_{10})$cycloalkyl, $(C_4-C_{10})$cycloalkyl-alkyl, $(C_2-C_{10})$alkenyl, $(C_2-C_{10})$ alkynyl or $NR^2R^3$.

The symbols $R^1$, $R^2$ and $R^3$ are independently H, $(C_1-C_{10})$alkyl, $(C_3-C_{10})$alkenyl, $(C_2-C_{10})$alkynyl, $(C_1-C_{10})$ heteroalkyl, $(C_3-C_{10})$cycloalkyl, $(C_4-C_{10})$cycloalkyl-alkyl, $(C_4-C_{10})$cycloheteroalkyl-alkyl, $(C_3-C_{10})$cycloheteroalkyl, aryl, aryl$(C_1-C_4)$alkyl, aryl$(C_1-C_4)$heteroalkyl, heteroaryl $(C_1-C_4)$alkyl, heteroaryl$(C_1-C_4)$heteroalkyl or perfluoro ($C_1$–$C_6$)allyl. Additionally, when Z is $NR^2R^3$, $R^2$ and $R^3$ can be combined to form a 5- to 7-membered heterocyclyl ring. The symbol $R^4$ represents H, ($C_1$–$C_6$)alkyl, ($C_3$–$C_6$) cycloalkyl, ($C_4$–$C_7$)cycloalkyl-alkyl, ($C_2$–$C_6$)alkenyl or ($C_2$–$C_6$)alkynyl.

In formula I, the letter A represents a substituted or unsubstituted fused carbocyclic or heterocyclic ring system, the A ring system being mono- or bicyclic wherein the mono- or bicyclic rings are five- or six-membered rings that are aromatic or partially or completely saturated.

In preferred embodiments, the letter A represents a fused ring selected from:

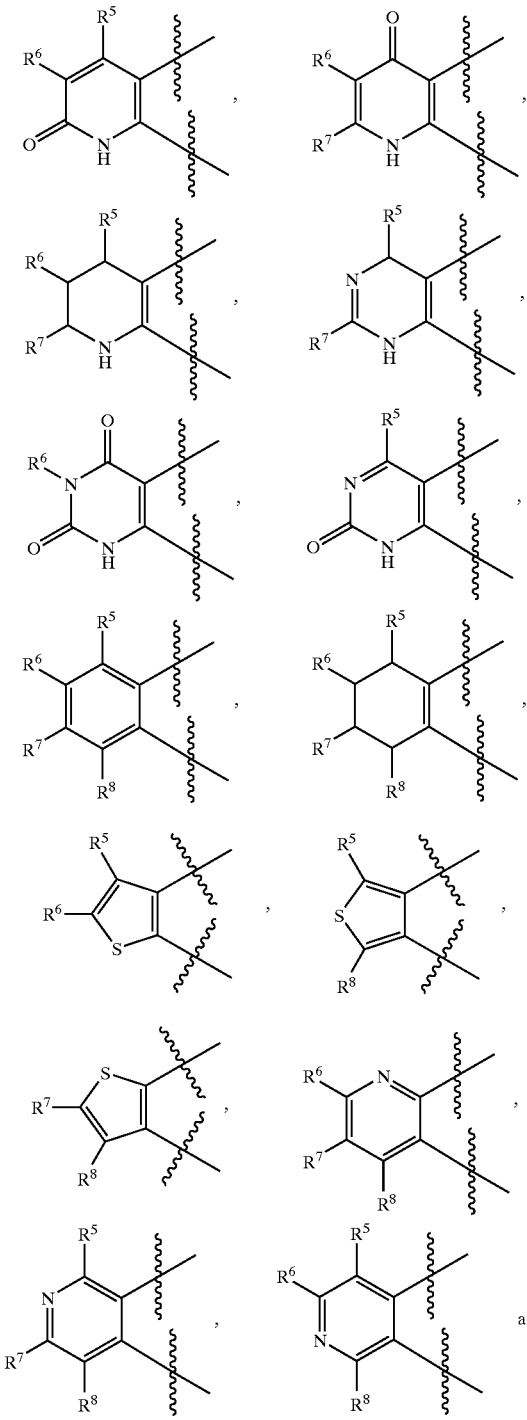

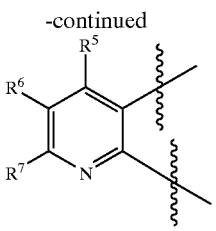

wherein $R^5$, $R^6$, $R^7$ and $R^8$ are independently selected from H, halogen, $CF_3$, $CF_3O$, ($C_1$–$C_6$)alkyl, ($C_2$–$C_6$)alkenyl, ($C_2$–$C_6$)alkynyl, ($C_1$–$C_6$)heteroalkyl, ($C_1$–$C_6$)alkoxy, ($C_1$–$C_6$)thioalkoxy, amino, ($C_1$–$C_6$)alkylamino, di($C_1$–$C_6$) alkylamino, ($C_3$–$C_{10}$)cycloalkyl, ($C_4$–$C_{10}$)cycloalkyl-alkyl, ($C_3$–$C_{10}$)cycloheteroalkyl, ($C_3$–$C_{10}$)cycloheteroalkyl-alkyl, cyano, nitro, ($C_1$–$C_6$)acyl, ($C_1$–$C_6$)acylamino, ($C_1$–$C_6$) alkoxycarbonyl, ($C_1$–$C_6$)alkoxycarbonyl($C_1$–$C_6$)alkyl, $CONH_2$, CO—NH—($C_1$–$C_6$)alkyl, CO—N[($C_1$–$C_6$)alkyl]$_2$, $SO_2NH_2$, $SO_2NH$—($C_1$–$C_6$)alkyl, $SO_2N$—[($C_1$–$C_6$)alkyl]$_2$ and ($C_1$–$C_6$)heteroalkoxy; or two adjacent R groups selected from $R^5$, $R^6$, $R^7$ and $R^8$ can be linked together to form a new 5- or 6-membered carbocyclic or heterocyclic ring. Additionally, any of the $R^5$, $R^6$, $R^7$ and $R^8$ groups can be optionally substituted by 1 to 3 of the following: CN, ($C_1$–$C_6$)alkyl-$SO_2$, ($C_1$–$C_6$)heteroalkyl-$SO_2$, $CONH_2$, CO—NH—($C_1$–$C_6$)alkyl, CO—N[($C_1$–$C_6$)alkyl]$_2$, $SO_2NH_2$, $SO_2NH$—($C_1$–$C_6$)alkyl, or $SO_2N$—[($C_1$–$C_6$) alkyl]$_2$.

The letter B represents a substituted or unsubstituted five- or six-membered ring which is aromatic or partially or completely saturated, containing at least one nitrogen atom, and from 0 to 3 additional heteroatoms, wherein the B ring substituents are selected from halogen, $CF_3$, $CF_3O$, ($C_1$–$C_6$) alkyl, perfluoro($C_1$–$C_6$)alkyl, ($C_2$–$C_6$)alkenyl, ($C_2$–$C_6$) alkynyl, ($C_1$–$C_6$)heteroalkyl, ($C_1$–$C_6$)alkoxy, ($C_1$–$C_6$) thioalkoxy, amino, ($C_1$–$C_6$)alkylamino, di($C_1$–$C_6$) alkylamino, ($C_3$–$C_{10}$)cycloalkyl, ($C_4$–$C_{10}$)cycloalkyl-alkyl, ($C_3$–$C_{10}$)cycloheteroalkyl, cyano, nitro, sulfonamido, ($C_1$–$C_6$)acyl, ($C_1$–$C_6$)acylamino, ($C_1$–$C_6$)alkoxycarbonyl, ($C_1$–$C_6$)alkoxycarbonyl($C_1$–$C_6$)alkyl, carboxamido and ($C_1$–$C_6$)heteroalkoxy.

Preferably, B contains a nitrogen atom at a position two atoms away from the atom attaching B to the remainder of the molecule or a nitrogen atom at the point of attachment of B to the remainder of the molecule. More preferably, B is selected from substituted or unsubstituted imidazolyl, substituted or unsubstituted thiazolyl and substituted or unsubstituted triazolyl. Still more preferably, B is selected from 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

In one group of embodiments, W is N and X is CH. Within this group of embodiments, Y is preferably O or S. More preferably, $R^4$ is H or $CH_3$. Still more preferably, A is selected from:

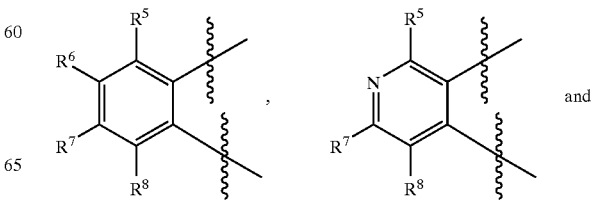

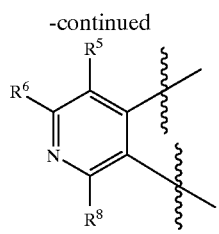

wherein the symbols $R^5$, $R^6$ and $R^7$ have the meanings provided above, and $R^8$ is H. Also preferred in this group of embodiments are those in which B contains a nitrogen atom at a position two atoms away from the atom attaching B to the remainder of the molecule. More preferably, B is substituted or unsubstituted imidazolyl, substituted or unsubstituted thiazolyl and substituted or unsubstituted triazolyl. Still more preferably, B is selected from 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

In another group of embodiments, W is N and X is CH. Within this group of embodiments, Y is preferably O or S. More preferably, Z is $NR^2R^3$.

In another group of embodiments, W is N and X is N. In still another group of embodiments, W is CH and X is N. In yet another group of embodiments, W and X are both CH.

In yet another group of preferred embodiments, Y is S; Z is $NH_2$; and $R^1$ is $(C_1-C_6)$alkyl, $(C_1-C_6)$heteroalkyl or $(C_3-C_{10})$cycloheteroalkyl-alkyl. In this group of embodiments, preferred groups for each of A and B are the same as have been described above.

In yet another group of preferred embodiments, Y is S; Z is $NH_2$; and $R^1$ is $CH_3$. In this group of embodiments, preferred groups for each of A and B are the same as have been described above.

In another group of preferred embodiments, W is N; X is CH; Y is O or S; Z is H, $CH_3$, $NH_2$ or $NHCH_3$; $R^1$ is H, $(C_1-C_6)$alkyl, $(C_1-C_{10})$heteroalkyl, $(C_4-C_{10})$cycloheteroalkyl-alkyl, $(C_3-C_{10})$cycloheteroalkyl, aryl $(C_1-C_4)$alkyl, aryl$(C_1-C_4)$heteroalkyl, heteroaryl$(C_1-C_4)$alkyl, heteroaryl$(C_1-C_4)$heteroalkyl, or perfluoro$(C_1-C_6)$alkyl; $R^4$ is H; A represents

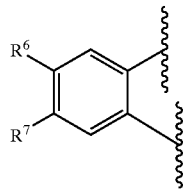

wherein $R^6$ and $R^7$ are independently selected from H, halogen, $CF_3$, $CF_3O$, $(C_1-C_4)$alkyl, $(C_2-C_4)$alkenyl, $(C_2-C_4)$alkynyl, $(C_1-C_4)$heteroalkyl, $(C_3-C_{10})$cycloheteroalkyl-alkyl and cyano; B represents a five-membered aromatic ring system containing at least one nitrogen atom. Preferably, B contains 1–2 nitrogen atoms and 0–1 sulfur atoms. Most preferably, B is unsubstituted or substituted by $(C_1-C_3)$alkyl, $CF_3$, cyano, or halogen. Most preferred in this group of embodiments are compounds in which Z is $NH_2$; $R^6$ is H, halogen, $CF_3$, $CF_3O$, $(C_1-C_4)$alkyl, $(C_2-C_4)$alkenyl, $(C_1-C_4)$heteroalkyl, $(C_3-C_{10})$cycloheteroalkyl-alkyl or cyano, and the alkyl, alkenyl and heteroalkyl groups optionally bear additional substituents selected from cyano, carboxamido, $(C_1-C_3)$alkylsulfonyl or $(C_1-C_3)$alkoxy; and $R^7$ is H, halogen, $CF_3$, $CF_3O$, $(C_1-C_4)$alkyl, $(C_2-C_4)$alkenyl, $(C_2-C_4)$alkynyl, $(C_1-C_4)$heteroalkyl or cyano.

In another group of preferred embodiments, Z is $NH_2$; $R^6$ is H, halogen, $CF_3$, $CF_3O$, $(C_1-C_4)$alkyl, $(C_2-C_4)$alkenyl, $(C_1-C_4)$heteroalkyl, $(C_3-C_{10})$cycloheteroalkyl-alkyl or cyano, wherein the alkyl, alkenyl and heteroalkyl groups optionally bear additional substituents selected from cyano, carboxamido, $(C_1-C_3)$alkylsulfonyl or $(C_1-C_3)$alkoxy; and R is H, halogen, $CF_3$, $CF_3O$, $(C_1-C_4)$alkyl, $(C_2-C_4)$alkenyl, $(C_2-C_4)$alkynyl, $(C_1-C_4)$heteroalkyl or cyano. Within this group of embodiments, $R^7$ is preferably H, halogen, $CF_3$ and $(C_1-C_4)$alkyl. In particularly preferred embodiments, $R^6$ is $CH_2(CH_2)_mCN$, $CH_2(CH_2)_nSO_2CH_3$ or $CH_2(CH_2)_nOCH_3$, wherein the subscript n is an integer from 0 to 2 Also particularly preferred are embodiments in which $R^6$ is

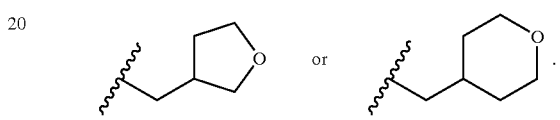

Yet another group of preferred embodiments is represented by the formula:

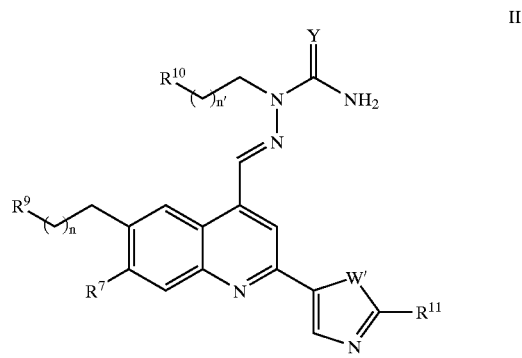

II wherein Y is O, S or N—CN; W' is $N(CH_3)$, $N(CF_3)$, $N(CH_2CH_3)$, O or S; the subscripts n and n' are independently integers from 0 to 3; $R^7$ is H, halogen, $CF_3$, $CF_3O$, $(C_1-C_4)$alkyl, $(C_2-C_4)$alkenyl, $(C_2-C_4)$alkynyl, $(C_1-C_4)$heteroalkyl or cyano; $R^9$ is CN, $CONH_2$, CO—NH—$(C_1-C_6)$alkyl, CO—N$[(C_1-C_6)$alkyl$]_2$, CO—NH—$(C_1-C_6)$heteroalkyl, CO—N$[(C_1-C_6)$heteroalkyl$]_2$, $S(O)_{n''}$—$(C_1-C_6)$alkyl, $S(O)_{n''}$—$(C_1-C_6)$heteroalkyl, heteroaryl, $(C_1-C_6)$alkoxy or $(C_3-C_6)$cycloheteroalkyl, wherein each n" is independently an integer of 0 to 2; $R^{10}$ is $NH_2$, NH—$(C_1-C_6)$alkyl, N$[(C_1-C_6)$alkyl$]_2$, NH—$(C_1-C_6)$heteroalkyl, N$[(C_1-C_6)$heteroalkyl$]_2$, $(C_1-C_6)$heteroalkyl, $S(O)_{n''}$—$(C_1-C_6)$alkyl, $S(O)_{n''}$—$(C_1-C_6)$heteroalkyl, aryl, heteroaryl, O—$(C_1-C_6)$alkyl, O—$(C_1-C_6)$heteroakyl or $(C_3-C_8)$cycloheteroalkyl; and $R^{11}$ is H, $CF_3$, $NH_2$, NH—$(C_1-C_6)$alkyl, N$[(C_1-C_6)$alkyl$]_2$, halogen or $(C_1-C_3)$alkyl. Most preferably, Y is O or S; W' is N—$CH_3$; n is 2; n' is 1 to 3; $R^9$ is cyano, $CONH_2$, $(C_1-C_6)$alkoxy, $(C_3-C_6)$cycloheteroalkyl or $SO_2$—$(C_1-C_6)$alkyl; $R^{10}$ is NH—$(C_1-C_6)$alkyl, N$[(C_1-C_6)$alkyl$]_2$, NH—$(C_1-C_6)$heteroalkyl, N$[(C_1-C_6)$heteroalkyl$]_2$, O—$(C_1-C_6)$alkyl, O—$(C_1-C_6)$heteroalkyl, $(C_1-C_6)$alkoxy or $(C_3-C_8)$cycloheteroalkyl; and $R^{11}$ is H.

Exemplary structures within this preferred group of embodiments are:
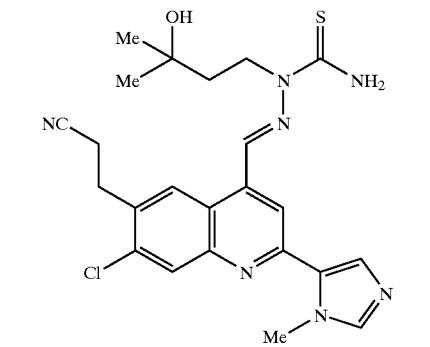
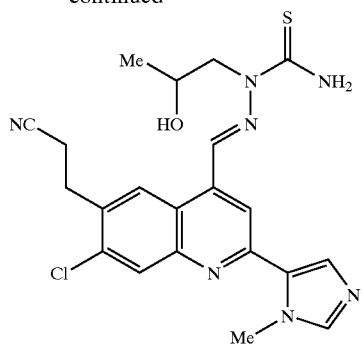
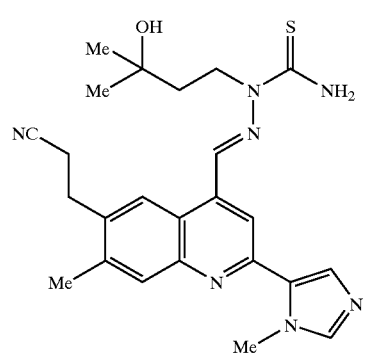
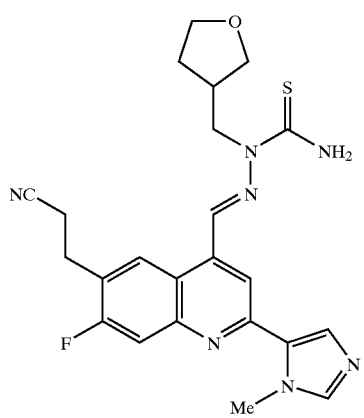
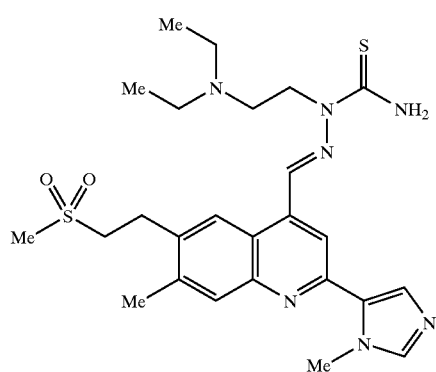
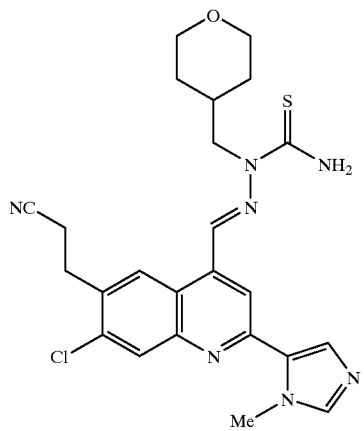
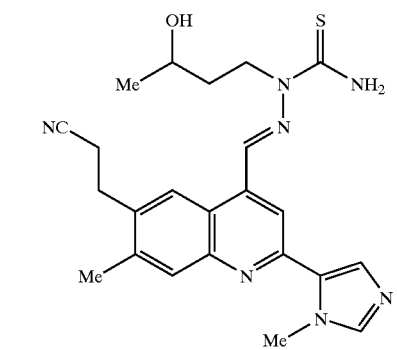
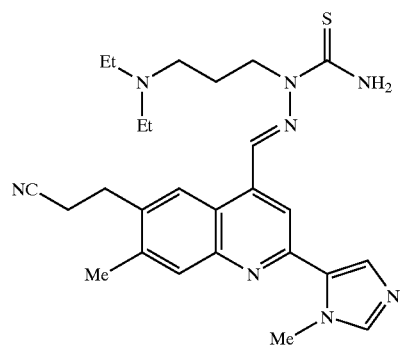

-continued
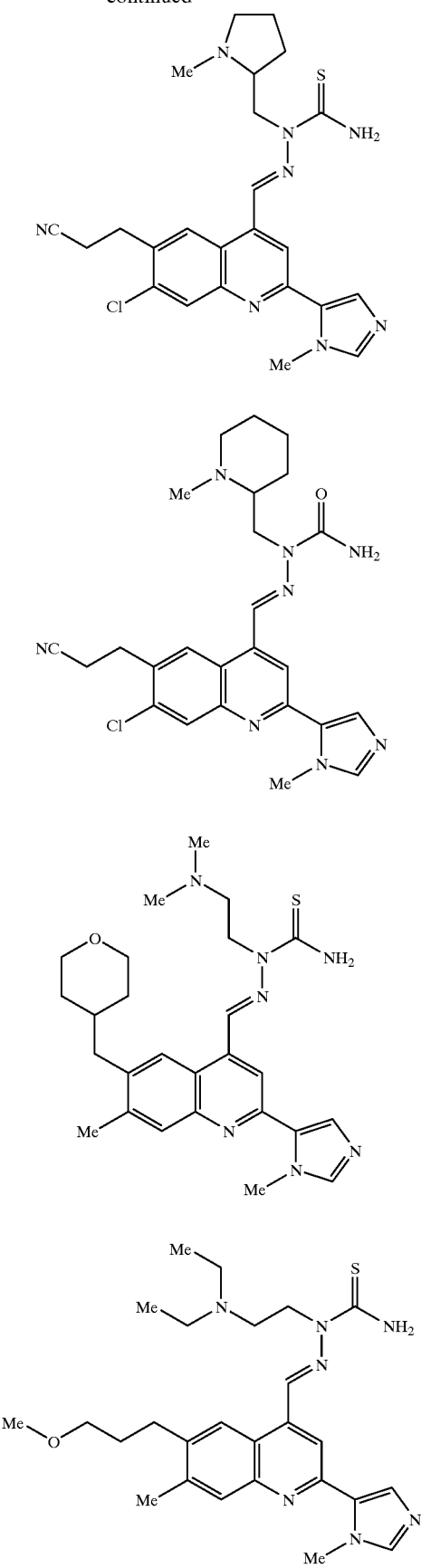
-continued
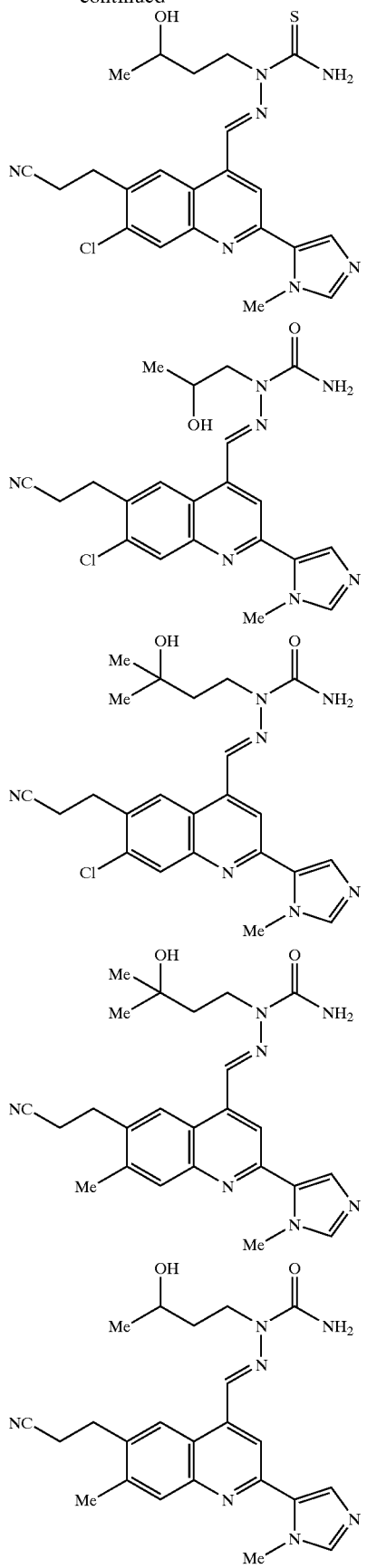

-continued

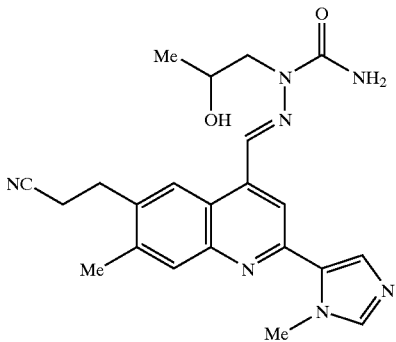

Preparation of Compounds of Formula I

General Scheme for Synthesis

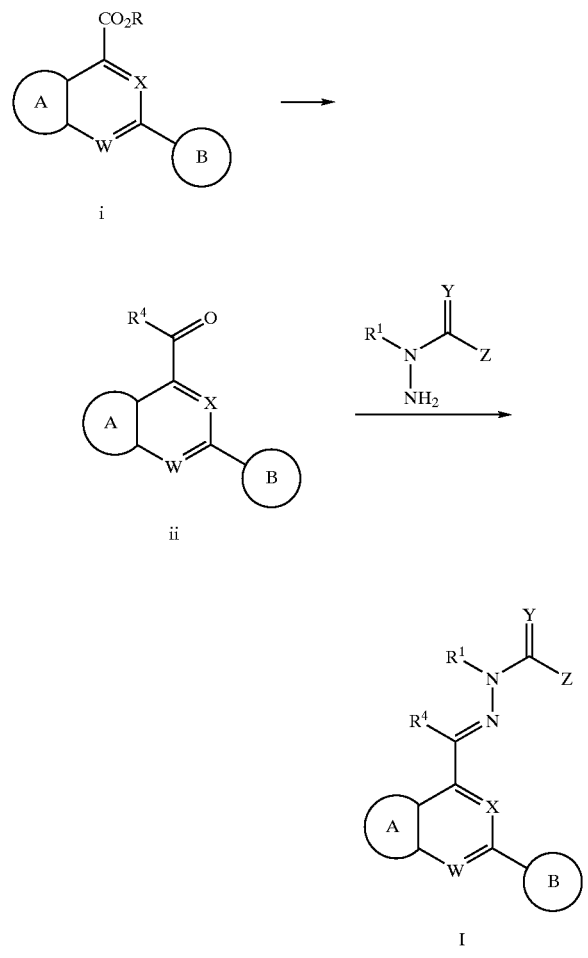

The synthesis of the target compounds is generally accomplished by reaction of the appropriate aldehyde (or ketone, when $R^4$ is other than H) ii with the appropriately substituted hydrazine derivative. In some cases, the aldehyde (or ketone) intermediate II is not fully isolated and/or characterized, but is simply synthesized from the corresponding ester i (or similar compound with the appropriate functional group) and utilized directly in the final reaction. The final products can be isolated, and purified if necessary, either by filtration, recrystallization, and/or chromatography, as appropriate.

The starting esters can be prepared by a variety of methods generally known to those skilled in the art of organic synthesis. Representative methods (Methods A–O) for the synthesis of these ester intermediates are provided in the Examples below.

In view of these preparative methods, the present invention further provides methods of preparing antiinflammation agents, comprising contacting a precursor compound having the formula:

ii

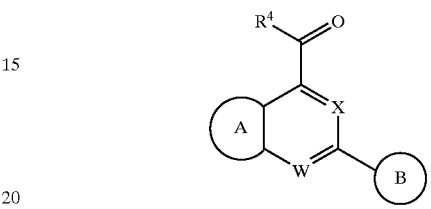

wherein W and X are independently selected from the group consisting of N and CH; $R^4$ is selected from the group consisting of H, $(C_1-C_6)$alkyl, $(C_3-C_6)$cycloalkyl, $(C_4-C_7)$ cycloalkyl-alkyl, $(C_2-C_6)$alkenyl and $(C_2-C_6)$alkynyl; A is a substituted or unsubstituted fused carbocyclic or heterocyclic ring system, the ring system being mono- or bicyclic wherein the mono- or bicyclic rings are selected from the group consisting of five- and six-membered rings that are aromatic or partially or completely saturated; and B is a substituted or unsubstituted five- or six-membered ring which is aromatic or partially or completely saturated, containing at least one nitrogen atom, and from 0 to 3 additional heteroatoms, wherein the B ring substituents are selected from halogen, $CF_3$, $CF_3O$, $(C_1-C_6)$alkyl, perfluoro $(C_1-C_6)$alkyl, $(C_2-C_6)$alkenyl, $(C_2-C_6)$alkynyl, $(C_1-C_6)$ heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$ cycloalkyl, $(C_4-C_{10})$cycloalkyl-alkyl, $(C_3-C_{10})$ cycloheteroalkyl, cyano, nitro, sulfonamido, $(C_1-C_6)$acyl, $(C_1-C_6)$acylamino, $(C_2-C_6)$alkoxycarbonyl, $(C_2-C_6)$ alkoxycarbonyl$(C_1-C_6)$alkyl, carboxamido and $(C_1-C_6)$ heteroalkoxy; with a compound having the formula:

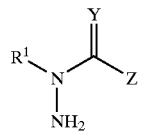

wherein Y is O, S or N(R), wherein R is H, CN, $NO_2$, $(C_1-C_{10})$alkyl, $(C_3-C_{10})$cycloalkyl, $(C_4-C_{10})$cycloalkyl-alkyl, $(C_3-C_{10})$alkenyl and $(C_2-C_{10})$alkynyl; Z is H, $(C_1-C_{10})$alkyl, $(C_3-C_{10})$cycloalkyl, $(C_4-C_{10})$cycloalkyl-alkyl, $(C_2-C_{10})$alkenyl, $(C_2-C_{10})$alkynyl or $NR^2R^3$; $R^1$, $R^2$ and $R^3$ are independently selected from H, $(C_1-C_{10})$alkyl, $(C_3-C_{10})$alkenyl, $(C_2-C_{10})$alkynyl, $(C_2-C_{10})$heteroalkyl, $(C_3-C_{10})$cycloalkyl, $(C_4-C_{10})$cycloalkyl-alkyl, $(C_3-C_{10})$ cycloheteroalkyl-alkyl, $(C_3-C_{10})$cycloheteroalkyl, aryl, aryl $(C_1-C_4)$alkyl, aryl$(C_2-C_4)$heteroalkyl, heteroaryl$(C_2-C_4)$ alkyl, heteroaryl$(C_2-C_4)$heteroalkyl and perfluoro$(C_1-C_6)$ alkyl; and wherein when Z is $NR^2R^3$, $R^2$ and $R^3$ can be combined to form a 5- to 7-membered ring; under conditions sufficient to produce compounds having the formula:

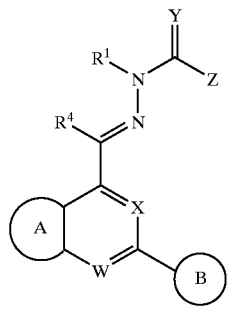

I wherein each of A, B, $R^1$, $R^4$, W, X, Y and Z have the meanings provided above.

Exemplary conditions are provided in the examples below, with the understanding that the skilled practitioner can adjust solvents, temperature, time of reaction, workup conditions and the like to produce the desired compounds.

In view of the methods provided herein, one of skill will also appreciate that certain compounds are particularly useful in the preparation of the subject antiinflammation agents. Accordingly, the present invention provides in another aspect, to compounds of the formula:

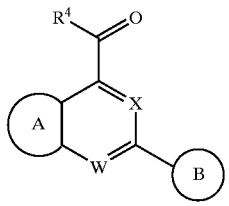

ii wherein W and X are independently selected from N and CH; $R^4$ is selected from H, $(C_1-C_6)$alkyl, $(C_3-C_6)$ cycloalkyl, $(C_4-C_7)$cycloalkyl-alkyl, $(C_2-C_6)$alkenyl and $(C_2-C_6)$alkynyl; A is a substituted or unsubstituted fused carbocyclic or heterocyclic ring system, the ring system being mono- or bicyclic wherein the mono- or bicyclic rings are selected from five- and six-membered ring s that are aromatic or partially or completely saturated; and B is a substituted or unsubstituted five- or six-membered ring which is aromatic or partially or completely saturated, containing at least one nitrogen atom, and from 0 to 3 additional heteroatoms, w the B ring substituents are selected from halogen, $CF_3$, $CF_3O$, $(C_1-C_6)$alkyl, perfluoro $(C_1-C_6)$alkyl, $(C_2-C_6)$alkenyl, $(C_2-C_6)$alkynyl, $(C_1-C_6)$ heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$ cycloalkyl, $(C_4-C_{10})$cycloalkyl-alkyl, $(C_3-C_{10})$ cycloheteroalkyl, cyano, nitro, sulfonamido, $(C_1-C_6)$acyl, $(C_1-C_6)$acylamino, $(C_2-C_6)$alkoxycarbonyl, $(C_2-C_6)$ alkoxycarbonyl$(C_1-C_6)$alkyl, carboxamido and $(C_1-C_6)$ heteroalkoxy.

Compositions

In addition to the compounds provided above, the present invention further provides pharmaceutical compositions comprising one or more of the subject compounds in admixture with a pharmaceutically acceptable carrier or excipient.

In one embodiment, the invention provides the subject compounds combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc., to form pharmaceutically acceptable compositions.

In another embodiment, the invention provides the subject compounds in the form of a prodrug, which can be metabolically or chemically converted to the subject compound by the recipient host. A wide variety of prodrug derivatives are known in the art such as those that rely on hydrolytic cleavage or oxidative activation of the prodrug.

The compositions may be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

Still other compositions of the present invention are those that combine two or more of the present compounds in one formulation, or one compound from the present invention with a second antiinflammatory, antiproliferative or antidiabetic agent.

Methods of Use

In yet another aspect, the present invention provides methods of treating IKK-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

Diseases and conditions associated with inflammation, infection and cancer can be treated with the present compounds and compositions. In one group of embodiments, diseases or conditions, including chronic diseases, of humans or other ret species can be treated with inhibitors of IKK function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome); (5) in another group of embodiments, diseases or conditions are treated with inhibitors of IKK function that will promote cell death; examples of these diseases include, but are not limited to, neoplastic diseases such as solid tumors, skin cancer, melanoma, lymphoma, and diseases in which angiogenesis and neovascularization play a role; (6) other metabolic disorders that are sensitive to inhibition of TNF or IL-1 signaling, such as obesity for example.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection or implant), inhalation, nasal, vaginal, rectal, sublingual transdermal or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds maybe administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory and immunoregulatory disorders and diseases, including asthma and allergic diseases, as well as autoimmune pathologies such as rheumatoid arthritis and atherosclerosis, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin receptor antagonist, such as an interleukin-1 receptor antagonist, an NMDA receptor antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sulindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antitussive such as codiene, hydrocodone, caramiphen, carbetapentane, or dextramethorphan; a diuretic; and a sedating or non-sedating antihistamine. Each of the above agents may be administered, by a route and in an amount commonly used therefor, contemporaneously or sequentially with a compound of the present invention. When a compound of the present invention is used contemporaneously with one or more other drugs, in some cases a pharmaceutical composition containing such other drugs in addition to the compound of the present invention may be preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as methotrexate cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta-adrenergic agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) anti-diabetic agents such as insulin, sulfonylureas, biguanides (metformin), α-glucosidase inhibitors (acarbose) and glitazones (troglitazone, rosiglitazone and pioglitazone); (j)

preparations of interferon beta (interferon beta-1.alpha, interferon beta-1.beta.); (k) other compounds such as 5-aminosalicylic acid and prodrugs thereof, antimetabolites such as methotrexate, azathioprine and 6-mercaptopurine, and cytotoxic cancer chemotherapeutic agents; and (1) agents that directly or indirectly interfere with cytokine signalling, such as soluble TNF receptors, TNF antibodies, soluble IL-1 receptors, IL-1 antibodies, and the like. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:000, preferably about 200:1 to about 1:200. Combinations of a compound of the present invention and other active ingredients will generally also be within the aforementioned range, but in each case, an effective dose of each active ingredient should be used.

EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlelt Packard 5989A mass spectrometer. Mass spectrometry results are reported as the ratio of mass over charge, followed by the relative abundance of each ion (in parentheses). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1100 HPLC for sample delivery. Normally the analyte was dissolved in methanol at 0.1 mg/mL and 1 microliter (μL) was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH$_4$OAc in acetonitrile/water as delivery solvent.

Preparation of Synthetic Intermediates

Method A

For compounds of the invention in which W=N and X=CH, and the corresponding α-keto lactam (i.e., isatin) is commercially available or can be prepared by known methods.

Scheme 1

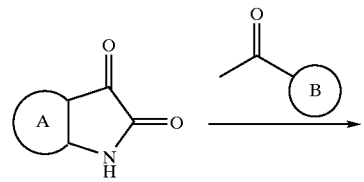

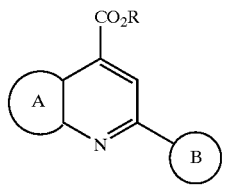

Preparation of Intermediate iii

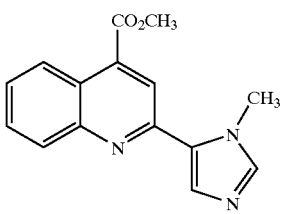

Step 1:

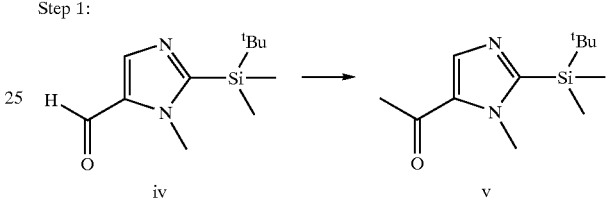

To a solution of the aldehyde iv (22.0 g, 98.0 mmol; prepared according to Walters, et al. Tetrahedron Lett. 1994, 35, 8307–8310) in 200 mL of THF at 0° C. was added a 3.0 M solution of MeMgCl (39 mL, 117.0 mmol) in THF. The reaction was stirred for 30 min and quenched with a saturated NH$_4$Cl solution. The solids were removed by filtration, the filtrate was dried over Na$_2$SO$_4$, and concentrated to dryness to obtain a solid. The crude product and MnO$_2$ (36.0 g) were stirred vigorously in 100 mL of benzene for 18 h. More MnO$_2$ (5.0 g) was added and the mixture was stirred for another 3 h. The reaction was filtered through Celite, the solids were washed with EtOAc, and the filtrate was concentrated to give a solid. The crude product was purified by chromatography (silica gel, hexanes/acetone, 85:15) to give the desired ketone v as a solid (16 g, 68%). $^1$H NMR (DMSO-d$_6$) δ 8.00 (s, 1H), 3.89 (s, 3H), 2.43 (s, 3H), 0.92 (s, 9H), 0.36 (s, 6H).

Step 2:

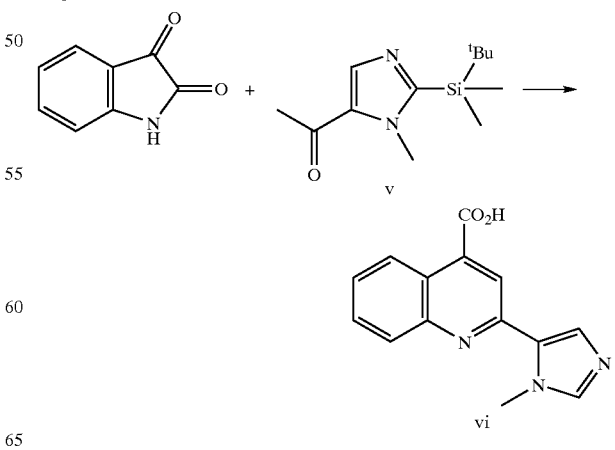

To a mixture of isatin (1.2 g, 8.15 mmol, Aldrich Chemical Co., Milwaukee, Wis., USA) and 5-acetyl-2-t- butyldimethylsilyl-1-methyl imidazole (2.0 g, 8.4 mmol, prepared in Step 1) in 10 mL of EtOH/water (1:1) was added potassium hydroxide (2.0 g, 35.6 mmol). The dark-red solution was stirred in an oil bath at 80° C. for 18 h. The reaction was cooled in an ice bath, diluted with water (5 mL) and acetic acid (2 mL) was added. The precipitate was collected by filtration, washed with water, and dried to give the desired product vi (1.3 g). $^1$H NMR (DMSO-d$_6$) δ 8.54 (dd, J=8.5, 1.0 Hz, 1H), 8.02 (s, 1H), 8.0 (dd, J=8.3, 1.0 Hz, 1H), 7.85 (s, 1H), 7.78 (s, 1H), 7.73 (ddd, J=8.3, 6.7, 1.4 Hz, 1H), 7.55 (ddd, J=8.3, 6.8, 1.3 Hz, 1H), 4.14 (s, 3H).

Step 3:

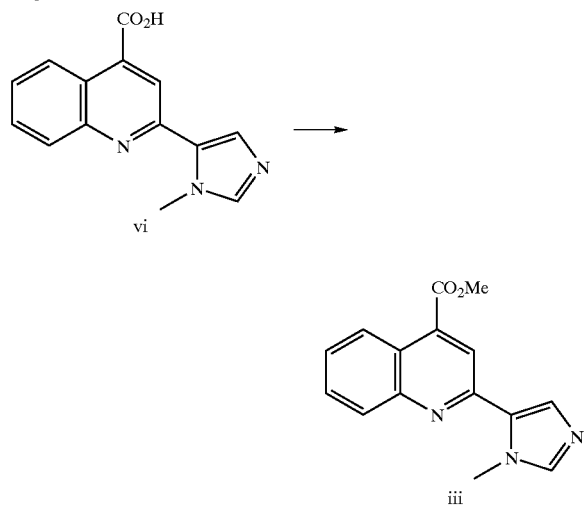

The acid vi (500 mg, 1.99 mmol) was dissolved in 5 mL of MeOH and conc. H$_2$SO$_4$ (1.0 mL) was added. The reaction mixture was heated at reflux for 22 h and brought to room temperature. The mixture was concentrated and the residue was dissolved with water and adjusted to basic pH by the addition of solid K$_2$CO$_3$. The aqueous phase was extracted three times with EtOAc. The organic extracts were washed with brine, dried over MgSO$_4$, filtered and concentrated to dryness to give the desired ester iii (300 mg). $^1$H NMR (DMSO-d$_6$) δ 8.47 (d, J=8.4 Hz, 1H), 8.26 (s, 1H), 8.08 (d, J=8.4 Hz, 1H), 7.93–7.87 (br s, 2H), 7.84 (br t, J=7.0 Hz, 1H), 7.67 (br t, J=7.0 Hz, 1H), 4.15 (s, 3H), 4.02 (s, 3H).

A number of variously substituted isatins are available from commercial sources. Alternatively, literature methods described their preparation from the corresponding anilines (or equivalent aromatic amines). For example, substituted isatins can be prepared via a Sandmeyer procedure (see, Simon J. Garden, Jose C. Torres, Alexandra A. Ferreira, Rosangela B. Silva, Angelo C. Pinto; *Tetrahedron Letters* 38, 9, 1501, (1997) and references cited therein); a formanilide method (see, Otto, et al., *Tetrahedron Letters* 37, 52, 9381, (1996)); a Stolle type procedure (see, Soll, et al., *J. Org. Chem.* 53, 2844 (1988)); a Stolle-Becker (oxalyl chloride) procedure (see, Baumgarten, et al., *J. Org. Chem.* 26, 1536 (1961)); α keto amides (see, Fumiyuki, et al., *J. Org. Chem.* 51, 415, (1986)); a Gassman method (see, Gassman, et al., *J. Org. Chem.* 42, 8, 1344, (1977)); ortholithiated anilines (see, Hewawasam, et al., *Tetrahedron Letters*, 35, 7303,(1994)); an oxindole route (see, Kraynack et al., *Tetrahedron Letters*, 39, 7679, (1998); and via bis (alkylthio)carbenes (see Rigby, and Danca, *Tetrahedron Letters* 40, 689, (1999)).

Method B

Preparation of Intermediate vii

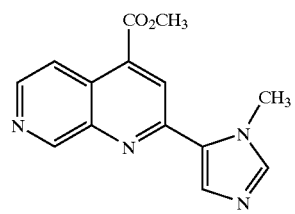

Step 1:

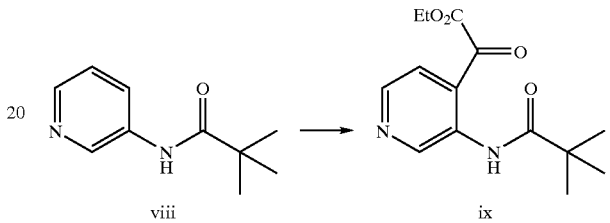

A solution of the amide viii (1.87 g, 10.6 mmol) in 20 mL of THF was cooled to −78° C. under nitrogen. A 2.32 M solution of n-BuLi (11.4 mL, 26.5 mmol) in THF was added to the cold solution, which was then stirred at −5° C. for 3 h. The reaction was cooled to −78° C. and diethyl oxalate (3.65 mL, 26.5 mmol) was added. The reaction was allowed to reach room temperature and was quenched with water, followed by EtOAc. The aqueous phase was extracted three times with EtOAc, the organic extracts were combined, dried over MgSO$_4$, filtered, and concentrated to dryness to obtain an oil (1.8 g). The crude product was purified by chromatography (silica gel, CH$_2$Cl$_2$/MeOH, 97:3) to give the desired ketoester ix as an oil (680 mg, 23%).

Step 2:

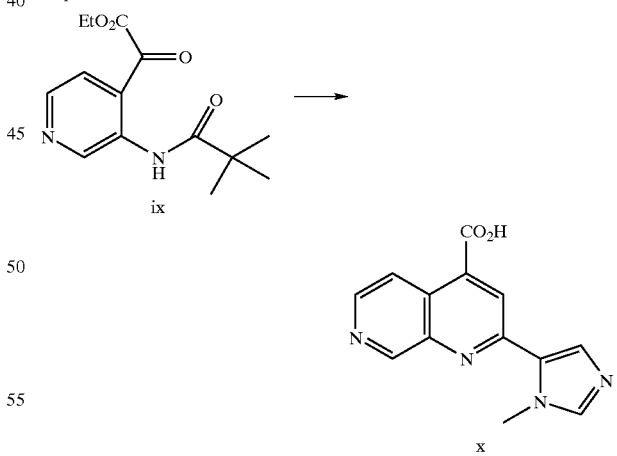

A mixture of the ketoester ix (680 mg, 2.44 mmol), 5-acetyl-2-t-butyldimethylsilyl-1-methyl imidazole v (660 mg, 2.76 mmol), and potassium hydroxide (564 mg, 10.07 mmol) in 6 mL of EtOH/water (1:1) was placed in an oil bath at 80° C. for 18 h. The reaction was brought to room temperature, concentrated to remove the EtOH, diluted with 3 mL of water, and 1 mL of AcOH was added. The solution wan refrigerated for 24 h, at which point a solid precipitate was collected, washed with water, and dried to give the desired acid x (200 mg, 32%). ¹H NMR (DMSO-d₆) δ 9.26 (s, 1H), 8.60 (d, J=5.7 Hz, 1H), 8.46 (d, J=5.7 Hz, 1H), 8.09 (s, 1H), 7.85 (s, 1H), 7.77 (s, 1H), 4.15 (s, 3H).

The corresponding ester of this acid can be prepared as described in Method A, Step 3, or other standard methods known to those of skill in the art. Alternatively, this acid can be converted directly into the corresponding aldehyde using methods well known in the art.

Method C

Preparation of Intermediate xi

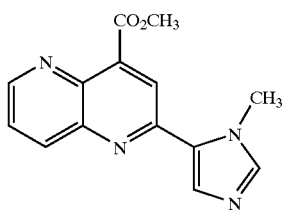

This method is a variation on Method B; above. In this method, metal-halogen exchange is used instead of direct metallation of an aniline derivative.

Step 1:

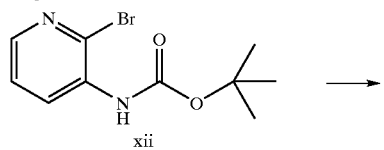

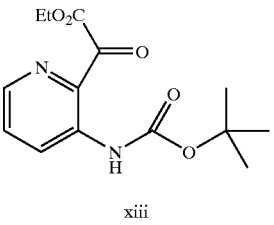

A solution of the required carbamate xii (1.74 g, 6.37 mmol; prepared according to Venuti et al., *J. Med. Chem.* 1988, 31, 2136) in 20 mL of THF was cooled to −78° C. under nitrogen. A 2.2-M solution of n-BuLi (6.1 mL, 13.4 mmol) in THF was added to the cold solution and the mixture was stirred at −78° C. for 1 h. Diethyl oxalate (1.04 mL, 7.64 mmol) was added and the reaction was allowed to reach room temperature. The reaction was quenched with 10% aqueous NH₄Cl and diluted with EtOAc. The organic layer was washed with water, brine, dried over MgSO₄, filtered, and concentrated to dryness to obtain an oil (1.79 g). The crude product was purified by chromatography (silica gel, hexanes/EtOAc, 4:1) to give the desired ketoester xiii as an oil (1.1 g, 58%).

Step 2:

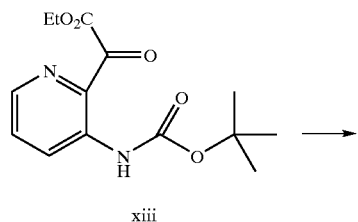

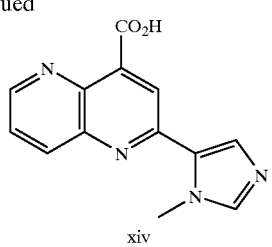

A mixture of the ketoester xiii (1.0 g, 3.4 mmol), 5-acetyl-2-t-butyldimethylsilyl-1-methyl imidazole v (882 mg, 3.7 mmol), and potassium hydroxide (760 mg, 13.6 mmol) in 8 mL of EtOH/water (1:1) was placed in an oil bath at 80° C. for 24 h. The reaction was brought to room temperature, diluted with 20 mL of water, and 2 mL of AcOH was added. The yellow solution was refrigerated for 4 h and the yellow needles that formed were collected by filtration, washed with water and ether, and dried to give the desired acid xiv (163 mg, 19%). ¹H NMR (DMSO-d₆) δ 9.02 (dd, J=4.3, 1.6 Hz, 1H), 8.55 (dd, J=8.5, 1.6 Hz, 1H), 8.46 (s, 1H), 8.01 (d, J=1.0 Hz, 1H), 7.92 (dd, J=8.5, 4.3 Hz, 1H), 7.91 (s, 1H), 4.15 (s, 3H).

The corresponding ester of this acid can be prepared as described in Method A, Step 3, or by other methods known in the art. Alternatively, this acid can be converted directly into the corresponding aldehyde or ketone by known methods.

Method D

An alternative method of assembling the final framework involves a tin-mediated coupling as indicated below.

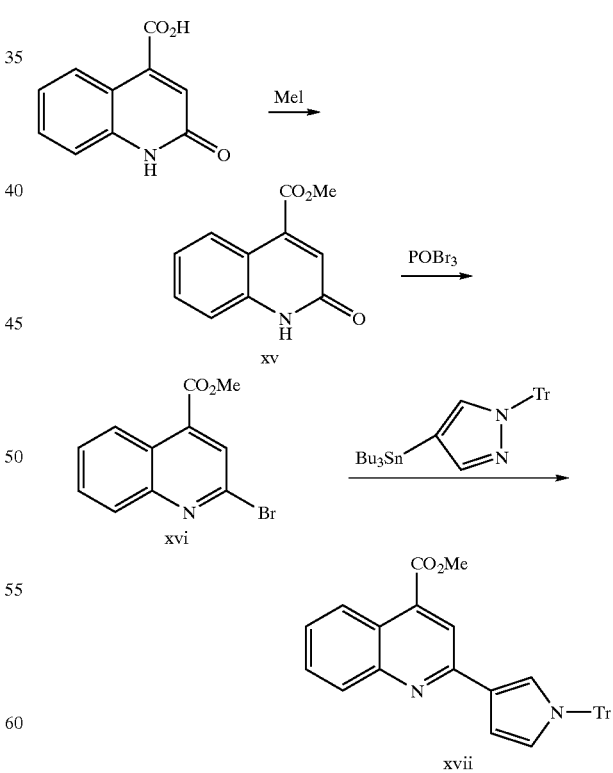

To a stirred solution of 2-hydroxyquinoline-4-carboxylic acid (Lancaster, Windham, USA) (10 g, 50 mmol), anhydrous potassium carbonate (10.35 g, 75 mmol) and anhydrous DMF (200 mL) at room temperature under nitrogen was added iodomethane (6.14 mL, 100 mmol). The mixture was stirred for 16 h, then poured into saturated aqueous sodium bicarbonate (150 mL). The resulting solid was washed with water (2×50 mL) and dried by suction to afford the desired product xv (9.1 g, 90%). $^1$H NMR (DMSO-d$_6$) δ 12.14 (br s, 1H), 8.05 (d, J=8 Hz, 1H), 7.55–7.60 (m, 1H), 7.39 (d, J=8 Hz, 1H), 7.21–7.28 (m, 1H), 6.85 (s, 1H), 3.93 (s, 3H); ESI-MS m/z 204.1 (100, M+H$^+$).

A solution of 4-carbomethoxy-2-quinolinone xv (655 mg, 3 mmol) and POBr$_3$ (1.9 g, 10 mmol) in toluene (20 mL) was heated at reflux for 2 h, then allowed to cool to room temperature and poured into ice water (25 mL). The mixture was extracted with ethyl acetate (3×50 mL). The organic extract was combined, washed with water and brine, dried (MgSO$_4$) and concentrated in vacuo. Flash chromatography (hexane:EtOAc 4:1) afforded the desired product xvi (400 mg). $^1$H NMR (DMSO-d$_6$) δ 8.52–8.57 (m, 1H), 8.04–8.08 (m, 1H), 8.25 (s, 1H), 7.88–7.92 (m, 1H), 7.76–7.81 (m, 1H), 3.98 (s, 3H).

A solution of 4-tributylstannyl-1-tritylimidazole (474 mg, 0.79 mmol; prepared according to Elguero et al., *Synthesis*, 1997, 563) and 2-bromo4-carbomethoxy-quinoline xvi (145 mg, 0.53 mmol) in DMF was degassed with nitrogen for 5 min. Pd$_2$(dba)$_3$ (49 mg, 0.053 mmol), cuprous iodide (20 mg, 0.1 mmol) and triphenyl arsine (32 mg, 0.10 mmol) were added, and the mixture was stirred at 60° C. for 16 h. The mixture was allowed to cool to room temperature and was filtered through celite (eluting with 50 mL ethyl acetate). Water (50 mL) was added and the organic extract was collected and washed with water (3×50 mL), brine (1×50 mL), dried (MgSO$_4$), filtered and concentrated in vacuo. Flash chromatography (gradient elution: hexane to hexane:EtOAc 3:1) afforded the desired product xvii (173 mg, 66%). $^1$H NMR (CDCl$_3$) δ 8.62 (d, J=8 Hz, 1H), 8.36 (s, 1H), 8.20 (s, 1H), 8.04–8.07 (m, 2H), 7.17–7.76 (m, 17H), 4.04 (s, 3H); ESI-MS m/z 496.3 (100, M+H$^+$).

The general synthetic methodology of Method D can also be applied to other aromatic halides. For example:

Preparation of Intermediate xix

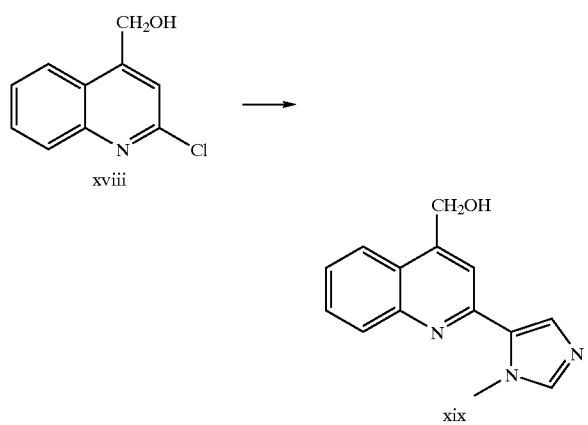

To a solution of 1-methyl-5-(tributylstannyl)imidazole (9.5 g, 25.6 mmol, Gaare, et al., *Acta Chem. Scand.* 1993, 47(1), 57–62) in 75 mL of anhydrous benzene which had been degassed by bubbling nitrogen through it for 5 min. was added the chloro quinoline xviii (4.1 g, 21.3 mmol, Hasegawa, *Pharm. Bull.* 1953, 47–50). To this solution was added tetrakis(triphenylphosphine)palladium(0) (1.06 mmol, 1.23 g). The reaction was heated at reflux for 14 h, at which time it was cooled, the volume of solvent reduced to about 15 mL under vacuum and the solution placed on a silica gel column. The column was eluted with 5% MeOH in methylene chloride to give 3.5 g of the alcohol xix.

$^1$H NMR (CDCl$_3$) δ 8.02 (d, J=7.0 Hz, 1H), δ 7.99 (d, J=7.0 Hz, 1H), 7.91 (s, 1H), 7.84 (s, 1H), 7.73 (t, J=7.0 Hz, 1H), 7.71 (s, 1H), 5.64 (t, J=5.6 Hz, 1H), 5.04 (d, J=5.6 Hz, 2H), 4.15 (s, 3H).

This alcohol can then be converted into the corresponding aldehyde as described for Example 1.9, or by other methods well known in the art.

Method E

This method is a variation on Method D, although in this case the fused A ring is not aromatic, and an aromatic triflate is used in the coupling reaction.

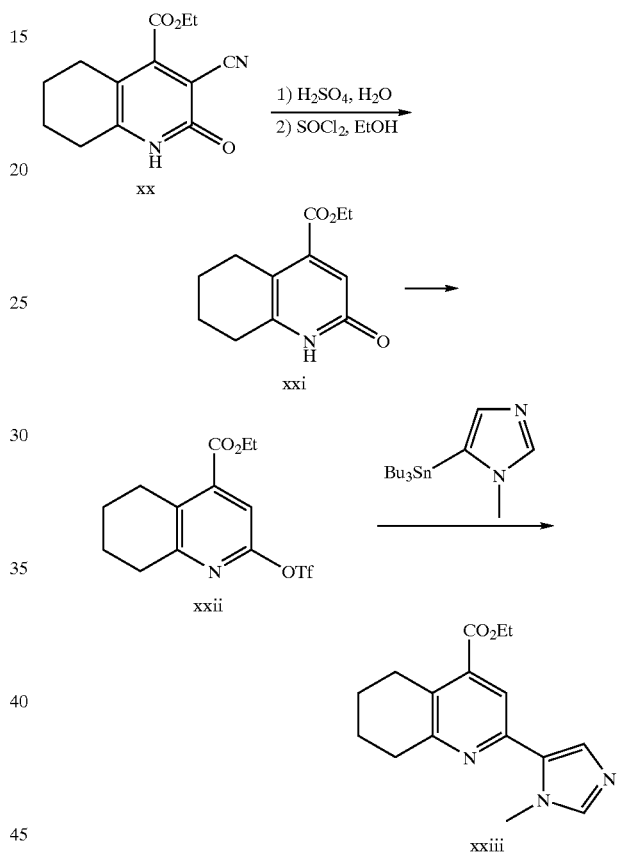

A mixture of ethyl 3-cyano-2-hydroxy-5,6,7,8-tetrahydroquinoline-4-carboxylate xx (7.8 g, 0.032 mol; prepared according to Snyder, *Org. Synth.*, II, 531 and Isler et al., *Helv. Chim. Acta*, 1955, 38, 1033) in water (9 mL) and conc. H$_2$SO$_4$ (9 mL) was heated at reflux for 3 days. The mixture was cooled and diluted with water. The resulting precipitate was collected by filtration and washed with water to give the desired carboxylic acid (4.4 g, 71%). $^1$H NMR (DMSO-d$_6$) δ 6.34 (s, 1H), 2.10–2.20 (m, 4H), 1.61–1.70 (m, 4H); ESI-MS m/z 192.1 (100, M−H$^+$).

To the carboxylic acid (4.4 g, 22 mmol) was added thionyl chloride (30 mL) and the mixture was heated at reflux for 1 h, then allowed to cool to room temperature and concentrated in vacuo. To the residue was added ethanol (20 mL) and the mixture was stirred at room temperature for 5 min. The mixture was concentrated in vacuo to afford ester xxi (3.4 g, 70%). $^1$H NMR (CDCl$_3$) δ 6.80 (s, 1H), 4.17 (q, J=7 Hz, 2H), 2.65–2.75 (m, 4H) 1.66–1.85 (m, 4H), 1.29 (t, J=7 Hz, 3H); ESI-MS m/z 222.2 (100, M+H$^+$).

To a stirred solution of pyridone xxi (400 mg, 1.8 mmol) in anhydrous dichloromethane (15 mL) at 0° C. under nitrogen was added diisopropylethylamine (347 μl, 1.98 mmol) and triflic anhydride (192 μl, 1.8 mmol). After 3 h, saturated aqueous sodium bicarbonate (10 mL) was added and the organic layer was collected, dried (Na2SO$_4$), filtered and concentrated in vacuo. Flash chromatography (hexane:EtOAc 95:5) afforded the desired pyridine triflate xxii (173 mg, 27%). $^1$H NMR (CDCl$_3$) δ 7.26 (s, 1H), 4.19 (q, J=7 Hz, 2H), 2.83–3.07 (m, 4H) 1.79–1.94 (m, 4H), 1.30 (t, J=7 Hz, 3H). ESI-MS m/z 354.0 (100, M+H$^+$).

To a stirred solution of triflate xxii (173 mg, 0.48 mmol) in 1,4-dioxane (5 mL) was added tetrakis(triphenylphosphine)palladium(0) (60 mg, 0.05 mmol), lithium chloride (67 mg, 1.5 mmol) and 1-methyl-5-(tributylstannyl)imidazole (216 mg, 0.58 mmol) and the mixture was degassed with nitrogen for 5 min. The mixture was, heated at reflux for 18 h under nitrogen, then cooled and diluted with dichloromethane and water. The organic layer was collected, washed with brine, dried (Na$_2$SO$_4$), filtered and concentrated in vacuo. Flash chromatography (CH$_2$Cl$_2$ to CH$_2$Cl$_2$: MeOH 1.5:98.5) afforded the desired product xxiii (168 mg). $^1$H NMR (CDCl$_3$) δ 7.63 (s, 1H), 7.41 (s, 1H), 7.43 (s, 1H), 4.39 (4, J=7 Hz, 2H), 3.99 (s, 3H), 2.83–3.07 (m, 4H), 1.78–1.95 (m, 4H), 1.29 (t, J=7 Hz, 3H). MS m/z 286.2 (100, M+H$^+$).

Method F

This method also illustrates a variation to Method D, but in this case W=X=CH (utilizing a naphthalene framework).

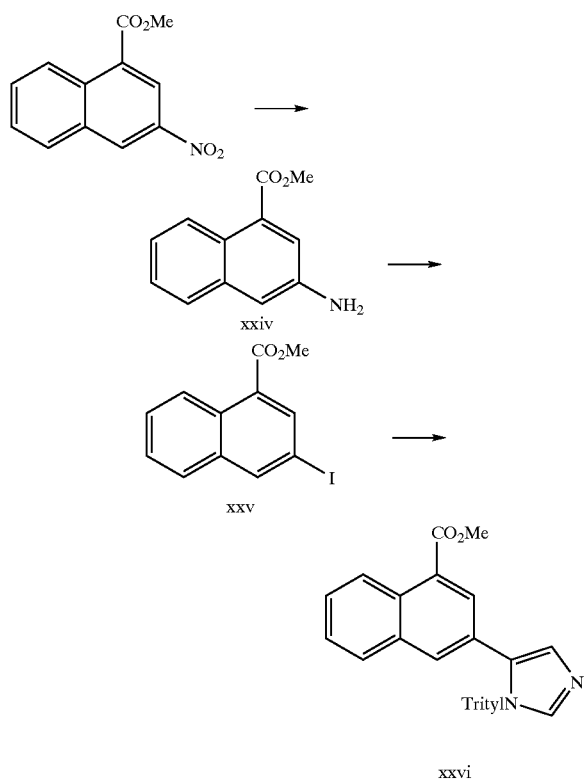

xxiv xxv xxvi

To a solution of methyl 3-nitro-2-naphthoate (purchased from TCI, 1.62 g, 7.0 mmol) in MeOH (20 mL) and EtOAc (20 mL) was added 10% Pd—C (0.16 g) and the mixture was stirred overnight under 1 atm H$_2$. Filtration and concentration of the filtrate afforded a brown solid (xxiv) that was dried under vacuum and used directly without further purification. To the above solid was added conc. HCl (3.1 mL), water (3.1 mL) and ice (6.5 g) and the resulting mixture was cooled in ice bath. While maintaining the reaction temperature below 5° C., NaNO$_2$ (0.51 g, 7.3 mmol) in water (3.3 mL) was added dropwise. After 30 min, a solution of KI (1.17 g, 7.00 mmol) in water (3 mL) was added and the reaction was stirred overnight at rt. The mixture was extracted with EtOAc (3×30 mL) and the combined organic extracts were sequentially washed with saturated aqueous NaHCO$_3$, Na$_2$S$_2$O$_3$ and NaCl solutions and dried (MgSO$_4$). Concentration followed by column chromatography (CH$_2$Cl$_2$:hexane/1:2) gave the desired naphthyl iodide xxv as a pale yellow solid (1.15 g).

A mixture of aryl iodide xxv (758 mg, 2.4 mmol), Ph$_3$As (151 mg, 0.5 mmol), CuI (92 mg, 0.48 mmol), Pd$_2$(dba)$_3$ (233 mg, 0.24 mmol) and 3-(tributylstannyl-1-tritylimidazole (1.46 g, 2.40 mmol; prepared according to xx J. Org. Chem. 1991, 56, 5739) in DMF (25 mL) was purged with nitrogen for 5 min and then heated to 65° C. for 4 h. The reaction mixture was concentrated under vacuum and partitioned between CH$_2$Cl$_2$ (200 mL) and aqueous sodium bicarbonate (100 mL). The organic layer was washed with brine and dried (MgSO$_4$). Concentration followed by column chromatography (CH$_2$Cl$_2$:MeOH/100:1) afforded the desired product xxvi as a gray solid (1.3 g).

Method G

This method illustrates the homologation of the A ring at the stage of one of the intermediates.

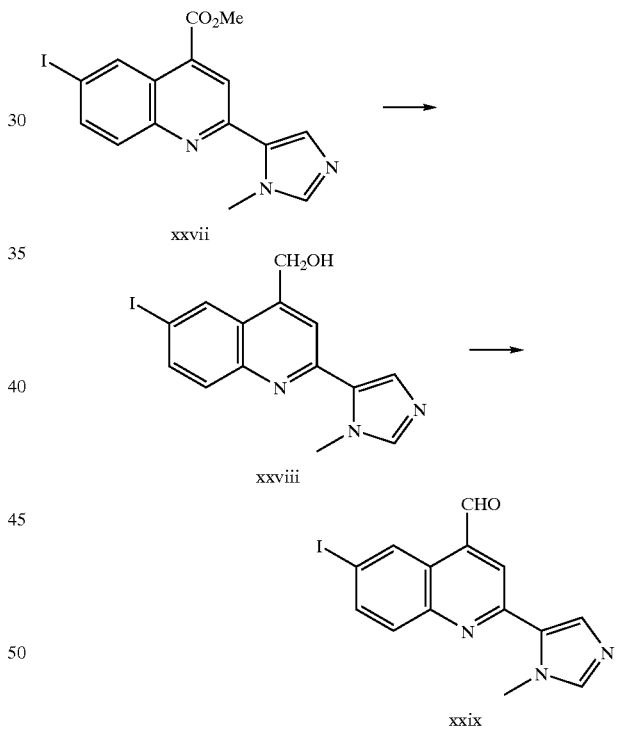

xxvii xxviii xxix

To a solution of xxvii (2.2 g, 5.6 mmol, prepared according to Method A from the iodoistatin) in THF (180 mL) at −78° C. was added dropwise DIBAL-H in toluene (1M, 22.4 mL, 22.4 mmol). The reaction was warmed to 0° C. After 3 h, saturated aqueous NH$_4$Cl (100 mL) was added and the mixture was extracted with CH$_2$Cl$_2$ (10×200 mL). The combined organic extracts were washed with brine and dried (MgSO$_4$). Removal of the solvent gave the desired alcohol xxviii as a white solid (2.0 g) which was carried on with out purification. To a solution of the alcohol (2.0 g, 5.5 mmol) in CH$_2$Cl$_2$ (200 mL) was added Dess-Martin reagent (4.3 g, 8.8 mmol) at room temperature. After 1 h, the reaction was quenched by adding saturated aqueous NaHCO$_3$ (100 mL)

and saturated aqueous Na₂S₂O₃ (100 mL). The organic layer was separated, washed with brine and dried (MgSO₄). Concentration, followed by column chromatography (CH₂Cl₂:MeOH/30:1) gave the corresponding aldehyde xxix as a yellow solid (1.7 g).

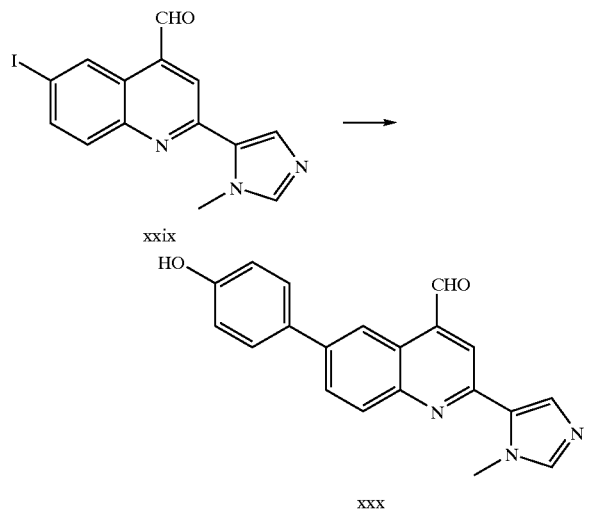

A mixture of aldehyde xxix (195 mg, 0.54 mmol), 4-hydroxyphenylboronic acid (172 mg, 0.81 mmol), PdCl₂(dppf)₂ (136 mg, 0.17 mmol) and potassium carbonate (344 mg, 2.5 mmol) in DMF (5 mL) was purged with nitrogen and heated to 65° C. overnight. The solvent was removed under vacuum and the resulting mixture was diluted with CH₂Cl₂ (100 mL). After washing with brine and drying (MgSO₄), removal of the solvent followed by column chromatography (CH₂Cl₂:MeOH/20:1) gave xxx as a yellow solid (56 mg), which was utilized without further purification.

Method H

This method exemplifies yet other types of homologation of the A ring at the stage of one of the intermediates.

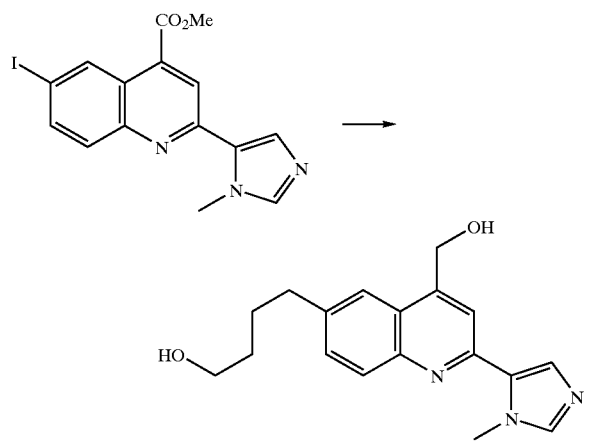

To a solution of the ester xxvii (1.2 g, 3.05 mmol, prepared according to Method A) in THF at −78° C. under nitrogen was added a 1.0 M solution of LiAlH₄ (4 mL, 4.0 mmol) in THF. The reaction was stirred for 1 h, quenched with water, and allowed to reach room temperature. The aqueous layer was extracted with EtOAc and the organic extract was washed with brine, dried over Na₂SO₄, and concentrated to give a solid. The crude product was dissolved in 50 mL of MeOH and treated with NaBH₄ (200 mg, 5.3 mmol). The reaction was stirred for 15 min, water was added, and the precipitate that formed was collected by filtration to give an intermediate iodo-alcohol (750 mg).

A mixture of the iodo alcohol (300 mg, 0.82 mmol), 3-butyn-1-ol (0.1 mL, 1.32 mmol), Pd(PPh₃)₄ (50 mg, 0.04 mmol), CuI (10 mg, 0.05 mmol), and triethylamine (1 mL) in 2 mL of DMF was stirred at 80° C. for 1 h. The reaction was cooled, diluted with water, and the precipitate that formed was collected by filtration. The crude product was dissolved in 10 mL of EtOH/MeOH (1:1) and was hydrogenated with 10% Pd/C (100 mg) at 45 psi H₂ for 3 days. The reaction was filtered and the solids were washed with CH₂Cl₂ and MeOH. The filtrate was concentrated to dryness to give the desired diol xxxi (100 mg). ¹H NMR (DMSO-d₆) δ 7.92 (d, J=8.5 Hz, 1H), 7.87 (s, 1H), 7.82 (s, 1H), 7.78 (d, J=1.4 Hz, 1H), 7.60 (dd, J=8.6, 1.8 Hz, 1H), 5.70 (br s, 1H), 5.00 (s, 2H), 4.43 (br s, 1H), 4.13 (s, 3H), 3.43 (t, J=6.4 Hz, 2H), 2.78 (t, J=7.6 Hz, 2H), 1.76–1.64 (m, 2H), 1.54–1.41 (m, 2H).

Additional examples of homologation of one of the intermediates.

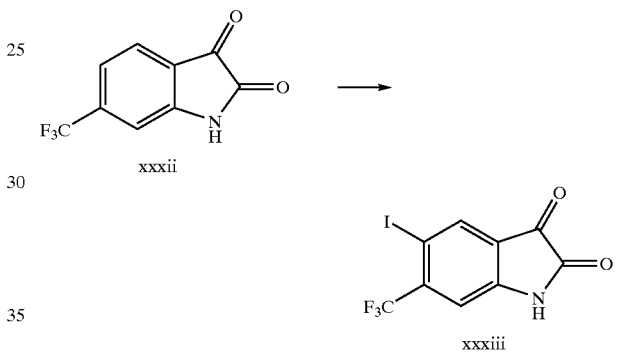

N-Iodosuccinimide (25.0 g, 119.5 mmol) was added to a stirred mixture of 6-trifluoromethylisatin (10.3 g, 47.8 mmol) and triflic acid (75 g) at 0° C. under nitrogen. The ice bath was removed and stirring at room temperature was continued for 7 h. The mixture was poured into ice-water and was extracted with EtOAc. The combined organic extracts were evaporated under reduced pressure and the residue was triturated with CHCl₃ to produce a yellow-orange solid. Filtration of the crude solid and purification by recrystallization from CHCl₃ gave 5-iodo-6-trifluoromethylisatin xxxiii (10.4 g) as an orange solid. ¹H NMR (DMSO-d₆) δ 7.17 (s, 1H), 8.08 (s, 1H), 11.27 (s, 1H); ms 340.0 (M−H).

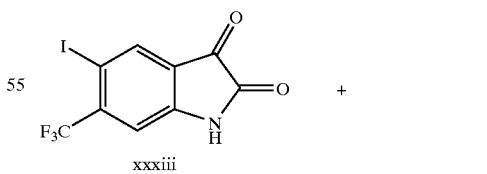

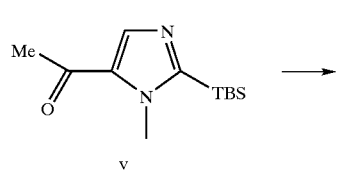

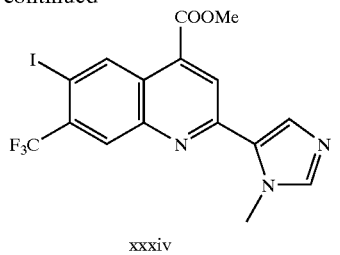

xxxiv

A mixture of 5-iodo6-trifluoromethylisatin (7.50 g, 22.0 mmol) and the methylketone v (5.24 g, 22.0 mmol, prepared as described in Method A) in EtOH (50 mL) was treated with a solution of KOH (4.93 g, 88.0 mmol) in 50 mL of water. The mixture was heated overnight at 85° C. and then cooled to 0° C. 1N HCl (88 mL) was added to the mixture dropwise while a precipitate was formed. The precipitate was collected, rinsed with ice-water and dried under vacuum, which gave crude acid (8.0 g): $^1$H NMR (DMSO-d$_6$) δ 4.14 (s, 1H), 7.98 (s, 1H), 8.03 (s, 1H), 8.41 (s, 1H), 8.44 (s, 1H), 9.42 (s, 1H); ms 448.0 (M+H$^+$).

Sulfuric acid (3.5 mL) was added to a stirred solution of the crude acid (8.0 g) in MeOH (120 mL), and the mixture was refluxed for 48 h. The resulting mixture was cooled and a precipitate was collected. Rinsing with cold methanol gave the corresponding methyl ester xxxiv (5.84 g in two steps) as a pure off-white solid. $^1$H NMR (DMSO-d$_6$) δ 4.04 (s, 1H), 4.29 (s, 1H), 8.56 (s, 1H), 8.57 (s, 1H), 8.65 (s, 1H), 9.08 (s, 1H), 9.39 (s, 1H); ms 462.0 (M$^+$H$^+$).

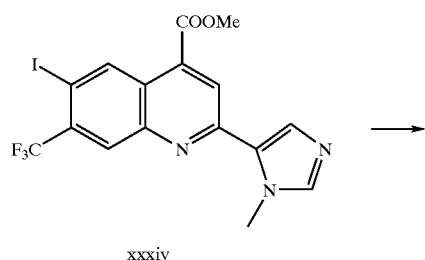

xxxiv

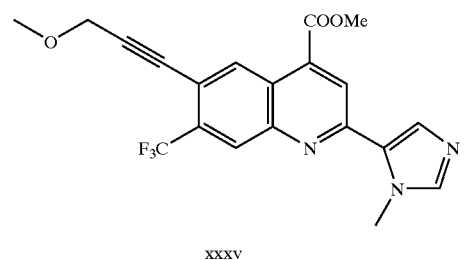

xxxv

To a mixture of the 6-iodo-7-trifluoromethyl methyl ester xxxiv (615 mg, 1.33 mmol), PdCl$_2$(PPh$_3$)$_2$ (234 mg, 0.33 mmol), and CuI (38 mg, 0.15 mmol) in 1:1 DMF-Et$_3$N (16 mL), methyl propargyl ether (0.34 mL, 4.02 mmol) was added at room temperature under nitrogen. Stirring at room temperature was continued for 4.5 h. The mixture was concentrated and the residue was dissolved in CH$_2$Cl$_2$. The CH$_2$Cl$_2$ solution was washed with water and brine, dried, and evaporated. Flash chromatography of the residue over silica gel, using 1:4:5 MeOH-EtOAc-hexane, gave the crude methyl ether xxxv (300 mg).

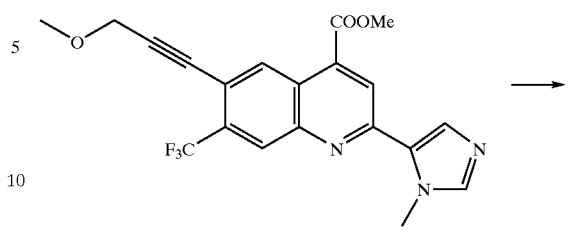

xxxv

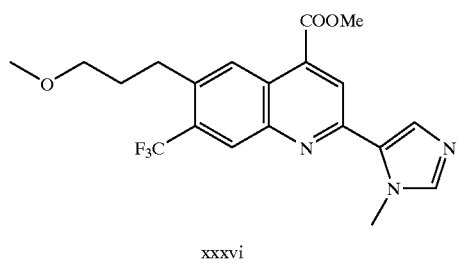

xxxvi

The crude methyl ether xxxv (300 mg) in MeOH (15 mL) was treated with 10% Pd/C (158 mg) and hydrogenated overnight at room temperature. The mixture was filtered and evaporated to give the crude saturated methyl ether xxxvi (125 mg).

Another example of homologation of the A ring of one of the intermediates is described in the following steps:

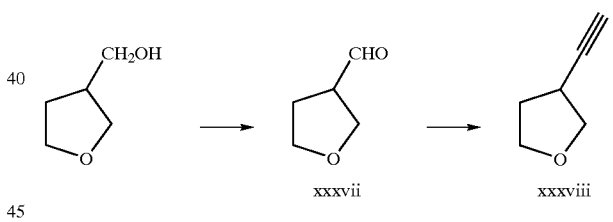

xxxvii  xxxviii

To a mixture of tetrahydro-3-furanmethanol (Aldrich Chemical Co., 3.63 g, 35.6 mmol), N-methylmorpholine oxide (6.3 g, 53.8 mmol) and 4A molecular sieves (18 g) in CH$_2$Cl$_2$ (70 mL) at 0° C. was added TPAP (0.63 g, 1.8 mmol). After 2 h at rt, the reaction mixture was poured on the top of a short column and the product was eluted with ether (3×50 mL). Concentration followed by column chromatography (EtOAc:Hexane/1:2 to 1:1) afforded the aldehyde xxxvii (1.2 g) by careful concentration under reduced pressure at 0° C. To a solution of LDA [7.5 mmol, prepared from 2.5M n-BuLi (3.0 mL, 7.5 mmol) and diisopropylamine (1.26 mL, 9 mmol)] in THF (30 mL) at −78° C. was added 2 M TMSCHN$_2$ (3.75 mL, 7.5 mmol). After 30 min at −78° C., the aldehyde xxxvii (0.5 g, 5 mmol) was added and the mixture was warmed to room temperature over 2 h. Then water (20 mL) was added and the mixture was extracted with ethyl ether (2×30 mL). The combined organic layers were dried and removal of the solvent by careful concentration under reduced pressure at 0° C. gave 3-ethynyltetrahydrofuran xxxvii as a colorless liquid.

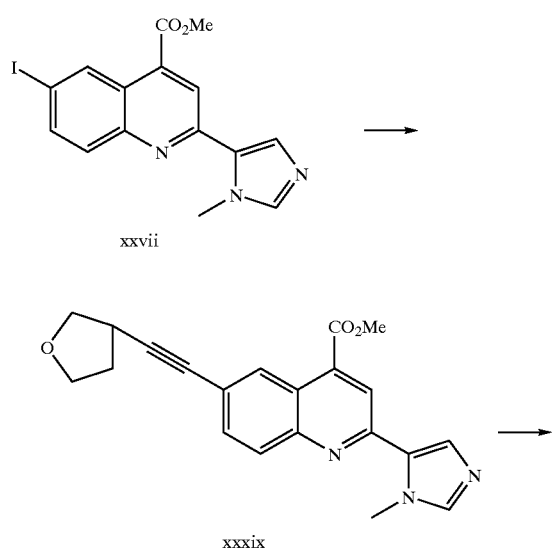

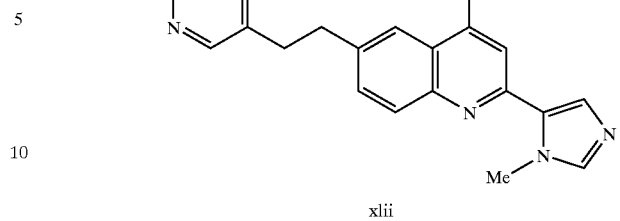

Ester xlii was prepared by the methodology of Method H. 3-Ethynylpyridine was obtained from Aldrich Chemical Co. $^1$H NMR (CDCl$_3$) δ: 8.18 (d, J=8.6 Hz, 1H), 8.00 (s, 1H), 7.62 (s, 1H), 7.53 (dd, J=1.8, 8.5, 1H), 7.50 (m, 1H), 7.21 (m, 1H), 4.20 (s, 3H), 4.05 (s, 3H), 3.16 (m, 2H), 3.06 (m, 2H).

Method I

This method describes additional homologation strategies for the A ring of various intermediates.

Compound xl was prepared by the methodology of Method H, using iodoester xxvii and 3-ethynyltetrahydrofuran. $^1$H-NMR (CDCl$_3$) δ: 159–1.66 (m, 1H), 1.84–1.88 (m, 2H), 2.08–2.18 (m, 1H), 2.23–2.37 (m, 1H), 2.79–2.93 (m, 2H), 3.44 (t, J=7.7 Hz, 1H), 3.71–3.81 (m, 1H), 3.89–3.98 (m, 2H), 4.09 (s, 3H), 4.29 (s, 3H), 7.62 (d, J=8.6 Hz, 1H), 7.73 (s, br, 2H), 8.03 (d, J=8.6 Hz, 1H), 8.20 (s, 1H), 8.55 (s, 1H). ES-MS: m/z: 366 (M+1)$^+$.

A solution of the ester xxvii (500 mg, 1.27 mmol), acrylonitrile (0.2 mL, 3.03 mmol), Pd(PPh$_3$)$_4$ (50 mg, 0.04 mmol), and triethylamine (0.5 mL) in 4 mL of DMF was stirred at 90° C. for 18 h. The reaction mixture was cooled to room temperature, diluted with water, and the precipitate was collected by filtration. The residue was purified by chromatography (silica, CH$_2$Cl$_2$/MeOH, 96:4) to obtain the desired cyano ester xlii (250 mg, 62%). A suspension of this ester xliii (250 mg, 0.78 mmol) and 10% Pd/C (50 mg) in 10 mL of EtOH/MeOH (1:1) was hydrogenated at 45 psi for 18 h. The catalyst was filtered, washed with CH$_2$Cl$_2$ and MeOH, and the filtrate was concentrated to dryness to give the desired product as a solid (250 mg, quantitative). $^1$H NMR (DMSO-d$_6$) δ 8.36 (d, J=1.4 Hz, 1H), 8.24 (s, 1H), 8.04 (J=8.6 Hz, 1H), 7.96 (s, 1H), 7.88 (s, 1H), 7.79 (dd, J=8.6, 1.8 Hz, 1H), 4.13 (s, 3H), 4.02 (s, 3H), 3.12 (t, J=7.2 Hz, 2H), 2.94 (t, J=6.7 Hz, 2H).

Another example of the methodology illustrated by Method I:

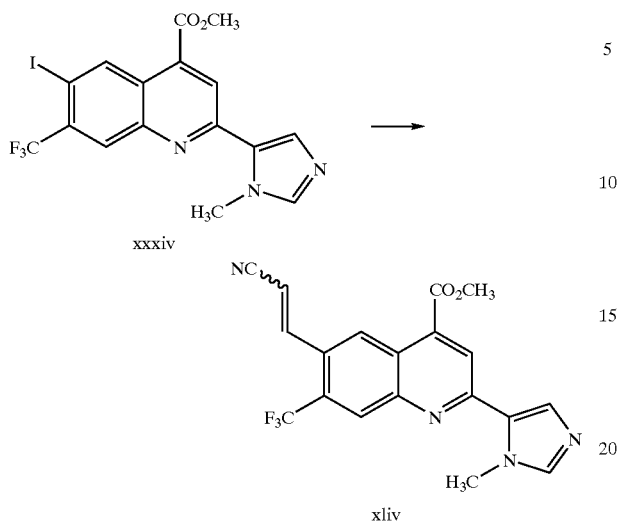

To a mixture of 6-iodo-7-trifluoromethyl methyl ester xxxiv (661 mg, 1.43 mmol, prepared in Method H), P(o-tol)$_3$ (872 mg, 2.87 mmol), NaOAc (259 mg, 3.15 mmol), and Pd(OAc)$_2$ (322 mg, 1.43 mmol) in DMF (20 mL), acrylonitrile (5.0 mL, 76 mmol) was added at room temperature under nitrogen. The mixture was stirred and heated to 115° C. for 6 h. The mixture was cooled to room temperature and concentrated. The residue was dissolved in CH$_2$Cl$_2$, washed with water and brine, dried, and evaporated. Flash chromatography of the residue over silica gel, using 1:4:5 MeOH-EtOAc-hexane, gave a (Z) and (E) mixture of the unsaturated nitrile xliv (253 mg) as a solid: $^1$H NMR (DMSO-d$_6$) δ 4.03 (s, 1.2H), 4.06 (s, 1.8H), 4.17 (s, 1.2H) 4.18 (s, 1.8H), 6.28 (d, J=12 Hz, 0.4H), 6.63 (d, J=17 Hz, 0.6H), 7.78 (d, J=12 Hz, 0.4H), 7.87 (d, J=17 Hz, 0.6H), 7.96 (s, 1H), 8.06 (s, 1H), 8.48 (s, 1H), 8.52 (s, 1H), 8.89 (s, 0.6H), 9.13 (s, 0.4H); MS: 387.0 (M$^+$H$^+$).

Method J

This method describes additional methodology for elaboration of the A ring of one of the intermediates.

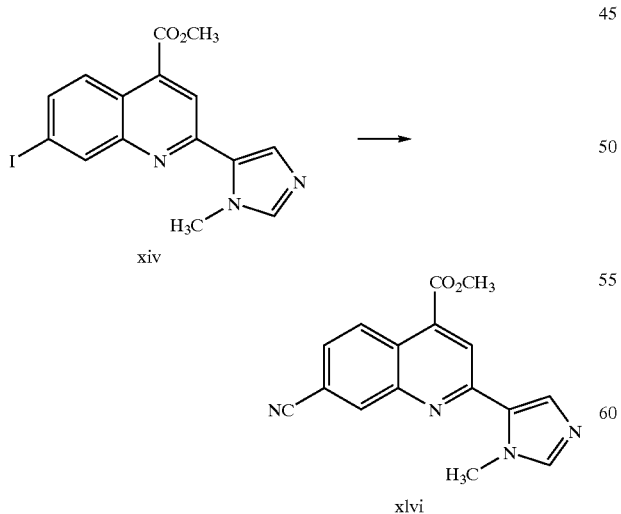

To a solution of the 7-iodoquinoline (440 mg, 1.12 mmol, prepared as in Method A) in dry, degassed acetonitrile, (28 mL) was added finely ground and dried NaCN (110 mg, 2.24 mmol), CuI (21.3 mg, 0.112 mmol), and Pd(PPh$_3$)$_4$ (65 mg, 0.056 mmol) under nitrogen. The mixture was stirred and heated to reflux for 1.5 h. The reaction was diluted with ethyl acetate, filtered and the filtrate was evaporated under reduced pressure. The residue was purified by chromatography: (2.5% MeOH/CH$_2$Cl$_2$,) to yield xlvi (161.4 mg). $^1$H NMR (CDCl$_3$) δ 4.08 (s, 3H), 4.20 (s, 3H), 7.46 (ddd J=2.8, 3.8, 5.1 Hz 1H), 7.65 (m, 1H), 8.32 (s, 1H), 8.39 (s, 1H), 8.86 (d, J=8.8 Hz, 1H).

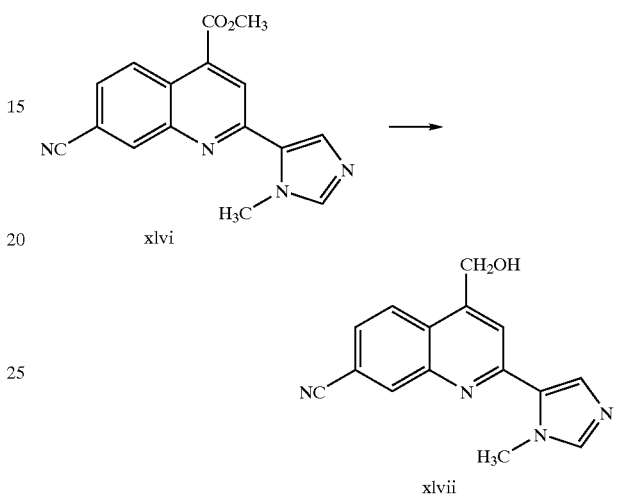

To a stirred solution of the 7-cyanoquinoline xlvi (119 mg, 0.41 mmol) in THF (20 mL) was added LiBH$_4$ (0.31 mL, 0.61 mmol, 2.0M/THF). The resulting solution was refluxed for 0.5 h, poured into water, extracted with ethyl acetate and washed with dilute HCl. The aqueous phase was basified and re-extracted with ethyl acetate. The combined ethyl acetate extracts were combined and reduced to dryness to give 34 mg of xlvii as a crude solid product, which was used in the next step without further purification. $^1$H NMR (DMSO-d$_6$) δ 4.13 (s, 3H), 5.02 (s, 2H), 7.81–7.89 (m, 3H), 8.06 (s, 1H), 8.21 (d, J=12 Hz, 1H), 8.53 (s, 1H). MS 265.1.0 (M+H$^+$).

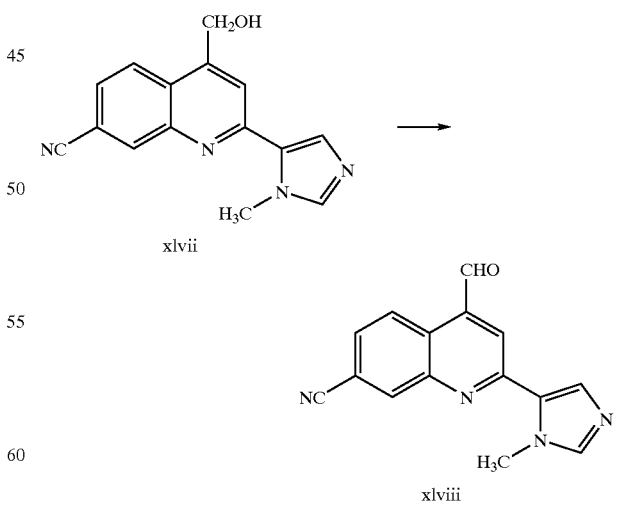

To a stirred solution of the crude alcohol xlvii (34 mg, 0.129 mmol) in CH$_2$Cl$_2$ (10 mL) was added the Dess-Martin periodinane reagent (73 mg, 0.172 mmol). The solution was stirred for 1 h at room temperature, poured into water, extracted with CH$_2$Cl$_2$ and washed with 10% aqueous Na$_2$S$_2$O$_3$, saturated aqueous NaHCO$_3$, and brine. The organic solution was dried over Na$_2$SO$_4$. The residue was chromatographed on silica gel (5% MeOH/CH$_2$Cl$_2$) to provide the corresponding aldehyde xlviii, 34.8 mg (two steps). $^1$H NMR (CDCl$_3$) δ 4.25 (s, 3H), 7.70 (s, 1H), 7.80 (d, J=8 Hz, 1H), 7.88 (s, 1H), 8.21 (s, 1H), 8.46 (s, 1H), 9.12 (d, J=8.8 Hz, 1H).

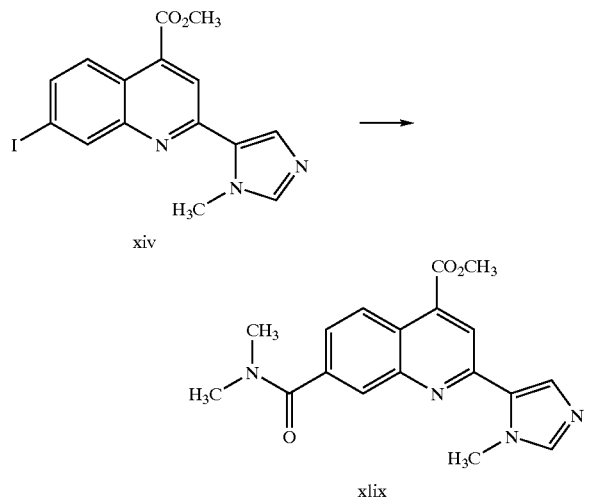

To a solution of ester xlv (430 mg, 1.09 mmol) in DMF (5 mL) at rt was added triethylamine (0.35 mL, 2.5 mmol) followed by dimethylamine (2.2 mL of a 2.0 M solution in THF, 4.4 mmol). The reaction mixture was gently purged with carbon monoxide for 5 min, Pd(PPh$_3$)$_4$ (115 mg, 0.10 mmol) was added and the resulting mixture was stirred under 1 atm of carbon monoxide at rt for 5 h and then at 70° C. for 3 h. The reaction mixture was cooled to rt and concentrated under vacuum. Chromatography (9:1/CH$_2$Cl$_2$:MeOH) of the residue afforded 173 mg of xlix sufficiently pure for further use. $^1$H NMR (CDCl$_3$) δ: 8.76 (d, J=8.7, 1H), 8.24 (s, 1H), 8.12 (s, 1H), 7.74 (s, 1H), 7.63–7.60 (m, 2H), 4.19 (s, 3H), 4.07 (s, 3H), 3.18 (s, 3H), 3.05 (s, 3H).

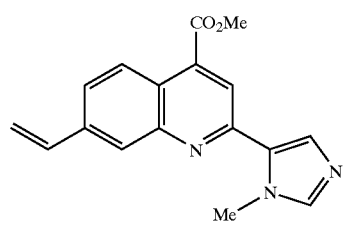

To a solution of ester xlv (225 mg, 0.57 mmol) in DMF (2 mL) was added AsPh$_3$ (15 mg, 0.05 mmol), CuI (11 mg, 0.06 mmol) and Pd$_2$dba$_3$ (22 mg, 0.02 mmol). The reaction mixture was purged with nitrogen for 5 min, vinyltributyltin (0.34 mL, 1.2 mmol) was added and the reaction mixture was heated to 65° C. for 3 h. After pouring onto water and saturated aqueous NaHCO$_3$ (15 mL each), the mixture was extracted with EtOAc (3×20 mL). The combined organic extracts were washed with saturated aqueous KF (2×20 mL), dried (MgSO$_4$) and concentrated. Chromatography (25:1/CH$_2$Cl$_2$:MeOH) provided 140 mg of product I. $^1$H NMR (CDCl$_3$) δ: 866 (d, J=8.8 Hz, 1H), 8.15 (s, 1H), 7.99 (s, 1H), 7.71 (d, J=8.8 Hz, 1H), 6.91 (dd, J=11.0, 17.6 Hz, 1H), 5.99 (d, J=17.6 Hz, 1H), 5.46 (d, J=11.0, 1H), 4.21 (s, 3H), 4.06 (s, 3H).

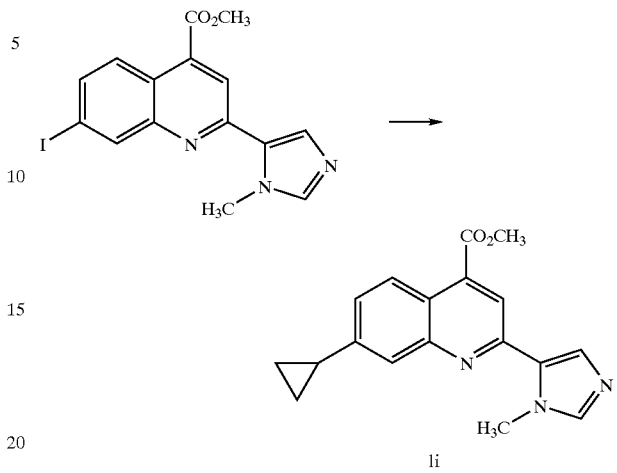

Magnesium turnings (240 mg, 9.95 mmol) were placed in a 3-neck flask containing dry THF (2 mL) and the flask was placed in a bath at 50° C. Cyclopropylbromide (0.79 mL, 10 mmol) was added dropwise under gentle reflux and the mixture was heated to reflux for 1 h. After cooling to rt, the mixture was added to a solution of zinc chloride in THF (1M, 20 mL, 10 mmol) at 0° C. and it was stirred at rt for 2 h. A solution of iodide xlv (393 mg, 1.0 mmol) in THF (5 mL) was added, followed by PdCl$_2$(dppf)$_2$ (41 mg, 0.05 mmol) and the resulting mixture was stirred overnight. The reaction was quenched by addition of saturated aqueous NH$_4$Cl (10 mL) and saturated EDTA-sodium aqueous solution (10 mL). The resulting mixture was extracted with CH$_2$Cl$_2$ (3×30 mL), washed with brine and dried (MgSO$_4$). Concentration followed by column chromatography (CH$_2$Cl$_2$:MeOH/30:1) gave the desired product li as a yellow solid (290 mg). $^1$H-NMR (CDCl$_3$) δ: 0.91–0.94 (m, 2H), 1.13–1.16 (m, 2H), 2.12–2.15 (m, 1H), 4.08 (s, 3H), 4.28 (s, 3H), 7.37 (d, J=8.8 Hz, 1H), 7.76 (s, 1H), 7.82 (s, br, 1H), 7.95 (s, br, 1H), 8.13 (s, 1H), 8.64 (d, J=8.8 Hz). ES-MS: m/z: 308 (M+1)$^+$.

Method K

This method describes additional methodology for the elaboration of the A ring of one of the intermediates.

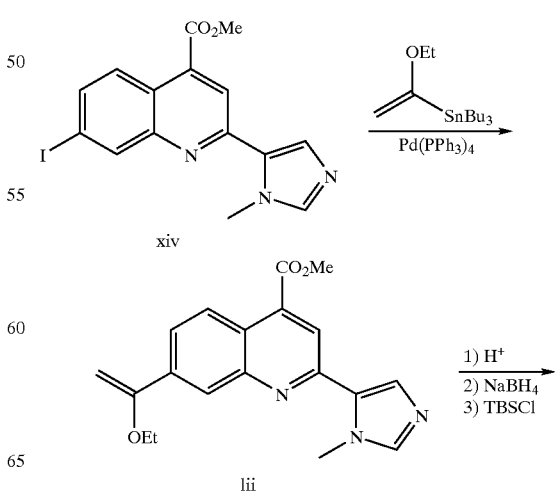

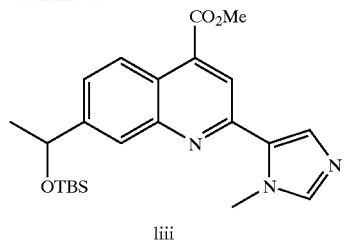

liii

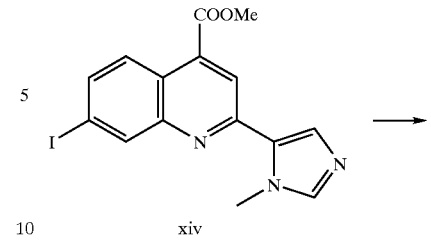

xiv

To a stirred solution of xlv (500 mg, 1.27 mmol) in dioxane (30 mL) under an atmosphere of nitrogen was added 1-(ethoxyvinyl)tri-n-butyl stannane (482 mg, 1.33 mmol) and (Ph3P)4Pd (catalytic amount, ~5 mg) and the mixture was heated at 100° C. for 12 h. Additional amounts of 1-(ethoxyvinyl)tri-n-butylstannane (482 mg, 1.33 mmol) and (Ph3P)4Pd (catalytic amount, ~5 mg) were added and the mixture stirred for 12 h at 100° C. The mixture was concentrated to dryness and flash chromatography (gradient elution $CH_2Cl_2$ to $CH_2Cl_2$:MeOH 98:2) afforded the desired product lii (350 mg). $^1$H NMR (CDCl$_3$): δ 8.52 (d, J=8 Hz, 1H), 8.15 (s, 1H), 7.99 (s, 1H), 8.71 (d, J=8 Hz, 1H), 7.60 (s, 1H), 7.44 (s, 1H), 4.80 (s, 1H), 4.29 (s, 1H), 4.07 (s, 3H), 3.93 (s, 3H), 3.90 (q, J=6.5 Hz, 2H), 1.42 (t, J=6.5 Hz, 3H); ESI-MS m/z 338.1 (100, M+H$^+$).

To a stirred solution of quinoline lii (350 mg, 1.0 mmol) in dioxane (10 mL) was added conc. sulfuric acid (0.5 mL). The mixture was stirred overnight at room temperature and quenched with saturated aqueous sodium bicarbonate. Dichloromethane was added and the organic phase was collected, dried (Na$_2$SO$_4$), filtered and concentrated in vacuo to afford an intermediate ketone (128 mg). $^1$H NMR (CDCl$_3$) δ 8.80 (d, J=8 Hz, 1H), 8.61 (s, 1H), 8.28 (s, 1H), 8.14 (d, J=8 Hz, 1H), 7.78 (s, 1H), 7.60 (s, 1H), 4.12 (s, 3H), 4.05 (s, 3H), 2.80 (s, 3H); ESI-MS m/z 310.1 (100, M+H$^+$).

To a stirred solution of intermediate ketone (128 mg, 0.41 mmol) in anhydrous methanol (5 mL) at 0° C. was added sodium borohydride (31 mg, 0.82 mmol) under nitrogen and the mixture was stirred for 2 b, then quenched by the addition of saturated aqueous ammonium chloride (10 mL) and diluted with dichloromethane (60 mL). The organic phase was collected, washed with brine, dried (MgSO$_4$), filtered and concentrated in vacuo. Flash chromatography (gradient elution CH$_2$Cl$_2$ 99:1 to CH$_2$Cl$_2$:MeOH 97:3) afforded an intermediate alcohol (115 mg, 90%). $^1$H NMR (CDCl$_3$) δ 8.63 (d, J=8 Hz, 1H), 8.08 (s, 1H), 7.98 (s, 1H), 7.44–7.63 (m, 3H), 5.04 (q, J=7 Hz, 1H), 4.14 (s, 3H), 4.07 (s, 3H), 1.60 (d, J=7 Hz, 3H); ESI-MS m/z 312.2 (100, M+H$^+$).

To a stirred solution of the intermediate alcohol (115 mg, 0.36 mmol) in DMF (5 mL) under an atmosphere of nitrogen was added imidazole (63 mg, 0.93 mmol) and tert-butyldimethylsilyl chloride (444 μl of a 1.0 M solution in THF, 0.44 mmol). The mixture was stirred at room temperature for 12 h then concentrated in vacuo. The residue was taken up in dichloromethane and washed with saturated aqueous ammonium chloride and brine. The organics were dried (MgSO$_4$), filtered and concentrated in vacuo. Flash chromatography (gradient elution CH$_2$Cl$_2$ to CH$_2$Cl$_2$:MeOH 97.5:2.5) afforded liii (127 mg, 84%). $^1$H NMR (CD$_3$OD) δ 8.60 (d, J=8 Hz, 1H), 8.08 (s, 1H), 7.93 (s, 1H), 7.45–7.60 (m, 3H), 4.51 (q, J=6 Hz, 1H), 4.12 (s, 3H), 3.98 (s, 3H), 1.40 (d, J=6 Hz, 3H), 0.82 (s, 9H), 0.02 (s, 3H), –0.04 (s, 3H); ESI-MS m/z 426.2 (100, M+H$^+$).

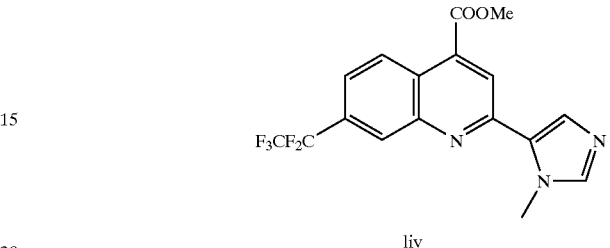

liv

Copper powder (ca. 1 micron, 0.31 g, 4.82 mmol), and DMSO (4 mL) were charged to a resealable pressure tube and cooled to 0° C. Pentafluoroethyl iodide(0.3 mL, 626 mg, 2.54 mmol) was added and the mixture was heated at 110° C.–120° C. for 4 h. After cooling to room temperature, the blue-green reagent was removed and added to intermediate xlv (237 mg, 0.605 mmol). The mixture was heated to 65° C. for 1 h. The cooled mixture was poured into 1N HCl (20 mL) and THF (20 mL). The organic phase was separated, washed with water, brine, dried and evaporated. Flash chromatography of the residue over silica gel, using 1:4:5 MeOH-EtOAc-hexane, gave the pentafluoroethyl compound liv (180 mg) as a pure solid. $^1$H NMR (DMSO-d$_6$) δ 4.03 (s, 3H), 4.15 (s, 3H), 7.88 (d, J=9.4 Hz, 1H), 7.92 (s, 1H), 7.98 (s, 1H), 8.37 (s, 1H), 8.43 (s, 1H), 8.74 (d, J=9.4 Hz, 1H); ms 386.1 (M$^+$H$^+$).

Method L

This method describes the synthesis of compounds in which the B ring is linked to the remainder of the molecule via a nitrogen atom.

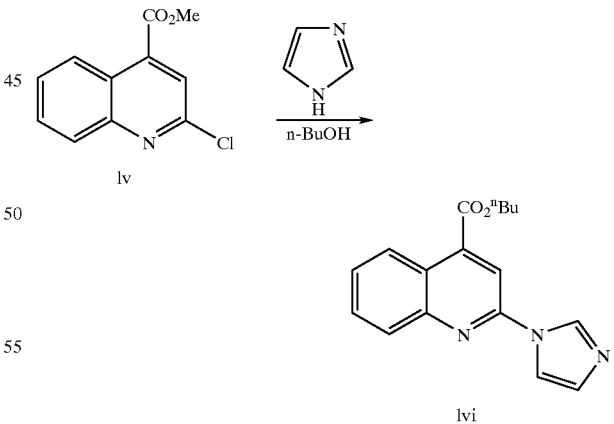

lv lvi

A stirred solution of 4-carbomethoxy quinolin-2-one (prepared as shown in Method D (1.76 g, 9 mmol), POCl$_3$ (4.6 g, 30 mmol) in toluene (40 mL) was heated at reflux for 2 h then allowed to cool to room temperature and poured into ice water (50 mL). The mixture was extracted with ethyl acetate (3×50 mL). The organics were combined, washed with water, brine, dried (MgSO$_4$) and concentrated in vacuo to afford the desired 2-chloro-4-carbomethoxyquinoline lv (1.50 mg). $^1$H NMR (DMSO-d$_6$) δ 8.54 (d, J=8 Hz, 1H), 8.03–8.06 (m, 1H), 7.89–7.94 (m, 2H), 7.75–7.77 (m, 1H), 3.98 (s, 3H); ESI-MS m/z 222.1 (100, M+H$^+$).

To a stirred solution of 2-chloro-4-carbomethoxyquinoline lv (346 mg, 1.5 mmol) in anhydrous n-butanol (5 mL) was added imidazole (212 mg, 3 mmol) and the mixture was heated at reflux for 48 h then imidazole (212 mg, 3 mmol) was added. The mixture was heated at reflux for a further 12 h then cooled to room temperature and concentrated in vacuo. Flash chromatography afforded the desired product lvi as the n-butyl ester (152 mg, 34%); $^1$H NMR (CDCl$_3$) δ 8.56 (d, 1H, J=8 Hz), 8.56 (s, 1H) 8.10 (d, 1H, J=8 Hz), 8.01 (s, 1H), 7.88 (s, 1H), 7.93–7.83 (m, 1H) 7.65–7.67 (m, 1H) 7.28 (s, 1H) 4.51 (t, J=8 Hz, 3H), 1.82–1.88 (m, 2H) 1.50–1.56 (m, 2H), 1.03 (t, J=8 Hz, 3H) 2.96 (s, 3H); ESI-MS m/z 296.1 (100, M+H$^+$).

Method M

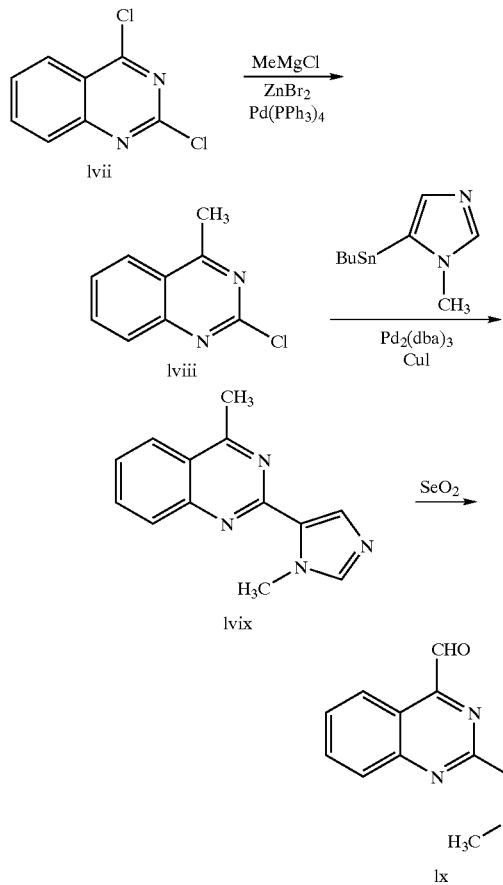

To a stirred solution of methyl magnesium chloride (1.6 mL of a 3.0 M solution in THF, 4.8 mmol) in anhydrous THF (16 mL) at −78° C. under an atmosphere of nitrogen was added a solution of zinc bromide (1.08 g, 4.8 mmol) in THF (5 mL). The mixture was stirred at −78° C. for 1 h then warmed to room temperature whereupon a mixture of tetrakis(triphenylphosphine)palladium (0) (228 mg, 0.20 mmol) and 2,4-dichloroquinazoline lvii (800 mg, 0.40 mmol, see Butler, et al., *J. Chem. Soc.* 1959, 1512) were added as a solution in THF (11 mL). The mixture was then heated at 50° C. for 12 h then cooled to 0° C. and quenched by the addition of saturated aqueous ammonium chloride and diluted with ethyl acetate. The organics were collected, dried (Na$_2$SO$_4$), filtered and concentrated in vacuo. Flash chromatography (EtOAc:hexane 1:5 afforded the desired product lviii as a white solid (410 mg, 57%). $^1$H NMR (CDCl$_3$) δ 8.07 (d, J=9 Hz, 1H), 7.88–7.92 (m, 2H), 7.61–7.64 (m, 1H) 2.93 (s, 3H); ESI-MS m/z 179.1 (100, M+H$^+$).

A stirred solution of 2chloro 4-methyl quinazoline lviii (250 mg, 1.4 mmol), 1-methyl-(5-tri-n-butylstannyl) imidazole (523 mg, 1.4 mmol, Gaare, et al., *Acta Chem. Scand.*, 47:57 (1993)), triphenyl arsine (43 mg, 0.14 mmol), Pd$_2$(dba)$_3$ (63 mg, 0.07 mmol) and CuI (26 mg) in DMF (5 mL) was purged with nitrogen gas for 5 min. then stirred under nitrogen at 60° C. for 12 h. The mixture was allowed to cool to room temperature then diluted with ethylacetate and water. The organics were collected, washed with water, saturated aqueous KF and water then dried (Na$_2$SO$_4$), filtered and concentrated in vacuo. Flash chromatography (gradient elution CH$_2$Cl$_2$:MeOH 99:1 to 96:4) afforded the desired product lix as a white solid (243 mg, 77%). $^1$H NMR (CDCl$_3$) δ 8.05–8.10 (m, 2H), 7.79–7.98 (m, 2H) 7.50–7.66 (m, 2H) 4.22 (s, 3H) 2.96 (s, 3H); ESI-MS m/z 225.2 (100, M+H$^+$).

To a stirred solution of quinazoline lvix (78 mg, 0.34 mmol) in 1,4-dioxane (2 mL) was added selenium dioxide (54 mg, 0.48 mmol) and the mixture was heated at reflux for 150 min. The mixture was allowed to cool to room temperature, filtered and concentrated to approx. 5 mL. Flash chromatography (CH$_2$Cl$_2$:MeOH 95:5) afforded the aldehyde which was concentrated to 10 mL volume then water (2 mL) and ethanol (10 mL) were added. The mixture was again concentrated to 5 mL and ethanol (10 mL) was added and the mixture again concentrated to 2 mL. The solution of aldehyde lx was taken on directly to the following reaction.

Method N

The following example is a variation of Method M in which the B ring is attached to the central ring via a nitrogen atom.

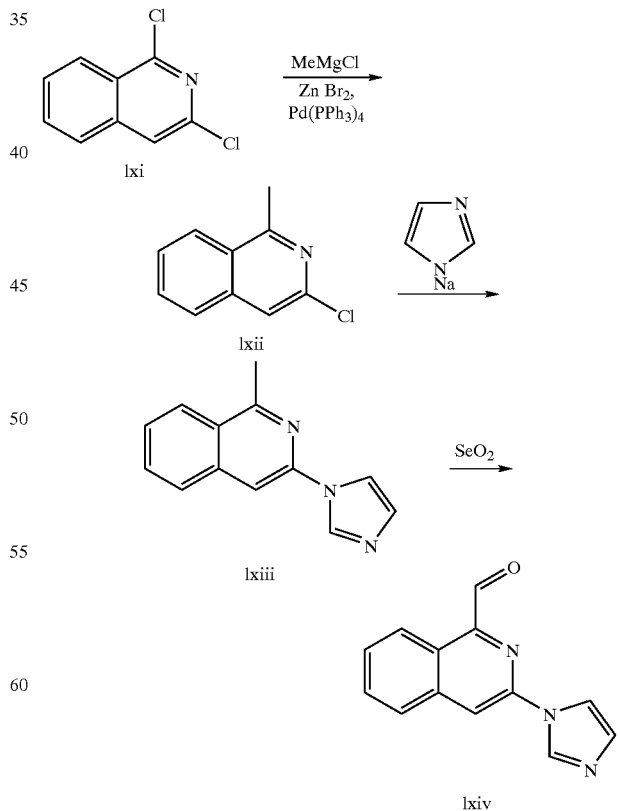

To a stirred solution of methyl magnesium chloride (1.62 mL of a 3.0M solution in THF, 4.8 mmol) in THF (16 mL)

at −78° C. under nitrogen was added zinc bromide (1.09 g, 4.8 mmol) in THF (5 mL). The mixture was stirred at −78° C. for 1 h and then allowed to warm to room temperature whereupon tetrakis(triphenylphosphine) palladium (233 mg, 0.02 mmol) and 1,3 dichloroisoquinoline lxi (800 mg, 4.0 mmol, Robinson, *J. Am. Chem. Soc.*, 1958, 80, 5481) were added. The mixture was stirred at 50° C. for 12 h then cooled to 0° C. Saturated aqueous ammonium chloride (10 mL) and ethyl acetate (60 mL) were added and the organics separated, dried ($Na_2SO_4$), filtered and concentrated in vacuo. Flash chromatography (hexane:EtOAc 7:1) afforded the desired product lxii (597 mg, 84%). $^1$H NMR ($CDCl_3$) δ 8.03–8.05 (m, 1H), 7.52–7.55 (m, 4H) 2.92 (s, 3H); GCMS m/z 177 (100, M$^+$).

To a stirred suspension of sodium hydride (159 mg, 6.6 mmol) in DMF (2 mL) was added imidazole (562 mg, 8.2 mmol) in DMF (2 mL) and the mixture was allowed to stir at room temperature for 2 h whereupon a solution of 3-chloro-1-methyl isoquinoline lxii (293 mg, 1.6 mmol) in DMF (2 mL) was added. The mixture was then stirred at 120° C. for 48 h, cooled and quenched by the addition of saturated aqueous ammonium chloride (20 mL) and diluted with dichloromethane (50 mL). The organics were collected, dried ($Na_2SO_4$), filtered and concentrated in vacuo. Flash chromatography (gradient elution $CH_2Cl_2$:MeOH 99:1 to 95:5) afforded the desired product lxiii (106 mg, 32%). $^1$H NMR ($CDCl_3$) δ 8.22 (s, 1H), 8.16 (s, 1H) 7.80–7.82 (m, 1H), 7.62–7.67 (m, 2H), 7.51–7.60 (m, 1H) 7.44 (s, 1H) 7.21 (s, 1H), 2.97 (s, 3H).

To a stirred solution of isoquinoline lxiii (165 mg, 0.78 mmol) in 1,4-dioxane (5 mL) was added selenium dioxide (438 mg, 3.9 mmol) and the mixture was heated at reflux for 14 h then cooled to room temperature, filtered and the filtrate concentrated to approx. 5 mL. Flash chromatography ($CH_2Cl_2$:MeOH) afforded the desired product lxiv as indicated by mass spectrometry.

Method O

This method describes additional ways of modifying the A ring of one of the intermediates.

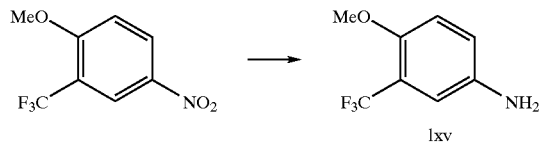

To a stirred solution of 4-nitro-2-trifluoromethylanisole (20.4g, 92.3mmol, Aldrich) in MeOH (205 mL) was added Pd·C (612 mg) followed by a balloon of $H_2$ gas. The reaction was stirred overnight, filtered through Celite to give, after solvent removal, the aniline lxv (17.6 g). $^1$H NMR ($CDCl_3$) δ 3.54 (br s, 2H), 3.82 (s, 3H), 6.80 (dd, J=4, 12 Hz, 1H), 6.85 (d, J=12 Hz, 1H), 6.91 (d, J=4 Hz, 1H)

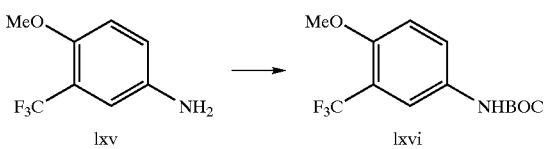

Di-tert-butyl dicarbonate (29.0 g, 0.133 mol) was added to a solution of 4-methoxy-3-trifluoromethylaniline lxv (23.1 g, 0.12 mol) in THF (75 mL). The resulting solution was refluxed overnight, cooled and the solvent removed under reduced pressure, the resulting black oil was chromatographed (hexane/ethyl acetate as eluant) to give 24.6 g of the product lxvi. $^1$H NMR (DMSO-$d_6$) δ 1.48 (s, 9H), 3.82 (s, 3H), 7.17 (d, J=12 Hz, 1H), 7.61 (d, J=12 Hz, 1H), 7.81 (s, 1H), 9.42 (s, 1H).

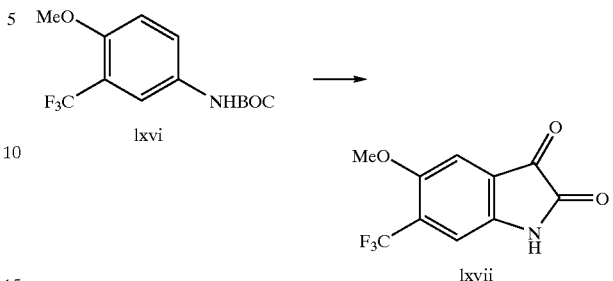

To a stirred solution of intermediate lxvi (18.5 g, 63.5 mmol) in dry THF (200 mL) at −78° C. under $N_2$ was added tert-BuLi (90 mL, 152 mmol, 1.7M/hexane). After 3 h diethyl oxalate (10.3 mL, 76.2 mmol) was added at once. This mixture was stirred for 0.5 h and kept at −30° C. for 14 h. At this time all solvent was removed and the dry residue treated with THF (250 mL) and 3M HCl (250 mL)and subsequently refluxed for 4 h. The reaction was cooled and the TBF removed. The solid isatin precipitated out of solution during this time. It was filtered, washed with $H_2O$ to yield 8.2 g of pure 5-methoxy-6-trifluoromethylisatin lxvii. $^1$H NMR (DMSO-$d_6$) δ 3.89 (s, 3H), 7.05 (s, 1H), 7.42 (s, 1H), 10.99(s, 1H).

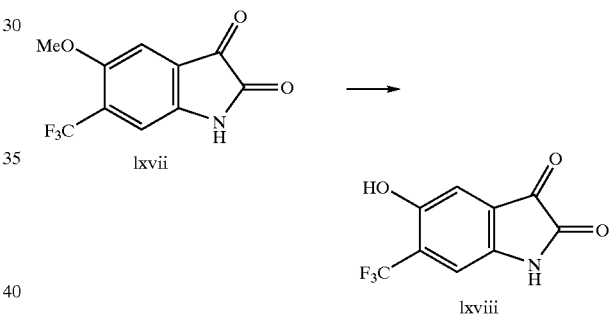

To a stirred mixture of the isatin (335 mg, 1.37 mmol) under $N_2$ at −78° C. in $CH_2Cl_2$ (3 mL) was added $BBr_3$ (2.5 mL, 27.4 mmol) dropwise. The mixture was allowed to reach room temperature in the course of being stirred overnight. The mixture was then carefully poured on ice and the residue extracted with ethyl acetate. Chromatography (5% MeOH /$CH_2Cl_2$) yielded 127 mg of intermediate lxviii. $^1$H NMR (DMSO-$d_6$) δ 6.94 (s, 1H), 7.19 (s, 1H), 10.67 (s, 1H), 10.92 (s, 1H).

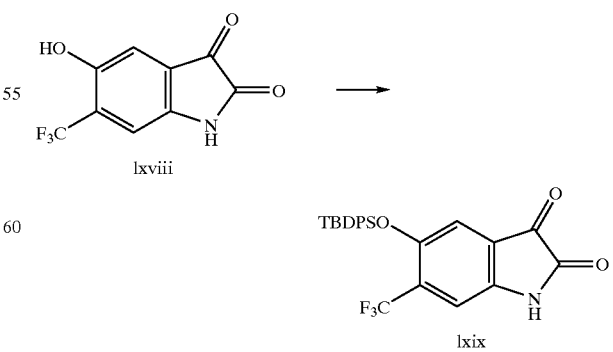

To a stirred solution of the isatin lxviii (256 mg, 1.1 mmol) in DMF was added TBDPSiCl (457 mg, 1.66 mmol)

and imidazole (226 mg, 3.3 mmol) then heated to 55° C. for 1 h. The mixture was poured into H₂O extracted with ether and chromatographed (4:1 hexane/ethyl acetate) yield 357 mg of lxix. ¹H NMR (DMSO-d6) δ 0.31 (s, 6H), 0.90 (s, 9H), 7.08 (s, 2H), 11.05 (s, 1H).

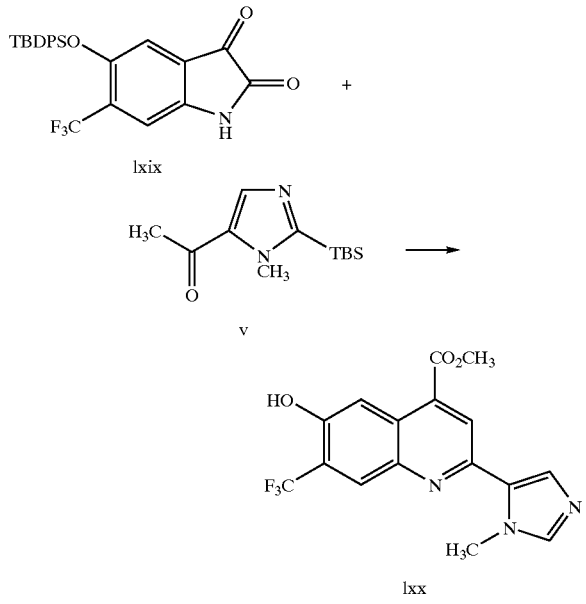

A solution of the isatin lxix (504 mg, 2.18 mmol), imidazole v (571 mg, 2.4 mmol) in AcOH (7 mL) and conc HCl (2.2 mL) was refluxed for 9 days. At this time the solvents were removed, the dry residue was dissolved in MeOH (5 mL) and conc H₂SO₄ (catalytic) was added, and the solution was refluxed overnight. The majority of the solvent was removed and a saturated NaCl solution was added. The solid precipitate was filtered and collected. Yield of lxx: 275 mg two steps.

Alternatively:

To a stirred solution of the isatin lxix (215 mg, 0.46 mmol) and imidazole v (109 mg, 0.46 mmol) in EtOH (1 mL) was added Et₃N (0.16 mL, 1.15 mmol) dropwise, and the resulting solution was stirred overnight. At this time a precipitate formed which was filtered off (88 mg). The remaining filtrate was dried under reduced pressure and the resulting residue was combined with the solid and subjected to THF (1.7 mL) and conc HCl (0.68 mL). This mixture was refluxed overnight, then dried to a residue under reduced pressure, MeOH (5.0 mL) and H₂SO₄ (0.2 mL) was added and the mixture refluxed overnight. A solid precipitated, lxx, was filtered and collected. Yield: 100 mg in three steps. ¹H NMR (DMSO-d₆) δ 4.02 (s, 3H), 4.28 (s, 3H), 8.29 (s, 1H), 8.42 (s, 1H), 8.46 (s, 1H), 8.52 (s, 1H), 9.10 (s, 1H), 11.61 (s, 1H).

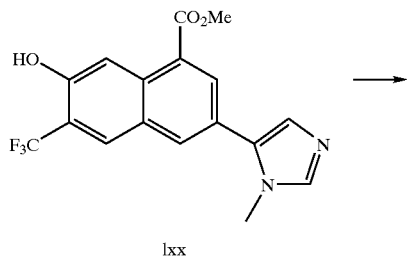

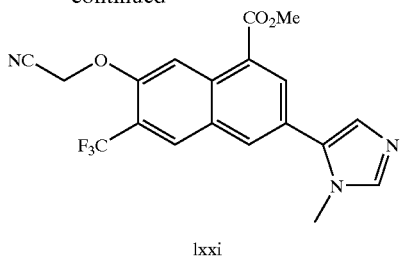

To stirred solution of intermediate lxx (355.4 mg, 1.00 mmol) in DMF (5 mL) was added K₂CO₃ (152 mg, 1.10 mmol) at 0° C., after 15 min. bromoacetonitrile (0.14 mL, 2.0 mmol) was added at room temperature. After 1 h the reaction mixture was placed in an oil bath, 55° C. and heated for 1.5 h. At this time an additional amount of bromoacetonitrile (0.14 mL, 2.0 mmol) was added. The reaction was kept for two more h at 55° C. when another 2 mmol of bromoacetonitrile was added. Heating (40–50° C.) was continued overnight. At this time the mixture was poured into water, extracted with diethyl ether, washed with sat. NaHCO₃ and brine to give after solvent removal the crude product lxxi. Yield: 187 mg.

Example 1

This example illustrates a procedure for the conversion of a derivatized aromatic ester or aldehyde into a desired compound of formula I.

1.1 Preparation of Aldehyde lxxii

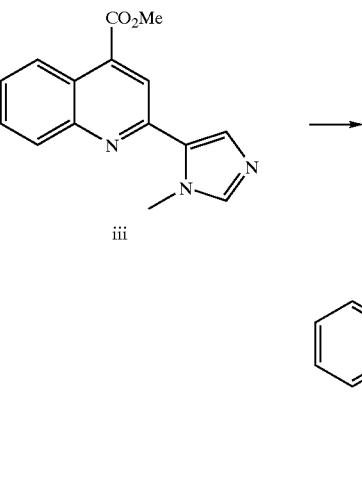

A solution of the ester iii (1.7 g, 6.4 mmol, prepared as described by Method A) in 20 mL of THF was cooled to −78° C. under nitrogen. A 1.0 M solution of LiAlH₄ (7 mL, 7.0 mmol) in THF was added and the reaction stirred at the same temperature for 90 min. The reaction was quenched with water, allowed to reach room temperature, diluted with EtOAc and washed with water, brine, dried over Na₂SO₄, and concentrated to give a mixture of the corresponding aldehyde and alcohol. The crude product was purified (SiO₂, CH₂Cl₂/MeOH, 95:5) to obtain the aldehyde lxxii (0.6 g, 39%) as a yellow solid. ¹H NMR (DMSO-d₆) δ 10.49 (s, 1H), 8.91 (dd, J=8.4, 1.0 Hz, 1H), 8.52 (s, 1H), 8.11 (dd, J=8.5, 1.0 Hz, 1H), 7.94 (s, 1H), 7.91 (s, 1H), 7.85 (ddd, J=8.4, 6.9, 1.5 Hz, 1H), 7.72 (ddd, J=8.4, 6.9, 1.0 Hz, 1H), 4.17 (s, 3H).

1.2 Preparation of Final Semicarbazone 1.1

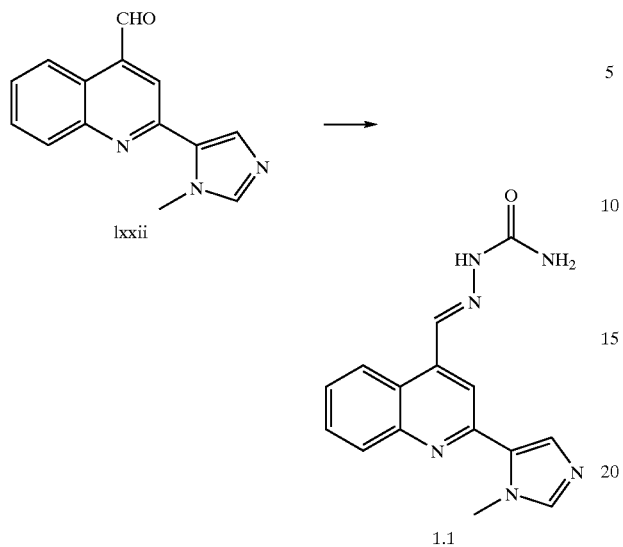

A mixture of 200 mg (0.84 mmol) of the aldehyde lxxii (100 mg, 0.89 mmol, prepared in Example 1.1) of semicarbazide hydrochloride (Aldrich Chemical Co., Milwaukee, Wis., USA), and 100 mg (0.72 mmol) of $K_2CO_3$ in 5 mL of EtOH was stirred in an oil bath at 70° C. for 18 h. The reaction mixture was cooled and the precipitate was filtered, washed with water, and dried under vacuum to give the desired product 1.1(170 mg). mp 236–237° C.; $^1$H NMR (DMSO-$d_6$) δ 10.6 (s, 1H), 8.65 (s, 1H), 8.39 (s, 1H), 8.25 (d, J=7.9 Hz, 1H), 8.03 (d, J=7.5 Hz, 1H), 7.99 (s, 1H), 7.84 (s, 1H), 7.78 (br t, J=7.1 Hz, 1H), 7.64 (br t, J=7.0 Hz, 1H), 6.82 (br s, 2H), 4.15 (s, 3H); Anal. Calcd. for $C_{15}H_{14}N_6O$: C, 61.22; H, 4.79; N, 28.55. Found: C, 61.12; H, 4.69; N, 28.35.

1.3 Preparation of Final N-methylsemithiocarbazone 1.2

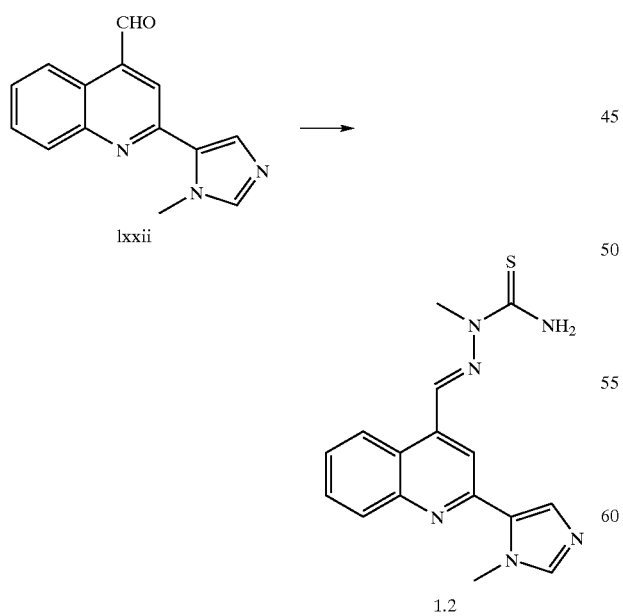

A solution of the aldehyde lxxii (200 mg, 0.84 mmol, prepared in Example 1.1) and 2-methyl-3-thiosemicarbazide (84 mg, 0.84 mmol) in 3 mL of EtOH was stirred at 70° C. for 18 h. The reaction brought to room temperature and the solid collected by filtration, washed with ethanol and water and dried to obtain the desired product 1.2 (130 mg) as a yellow solid. mp 229–230° C.; $^1$H NMR (DMSO-$d_6$) δ 8.69 (br s, 1H), 8.60 (br s, 1H), 8.55 (s, 1H), 8.54 (d, J=7.8 Hz, 1H), 8.49 (s, 1H), 8.04 (d, J=7.4 Hz, 1H), 8.00 (s, 1H), 7.85 (s, 1H), 7.80 (br t, J=8.2 Hz, 1H), 7.64 (br t, J=8.3 Hz, 1H), 4.15 (s, 3H), 3.97 (s, 3H).

The following compounds were prepared in a similar manner, beginning with the corresponding esters prepared by Method B.

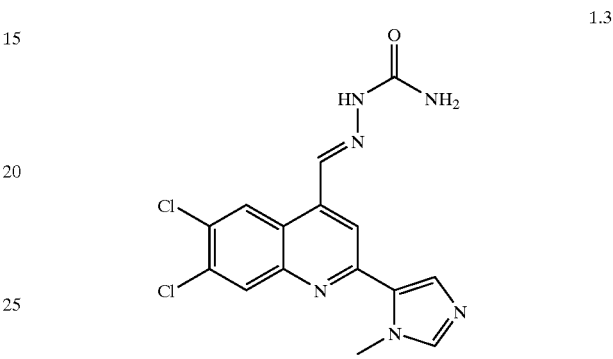

$^1$H NMR (DMSO-$d_6$) δ 10.54 (s, 1H). 8.53 (s, 1H), 8.48 (s, 1H) 8.40 (s, 1H), 8.28 (s, 1H), 8.05 (br s, 1H), 7.85 (br s, 1H), 6.82 (br s, 1H), 4.13 (s, 3H); ESI-MS m/z 363.0 (100, M+H$^+$).

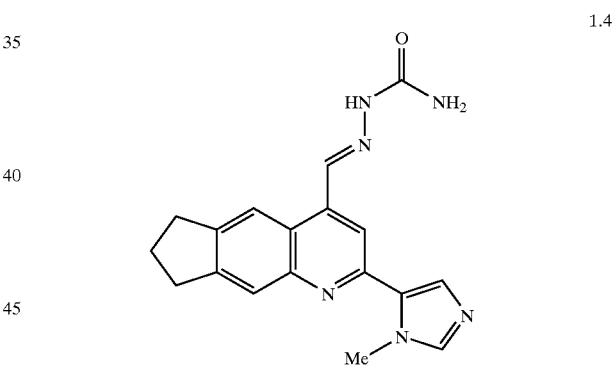

$^1$H NMR ($d_6$-DMSO) δ: 10.53 (s, 1H), 8.66 (s, 1H), 8.31 (s, 1H), 8.00 (s, 1H), 7.93 (s, 1H), 7.85 (s, 1H), 7.82 (s, 1H), 6.82 (broad s, 2H), 4.13 (s, 3H), 3.08 (t, J=7.2 Hz, 4H), 2.13 (m, 2H).

The following compounds were prepared by similar methods beginning with the corresponding esters prepared by Method D.

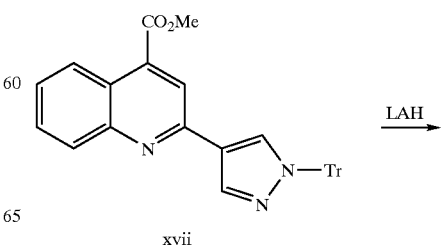

-continued

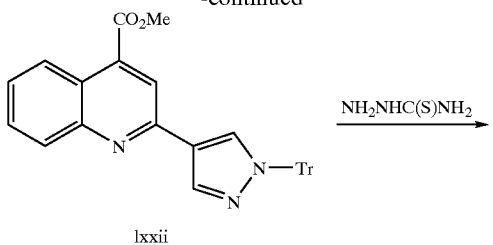

lxxii

NH₂NHC(S)NH₂ →

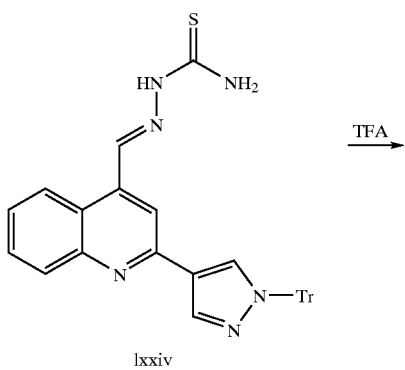

lxxiv

TFA →

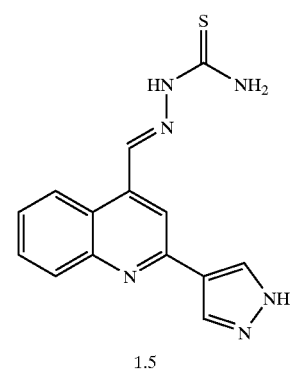

1.5

The starting ester was reduced by the standard procedure described in Example 1.1 to afford a mixture of aldehyde and alcohol. The thiosemicarbazone was prepared from this mixture by using the standard procedure described in Example 1.3. The trityl-protected thiosemicarbazone lxxiv (12 mg, 0.02 mmol) was treated with TFA:DCM (1:1, 2 mL) and stirred at room temperature for 5 h, then concentrated in vacuo. Reverse phase HPLC afforded the desired product 1.5 (3 mg, 50%); $^1$H NMR (CD$_3$OD) δ 8.78 (s, 1H), 8.31–8.48 (m, 3H), 8.04–8.08 (m, 1H), 7.74–7.79 (m, 1H), 7.58–7.63 (m, 1H); ESI-MS m/z 297.0 (100, M+H$^+$).

The following compound was prepared by the standard procedure (see synthesis of Examples 1.1 and 1.2), using an ester prepared according to Method E.

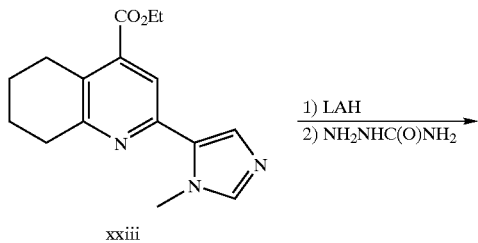

xxiii

1) LAH
2) NH₂NHC(O)NH₂ →

-continued

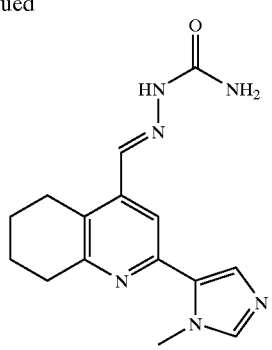

1.6

The aldehyde was prepared by LAH reduction of the ester xxiii: $^1$H NMR (CDCl$_3$) δ 10.18 (s, 1H), 7.67 (s, 1H), 7.50 (s, 1H), 7.46 (s, 1H), 4.00 (s, 3H), 3.16–3.19 (m, 2H), 2.98–3.05 (m, 2H), 1.81–1.97 (m, 2H).

The semicarbazone was prepared by the standard procedure to provide 1.6: $^1$H NMR (DMSO-d$_6$) δ 10.45 (s, 1H). 8.09 (s, 1H), 8.01 (s, 1H) 7.67 (s, 1H), 7.57 (s, 1H), 7.65 (br s, 1H), 3.92 (s, 3H), 2.77–2.85 (m, 4H), 1.78–1.81 (m, 4H); ESI-MS m/z 299.1 (100, M+H$^+$).

The compound below was prepared by the standard procedure (see Example 1.2) using an ester prepared according to Method F.

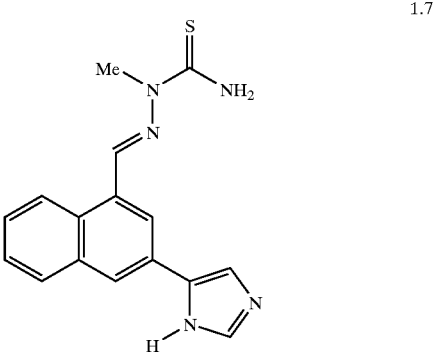

1.7

$^1$H NMR (d$_6$-DMSO) δ: 861 (s, 1H), 8.57 (s, 1H), 8.50–8.52 (m, 1H), 8.39 (s, 1H), 8.29 (s, 1H), 7.98–8.00 (m, 1H), 7.92 (m, 1H), 7.82 (s, 1H), 7.55–7.57 (m, 2H), 3.97 (s, 3H).

The compound described below was prepared using the methods above beginning with the corresponding ester compound prepared according to Method G.

1.8

$^1$H NMR (d$_6$-DMSO) δ: 10.48 (s, 1H), 9.74 (s, 1H), 8.79 (s, 1H), 8.40 (s, 1H), 8.33 (s, 1H), 8.05 (s, 2H), 7.99 (s, 1H), 7.84 (s, 1H), 7.68 (d, J=8.6 Hz, 2H), 6.93 (d, J=8.6 Hz, 2H), 6.83 (s, 2H), 4.17 (s, 3H).

The compound described below was prepared using the methods above beginning with the corresponding diol compound prepared according to Method H.

Preparation of 1.9.

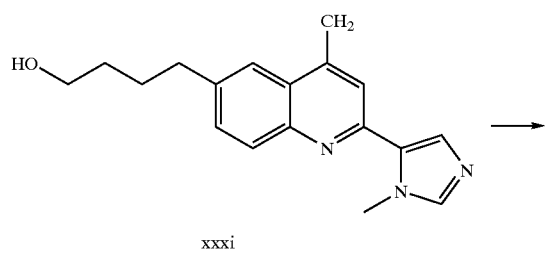

xxxi

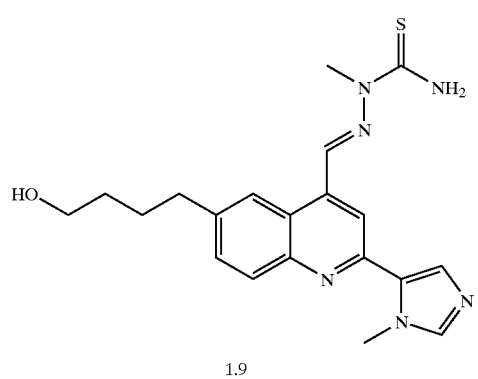

1.9

A mixture of the diol xxxi (100 mg, 0.32 mmol) and MnO$_2$ (1.0 g) in 10 mL of THF was stirred at room temperature for 18 h. The reaction was filtered over Celite, the residue washed with THF and EtOAc, and the filtrate concentrated to give a solid. The crude was purified (SiO$_2$, CH$_2$Cl$_2$/MeOH, 95:5) to give an intermediate aldehyde (50 mg, 50%) which was carried on directly.

A solution of the aldehyde (50 mg, 0.16 mmol) and 2-methyl-3-thiosemicarbazide (20 mg, 0.19 mmol) in 3 mL of EtOH was stirred at reflux for 18 h. The reaction brought to room temperature, the precipitate filtered, washed with EtOH, and dried to give the desired N-methyl semithiocarbazone 1.9 (28 mg, 44%). 192.6–194.7° C., $^1$H NMR (DMSO-d$_6$) δ 8.71 (br s, 1H), 8.59 (br s, 1H), 8.53 (s, 1H), 8.45 (s, 1H), 8.31 (s, 1H), 7.97 (d, J=1.0 Hz, 1H), 7.96 (d, J=8.5 Hz, 1H), 7.85 (s, 1H), 7.67 (dd, J=8.6, 1.7 Hz, 1H), 4.41 (t, J=5.1 Hz, 1H), 4.13 (s, 3H), 3.98 (s, 3H), 3.50–3.40 (m, 2H), 2.83 (t, J=7.6 Hz, 2H), 1.80–1.66 (m, 2H), 1.57–1.45 (m, 2H).

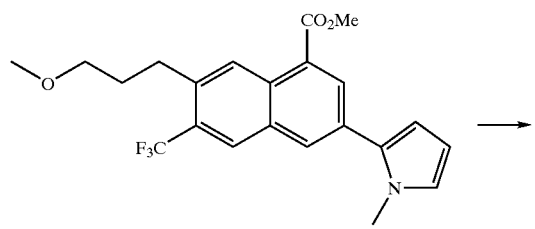

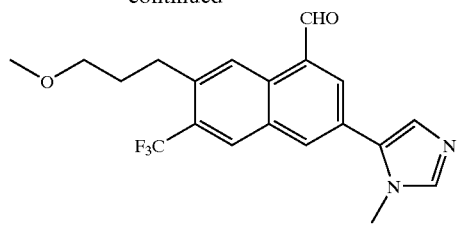

CaCl$_2$ (−30+80 mesh, 34.1 mg, 0.308 mmol) and NaBH (23.3 mg, 0.616 mmol) was added to a stirred solution of the crude saturated methyl ether xxxvi (125 mg, 0.308 mmol) in 1:1 THF-MeOH (10 mL) at 0° C. The cold bath was removed and stirring was continued for 1.5 h. Water (2 mL) was added and the solution was evaporated. The residue was dried under vacuum. To the residue THF (5 mL), CH$_2$Cl$_2$ (5 mL), and Dess-Martin periodinane (522 mg, 1.2 mmol) were added. The mixture was stirred for 1 h, diluted with THF (10 mL), and poured into saturated aqueous NaHCO$_3$ (8 mL) containing Na$_2$S$_2$O$_3$ (2.5 g). The mixture was stirred for 30 min. EtOAc (10 mL) was added, and the layers were separated. The organic layer was washed with water and brine, dried, and evaporated. Flash chromatography of the residue over silica gel, using 1:4:5 MeOH-EtOAc-hexane, gave the aldehyde lxxv (95.2 mg in two steps) as a yellow solid: MS 378.2 (MH$^+$).

Conversion of the aldehyde lxxv to compound 1.10 was accomplished using the methods provided above.

1.10

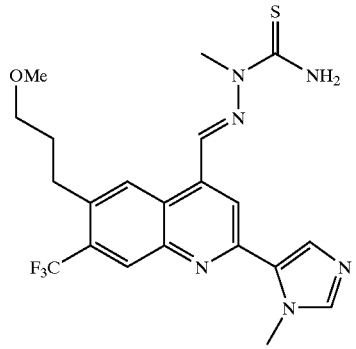

Compound 1.10 was obtained as a yellow solid: $^1$H NMR (DMSO-d$_6$) δ 1.94 (m, 2H), 2.98 (t, 2H), 3.45 (t, 2H), 3.92 (s, 3H), 4.15 (s, 3H), 7.89 (s, 1H), 8.06 (s, 1H), 8.32 (s, 1H), 8.52 (s, 1H), 8.59 (s, 2H), 8.75 (s, 1H); exact mass (electrospray) m/z calcd for C$_{21}$H$_{23}$F$_3$N$_6$OS (M+H) 465.2, found 465.2.

The following compounds were prepared using methods as provided above.

1.11

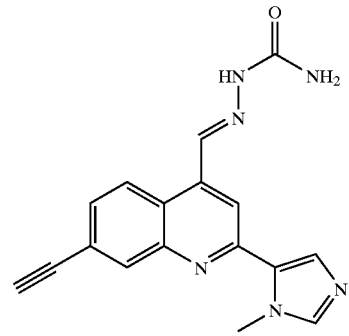

¹H NMR (DMSO-d₆) δ 10.64 (s, 1H). 8.58 (s, 1H), 8.37 (s, 1H) 8.25 (d, J=8.5 Hz, 1H), 8.12 (s, 1H), 7.85 (s, 1H), 7.65 (d, J=8.5 Hz, 1H), 6.82 (br s, 1H), 4.45 (s, 1H), 4.13 (s, 3H). ESI-MS m/z 319.1 (100, M+H⁺).

1.12

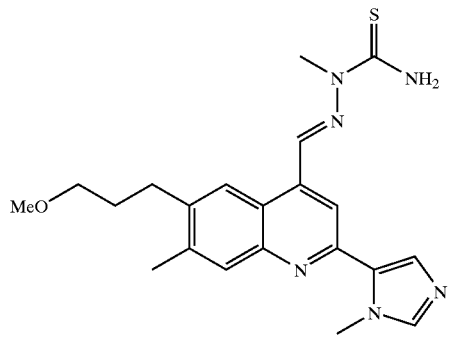

¹H NMR (CD₃OD) δ 8.51 (s, 11H), 8.25 (s, 1H) 8.23 (s, 1H), 7.96 (s, 1H), 7.88 (s, 1H), 7.84 (s, 1H), 4.45 (s, 1H), 4.21 (s, 3H), 4.01 (s, 3H), 3.48–3.51 (m, 2H) 3.37 (s, 3H), 2.92–2.96 (m, 2H), 2.55 (s, 3H), 1.94–1.98 (m, 2H); ESI-MS m/z 411.5 (100, M+H⁺).

1.13

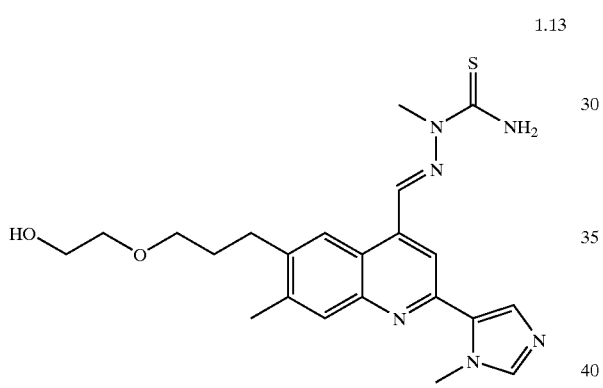

¹H NMR (CD₃OD) δ 9.04 (s, 1H), 8.39 (s, 1H) 8.33 (s, 1H), 8.24 (s, 1H), 8.16 (s, 1H), 7.91 (s, 1H), 4.39 (s, 3H), 3.95 (s, 3H), 3.54–3.71 (m, 6H, 2.92–2.96 (m, 2H), 2.55 (s, 3H), 1.93–2.02 (m, 2H); ESI-MS m/z 441.2 (100, M+H⁺).

1.14

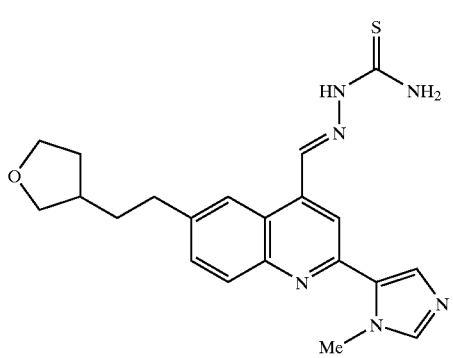

¹H NMR (d₆-DMSO) δ 8.96 (s, 1H), 8.54 (s, 1H), 8.47 (s, 1H), 8.37 (s, 1H), 7.92–7.97 (m, 3H), 7.83 (s, 1H), 7.68 (d, J=8.2 Hz, 1H), 4.13 (s, 3H), 3.83 (t, J=7.3 Hz, 1H), 3.58–3.75 (m, 2H), 2.75–2.85 (m, 2H), 1.98–2.21 (m, 2H), 1.70–1.80 (m, 2H), 1.48–1.62 (m, 2H).

1.15

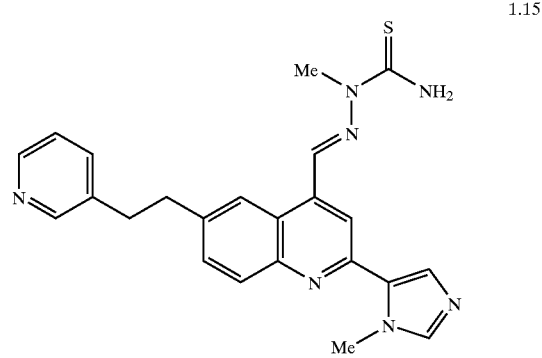

¹H NMR (d₆-DMSO) δ: 876 (s, 1H), 8.58 (s, 1H), 8.49 (s, 1H), 8.47 (s, 1H), 8.41 (m, 1H), 8.34 (s, 1H), 8.29 (s, 1H), 8.17 (s, 1H), 7.99 (d, J=8.7 Hz, 1H), 7.74–7.71 (m, 2H), 7.33 (dd, J=4.8, 7.7, 1H), 4.19 (s, 3H), 3.98 (s, 3H), 3.17 (m, 2H), 3.06 (m, 2H).

The following compounds were prepared from the corresponding ester (prepared by Method 1).

Preparation of 1.16

To a solution of the ester xliii (250 mg, 0.78 mmol) in 5 mL of THF at −78° C. was added a 1.0 M solution of LiAlH₄ (2 mL, 2 mmol) in THF. The reaction was stirred for 2 h and quenched with sat. NH₄Cl, warmed to room temperature, and diluted with EtOAc. The solution was filtered, dried over Na₂SO₄, and concentrated to give the crude alcohol. A suspension of the alcohol and MnO₂ (2.0 g) in 10 mL of THF was stirred at room temperature for 3 days. The reaction mixture was filtered through Celite, the filtrate was concentrated, and the residue was purified (SiO₂, CH₂Cl₂/ MeOH, 96:4) to give an oil. This was triturated with hexane/EtOAc and the solid was filtered to give an intermediate aldehyde (60 mg, 26%).

A solution of the aldehyde (55 mg, 0.19 mmol) and 2-methyl-3-thiosemicarbazide (19 mg, 0.18 mmol) in 3 mL of EtOH was stirred at reflux for 18 h. The reaction was cooled, the precipitate collected, washed with EtOH, and dried to give the desired product 1.16 (30 mg, 42%). ¹H NMR (DMSO-d₆) δ 8.72 (br s, 1H), 8.62 (br s, 1H), 8.53 (s, 1H), 8.48 (s, 1H), 8.43 (s, 1H), 8.01 (d, J=8.5 Hz, 1H), 7.98 (s, 1H), 7.84 (s, 1H), 7.76 (d, J=8.6 Hz, 1H), 4.14 (s, 3H), 3.98 (s, 3H), 3.14 (t, J=7.2 Hz, 2H), 2.98 (t, J=7.2 Hz, 2H).

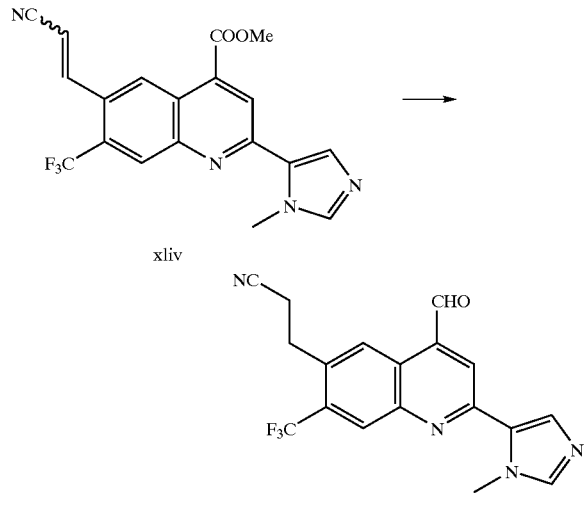

xliv lxxvi

CaCl$_2$ (−30+80 mesh, 109 mg, 0.983 mmol) and NaBH$_4$ (74.4 mg, 1.97 mmol) was added to a stirred solution of the unsaturated nitrile (253 mg, 0.655 mmol) in 1:1 THF-EtOH (30 mL) at 0° C. The cold bath was removed and stirring was continued overnight. Water (2 mL) was added and the solution was evaporated. The residue was then dried under vacuum. To the residue THF (35 mL), CH$_2$Cl$_2$ (35 mL), and Dess-Martin periodinane (1.21 g, 2.86 mmol) were added. The mixture was stirred for 2 h, diluted with THF (30 mL), and poured into saturated aqueous NaHCO$_3$ (48 mL) containing Na$_2$S$_2$O$_3$ (12.1 g). The mixture was stirred for 30 min. EtOAc (10 mL) was added, and the layers were separated. The organic layer was washed with water and brine, dried, and evaporated. Flash chromatography of the residue over silica gel, using 1:4:5 MeOH-EtOAc-hexane, gave the aldehyde lxxvi (111.3 mg in two steps) as a yellow solid: MS 359.1 (MH$^+$).

Conversion of aldehyde lxxvi to compound 1.16a was accomplished using the methods described above.

1.16a

Compound 1.16a was obtained as a yellow solid: $^1$H NMR (DMSO-d$_6$) δ 3.03 (t, J=6.0 Hz, 2H), 3.25 (t, J=6.0 Hz, 2H), 3.99 (s, 3H), 4.50 (s, 3H), 7.89 (s, 1H), 8.08 (s, 1H), 8.37 (s, 1H), 8.57 (s, 1H), 8.48 (s, 1H), 8.61 (s, 1H), 8.66 (s, 1H), 8.68 (s, 1H), 8.76 (s, 1H); MS (electrospray) m/z calcd for C$_{20}$H$_{18}$F$_8$N$_7$S (M+H) 446.1, found 446.1.

The following compounds were prepared according to the general methods above.

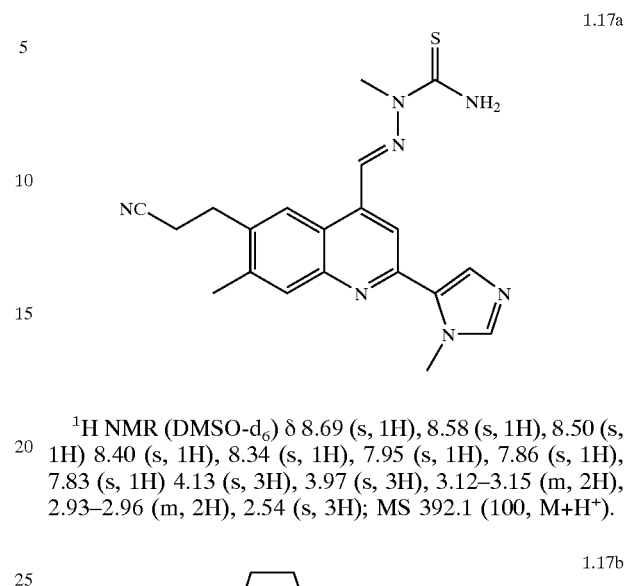

1.17a $^1$H NMR (DMSO-d$_6$) δ 8.69 (s, 1H), 8.58 (s, 1H), 8.50 (s, 1H) 8.40 (s, 1H), 8.34 (s, 1H), 7.95 (s, 1H), 7.86 (s, 1H), 7.83 (s, 1H) 4.13 (s, 3H), 3.97 (s, 3H), 3.12–3.15 (m, 2H), 2.93–2.96 (m, 2H), 2.54 (s, 3H); MS 392.1 (100, M+H$^+$).

1.17b

Compound 1.17b was obtained as a yellow solid: $^1$H NMR (CD3OD) δ 2.04 (br s, 2H), 2.17 (br s, 2H), 2.95 (t, J=6.96 Hz, 2H), 3.17 (br s, 2H), 3.36 (t, J=6.96 Hz, 2H), 3.57 (t, J=5.88 Hz, 2H), 3.87 (br s, 2H), 4.41 (s, 3H), 4.59 (t, J=5.82 Hz, 2H), 8.28 (s, 1H), 8.44 (s, 1H), 8.45 (s, 1H), 8.56 (s, 1H), 8.70 (s, 1H), 9.08 (s, 1H); MS (electrospray) m/z calcd for C$_{24}$H$_{27}$ClN$_8$O (M+H) 479.2, found 479.2

1.17c

Compound 1.17c was obtained as a yellow solid: $^1$H NMR (DMSO-d$_6$) δ 2.99 (t, J=7.16 Hz, 2H), 3.24 (t, J=7.14 Hz, 2H), 3.71 (t, J=5.68 Hz, 2H), 3.36 (t, J=5.68 Hz, 2H), 4.13

(s, 3H), 4.92 (t, J=5.76 Hz, 2H), 7.88 (s, 1H), 8.02 (s, 1H), 8.16 (s, 1H), 8.42 (s, 1H), 8.46 (s, 1H), 8.55 (s, 1H), 8.74 (s, 1H), 8.75 (s, 1H); MS (electrospray) m/z calcd for C₂₁H₂₂ClN₇OS (M+H) 456.1, found 456.2

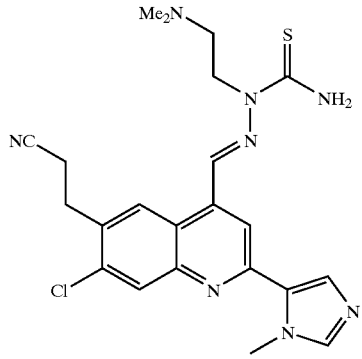

Compound 1.17d was obtained as a yellow solid: ¹H NMR (DMSO-d₆) δ 2.49 (s, 3H), 2.50 (s, 3H), 2.99 (t, J=7.14, 2H), 3.22 (t, J=7.14 Hz, 2H), 3.28–3.30(m, 2H), 4.12 (s, 3H), 4.82 (t, J=6.56 Hz, 2H), 7.86 (s, 1H), 8.02 (s, 1H), 8.16 (s, 1H), 8.43 (s, 1H), 8.48 (s, 1H), 8.55 (s, 1H), 8.66 (s, 1H), 8.73 (s, 1H); MS (electrospray) m/z calcd for C₂₂H₂₅ClN₈S (M+H) 469.2, found 469.2

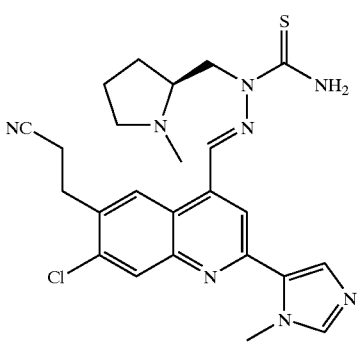

1.17e

Compound 1.17e was obtained as a yellow solid: ¹H NMR (DMSO-d₆) δ 1.92–1.65 (m, 4H), 2.25 (br, s, 1H), 2.36 (s, 3H), 2.87 (br s, 1H), 3.00 (t, J=7.08 Hz, 2H), 3.09 (br s, 1H), 3.19 (m, 2H), 4.13 (s, 3H), 4.61 (1br s, 1H), 4.93 (m, 1H), 7.86 (s, 1H), 8.03 (s, 1H), 8.17 (s, 1H), 8.33 (s, 1H), 8.48 (s, 1H), 8.59 (s, 1H), 8.69 (s, 1H), 9.09 (s, 1H); MS (electrospay) m/z calcd for C₂₄H₂₈ClN₈S (M+H) 495.2, found 495.2

The following compounds were prepared beginning with intermediates provided above in Method J.

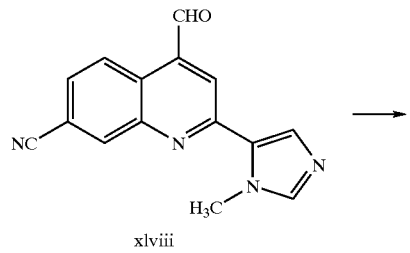

xlviii

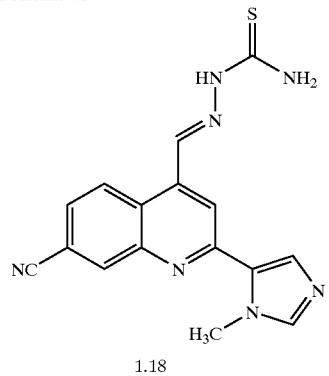

1.18

To a solution of the above aldehyde xlviii (34.8 mg, 0.133 mmol) in EtOH (2 mL) and H₂O (0.5 mL) was added the semithiocarbazide (13.3 mg, 0.146 mmol) and 1 drop of AcOH. The mixture was refluxed overnight. The resulting mixture was cooled and the yellow solid filtered and washed with water. The solid was dried and found pure by TLC, NMR and MS. Yield of 1.18: 13.5 mg. (¹H NMR, 400 MHz): ¹H NMR (CDCl₃) δ 4.15 (s, 3H), 7.89 (s, 1H), 7.95 (d, J=12 Hz, 1H), 8.08 (s, 1H), 8.32 (d, J=12 Hz, 1H), 8.40 (s, 1H), 8.58 (m, 3H), 8.85 (s, 1H), 11.75 (s, 1H). MS 334.1 (M−H⁻).

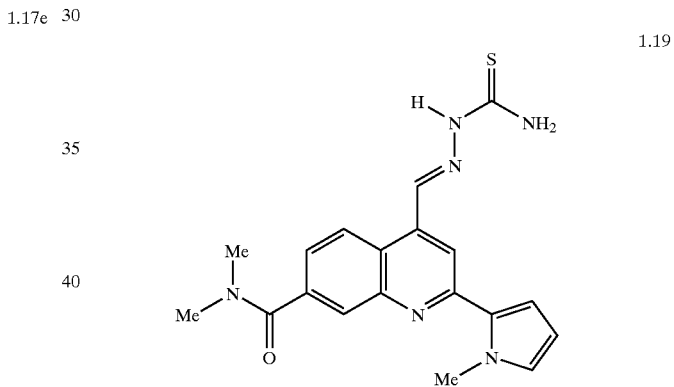

1.19

From xlix, using the general method (Example 1.2).

¹H NMR (d₆-DMSO) δ: 11.72 (s, 1H), 8.83 (s, 1H), 8.56 (s, 1H), 8.52 (s, 1H), 8.39 (s, 1H), 8.22 (d, J=8.7, 1H), 8.02 (s, 2H), 7.86 (s, 1H), 7.65 (dd, J=1.6, 8.7 Hz, 1H), 4.15 (s, 3H), 3.06 (s, 3H), 2.99 (s, 3H).

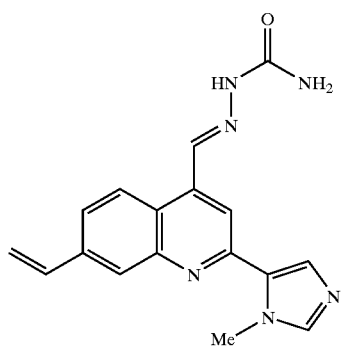

1.20

From intermediate 1, using the general method (Example 1.2).

¹H NMR (d₆-DMSO) δ: 863 (s, 1H), 8.36 (s, 1H), 8.22 (d, J=8.8, 1H), 8.15 (s, 1H), 8.11 (s, 1H), 8.02 (s, 1H), 7.88 (d, J=8.8 Hz, 1H), 6.98 (dd, J=10.6, 17.6 Hz, 1H), 6.83 (bs, 2H), 6.11 (d, J=17.6 Hz, 1H), 5.48 (d, J=10.6 Hz, 1H), 4.19 (s, 3H).

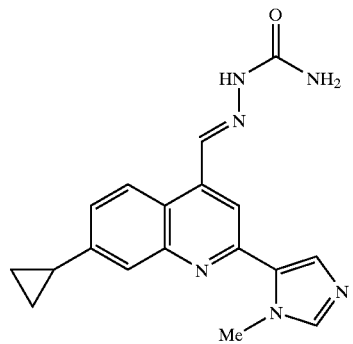

1.21

From intermediate li, using the general method (Example 1.2).

¹H NMR (d₆-DMSO) δ: 10.60 (s, 1H), 8.61 (s, 1H), 8.29 (s, 1H), 8.12 (d, J=8.7 Hz, 1H), 7.95 (s, 1H), 7.83 (s, 1H), 7.72 (s, 1H), 7.35 (d, J=8.7 Hz, 1H), 6.80 (s, 2H), 4.15 (s, 3H), 2.15–2.17 (m, 1H), 1.08–1.12 (m, 2H), 0.86–0.88 (m, 2H).

The following compounds were prepared beginning with the corresponding esters prepared by Method K.

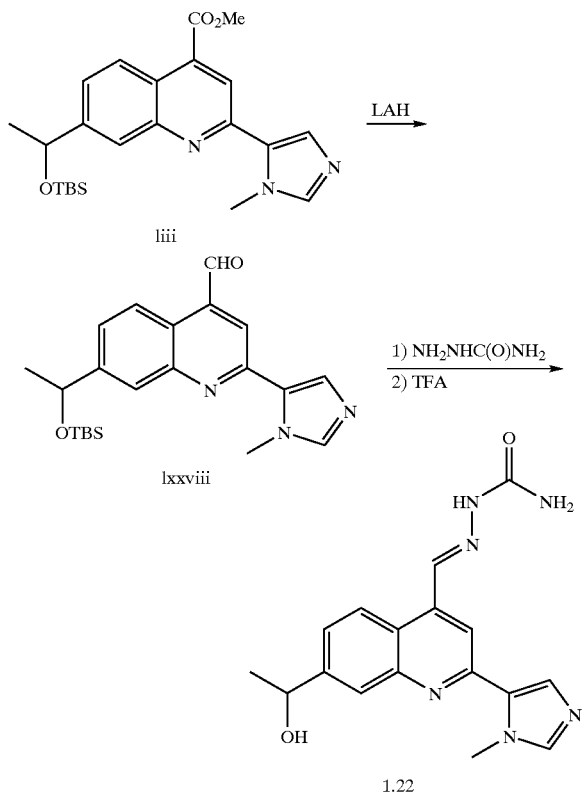

The aldehyde lxxviii was formed by LAH reduction of the ester liii according to the general procedure (see Example 1).

¹H NMR (CDCl₃) δ 10.42 (s, 1H), 8.90 (s, 1H), 8.00–8.04 (m, 2H), 7.75 (s, 1H), 7.66 (d, J=7 Hz, 1H), 7.50 (s, 1H), 5.08 (q, J=6 Hz, 1H), 4.12 (s, 3H), 1.43–1.46 (m, 3H), 0.94 (s, 9H), 0.10 (s, 3H), 0.01 (s, 3H).

To a stirred solution of aldehyde lxxviii (38 mg, 0.096 mmol) in ethanol:water (5:1; 4 mL) was added semicarbazide hydrochloride (11 mg, 0.098 mmol) and sodium acetate (24 mg, 0.28 mmol). The mixture was heated at reflux for 12 h then allowed to cool to room temperature. The precipitate was collected and washed with water then dissolved in TFA (2 mL). The mixture was stirred for 36 h at room temperature then concentrated in vacuo. The residue was purified by reverse-phase HPLC to afford the desired product 1.22 (5 mg). ¹H NMR (CD₃OD) δ 9.07 (s, 1H). 8.67 (s, 1H), 8.42 (s, 1H), 8.38 (s, 1H), 8.35 (s, 1H), 8.14 (s, 1H), 7.74–7.77 (m, 1H), 5.07 (q, J=6 Hz, 1H), 4.43 (s, 3H), 1.55 (d, J=6 Hz, 3H); ESI-MS m/z 339.2 (100, M+H⁺).

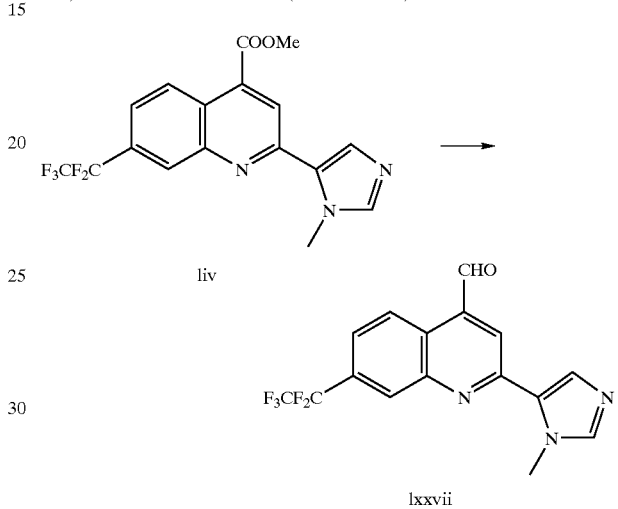

LiAlH₄ (1.0M in THF, 1.4 mL, 1.40 mmol) was added to a stirred and cooled (−78° C.) solution of the pentafluoroethyl compound liv (180 mg, 0.467 mmol) in THF (10 mL). Stirring was continued at −78° C. for 3 h. Water (0.1 mL), 2N NaOH (0.1 mL), and water (0.3 mL) were added sequentially. The cold bath was removed and the mixture was stirred for 30 min, and then filtered through a pad of Celite. The pad was rinsed with THF and the combined filtrates were evaporated. Flash chromatography of the residue over silica gel, using 1:4:5 MeOH-EtOAc-hexane, gave the crude alcohol (104 mg) for next step.

Dess-Martin periodinane (246 mg, 0.580 mmol) was added to the alcohol (104 mg, 0.290 mmol) in 1:1 THF-CH₂Cl₂ (15 mL). The mixture was stirred for 2 h, diluted with THF (30 mL), and poured into saturated aqueous NaHCO₃ (10 mL) containing Na₂S₂O₃ (2.5 g). The mixture was stirred for 30 min. EtOAc (10 mL) was added, and the layers were separated. The organic layer was washed with water and brine, dried, and evaporated. Flash chromatography of the residue over silica gel, using 1:4:5 MeOH-EtOAc-hexane, gave the aldehyde lxxvii (84.8 mg) as a yellow solid for the next final coupling reaction.

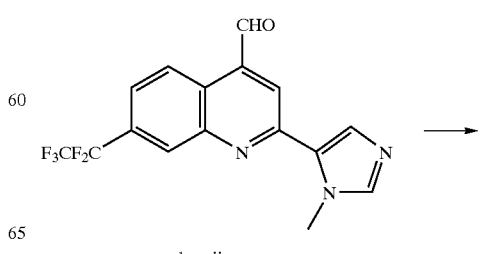

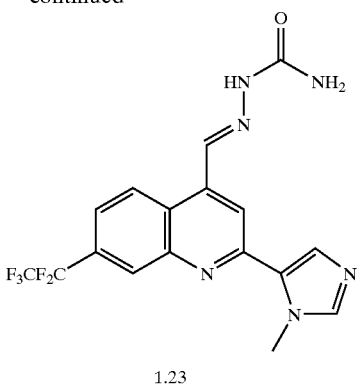

1.23

NaOAc (30.1 mg, 0.367 mmol) was added to a stirred solution of the aldehyde lxxvii (43.5 mg, 0.123 mmol), semicarbazide hydrochloride (13.6 mg, 0.123 mmol) in 4:1 EtOH-H₂O (4.5 mL), and the mixture was refluxed for 14 h. The resulting mixture was cooled and precipitates were collected. Purification by rinse with cold MEOH gave corresponding 7-pentafluoroethyl semicarbazone 1.23 (15.0 mg) as a yellow solid: ¹H NMR (DMSO-d₆) δ 4.19 (s, 3H), 6.85 (br s, 2H), 7.88 (d, J=8.8 Hz, 1H), 8.03 (s, 1H), 8.15 (s, 1H), 8.34 (s, 1H), 8.52 (s, 1H), 8.58 (d, J=8.8 Hz, 1H), 8.61 (s, 1H), 10.73 (s, 1H); ms 413.1 (M+H⁺).

The following compounds were prepared from the corresponding esters prepared by the methods of Method L.

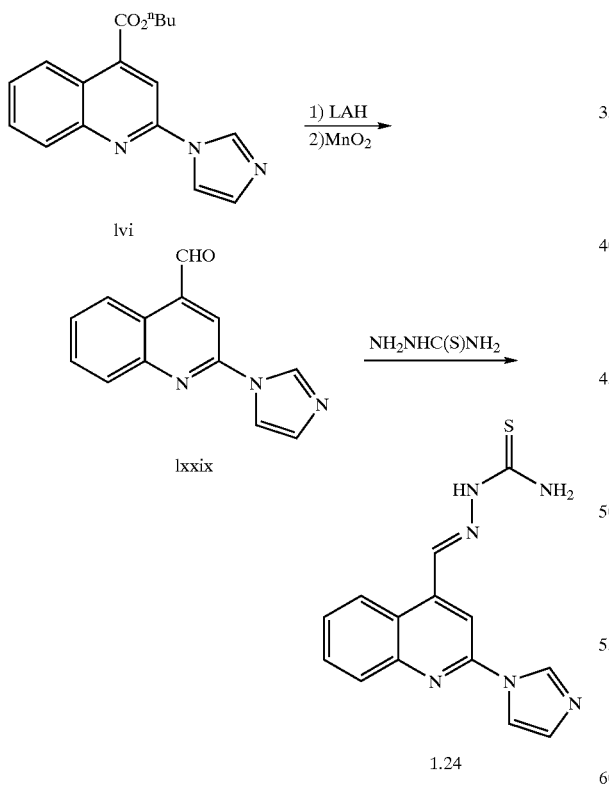

To a stirred solution of butyl ester lvi (152 mg, 0.5 mmol) in anhydrous THF (3 mL) at −78° C. under nitrogen was added lithium aluminum hydride (515 μl of a 1M solution in THF, 0.5 mmol). The mixture was stirred at −78° C. for 30 min. then quenched by the addition of ethyl acetate (5 mL) and water (5 mL). The mixture was allowed to warm to room temperature, diluted with ethyl acetate (50 mL) and water (20 mL). The organics were collected and dried (Na₂SO₄), filtered and concentrated in vacuo. Flash chromatography afforded a mixture of alcohol and aldehyde which were taken up in THF (10 mL). Manganese dioxide (350 mg) was added and the mixture was stirred under nitrogen for 12 hours whereupon a further MnO₂ (350 mg) was added. The mixture was stirred for a further 3 h then filtered and concentrated in vacuo to afford impure aldehyde lxxix (40 mg). ESI-MS m/z 224.3 (100, M+H⁺).

To a stirred solution of aldehyde lxxix (40 mg, 0.17 mmol) in ethanol:water (5:1; 1 mL) was added thiosemicarbazide (20 mg, 1.2 eq.) and a drop of acetic acid. The mixture was heated at reflux for one hour then cooled and the precipitate collected by filtration and washed with water and cold ethanol to yield 1.24 (15 mg). ¹H NMR (DMSO-d₆) δ 11.81 (s, 1H), 8.95 (s, 1H), 8.82 (s, 1H) 8.66 (s, 1H), 8.54 (s, 1H), 8.45 (s, 1H), 8.17–8.20 (m, 2H), 8.03–8.05 (m, 1H) 7.78–7.87 (m, 1H) 7.71–7.23 (m, 1H); ESI-MS m/z 297.3 (100, M+H⁺).

Similarly, the following compound was prepared according to the general procedure above.

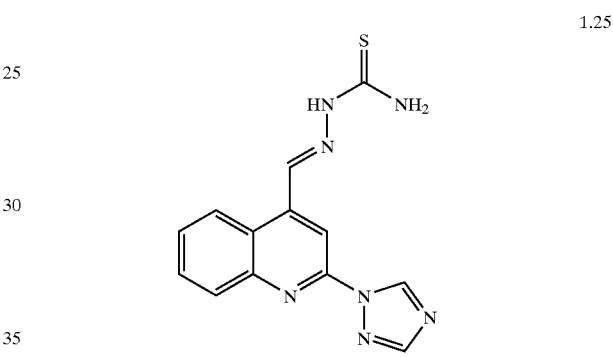

1.25

¹H NMR (DMSO-d₆) δ 11.76 (s, 1H), 9.55 (s, 1H) 8.94 (s, 1H), 8.58 (s, 1H), 8.54 (s, 1H), 8.33–8.39 (m, 3H), 8.08 (d, J=8 Hz, 1H), 7.89–7.93 (m, 1H), 7.76–7.78 (m, 1H); ESI-MS m/z 298.1 (100, M+H⁺).

The following compound was prepared from the aldehyde described in Method M.

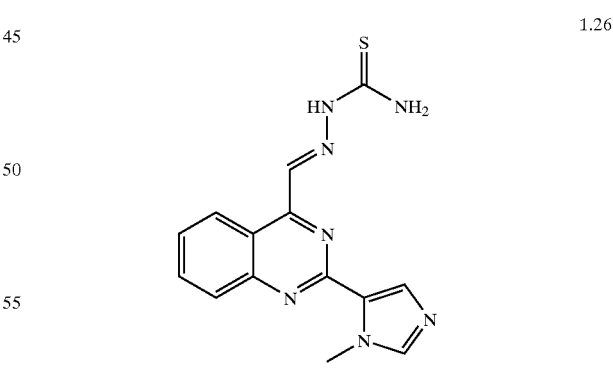

1.26

To a stirred solution of crude aldehyde lx was added thiosemicarbazide (33 mg, 0.3 mmol) and a drop of acetic acid. The mixture was heated at reflux for 90 min. then allowed to cool to room temperature. The precipitate formed was collected by filtration and purified by reverse-phase HPLC to afford the desired product 1.26 (10 mg); ¹H NMR (DMSO-d₆) δ 11.98 (br s, 1H), 9.00 (d, J=8.5 Hz, 1H), 8.65 (br s, 1H) 8.50 (s, 1H) 7.86–7.99 (m, 5H) 7.67–7.72 (m, 1H) 4.15 (s, 3H); ESI-MS m/z 312.2 (100, M+H⁺).

The following compound was prepared from the aldehyde described in Method N.

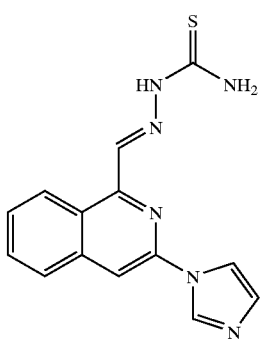

1.27

The solution of aldehyde lxiv was concentrated to a volume of approx. 1 mL then ethanol (5 mL) and water (1 mL) were added and the mixture concentrated again to approx. 1.5 mL. Ethanol (5 mL) was added and the mixture again concentrated to approx. 1.5 mL. Ethanol (2 mL) was added. To this solution was added thiosemicarbazide (72 mg) and one drop of acetic acid. The mixture was heated at reflux for 12 h then concentrated to dryness. The residue was purified by reverse-phase preparative HPLC to afford isoquinoline 1.27 (2 mg, 0.8%); $^1$H NMR (DMSO-$d_6$) δ 11.92 (br s, 1H), 9.07 (d, 1H, J=8 Hz), 8.70 (s, 1H) 8.61 (br s, 1H) 8.48 (s, 1H) 7.88–8.11 (m, 6H).

The following compound was prepared in a similar manner from the aldehyde described in Method O.

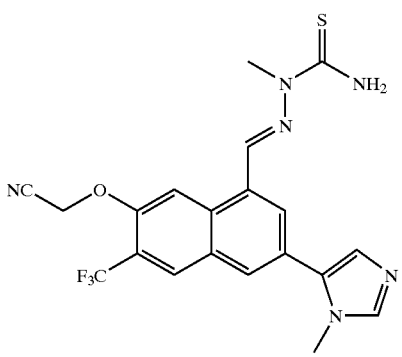

1.28

$^1$H NMR (400 MHz, DMSO-$d_6$) δ 4.00 (s, 3H), 4.19 (s, 3H), 5.60 (s, 2H), 8.15 (br s, 2H), 8.26 (s, 1H), 8.43 (s, 1H), 8.48 (s, 1H), 8.61 (s, 1H), 8.64 (s, 1H), 8.80 (s, 1H). ms 348.0 (M+H$^+$).

Example 2

This example illustrates the preparation of a 2-triazolyl-quinoline semithiocarbazone.

2.1 Preparation of 2-carboxaldehyde-quinoline-4-carboxylic acid, methyl ester.

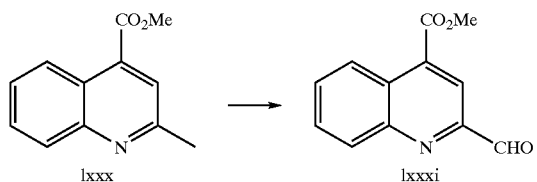

A solution of the quinoline ester lxxx (1.35 g, 6.7 mmol) in dioxane was heated to reflux. SeO$_2$ (1.49 g, 13.4 mmol) was added and the reflux continued for 30 min. The reaction was cooled, diluted with Et$_2$O, filtered, and the ethereal phase was washed with water, 10% NaHCO$_3$ (2×), brine, dried over Na$_2$SO$_4$, and concentrated to dryness to give the aldehyde lxxxi as a solid (1.25 g, 87%). $^1$H NMR (DMSO-$d_6$) δ 10.16 (s, 1H), 8.73 (dd, J=8.3, 1.2 Hz, 1H), 8.35 (dd, J=8.1, 1.0 Hz, 1H), 8.33 (s, 1H), 8.02 (ddd, J=8.4, 6.9, 1.5 Hz, 1H), 7.94 (ddd, J=8.5, 6.9, 1.5 Hz, 1H), 4.03 (s, 3H).

2.2 Preparation of Intermediate lxxxii.

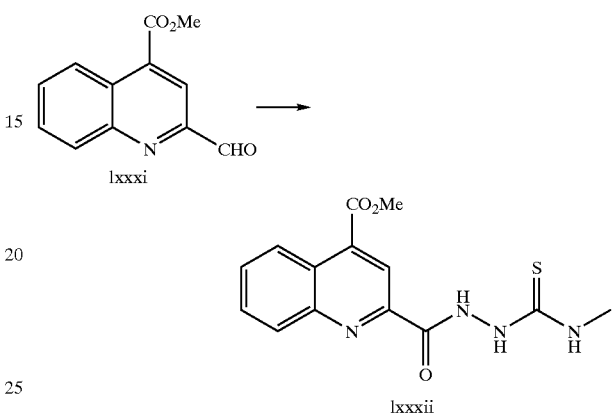

To a solution of the aldehyde lxxxi (1.25 g, 5.81 mmol) and sulfamic acid (1.35 g, 14.53 mmol) in 20 mL oft-butanol was added a solution of NaClO$_2$ (1.30 g, 14.53 mmol) and KH$_2$PO$_4$ (1.97 g, 14.53 mmol) in 2 mL of water. The bi-phased reaction was stirred vigorously for 30 min. The reaction was quenched with AcOH (3.1 mL) and diluted with water. The mixture was extracted with EtOAc (2×), and the organic layer washed with water, brine, dried over Na$_2$SO$_4$, and concentrated to dryness to give an intermediate carboxylic acid (1.24 g, 93%).

To a solution of the carboxylic acid (1.24 g, 5.4 mmol) and DMF (0.61 mL, 7.87 mmol) in 10 mL of CH$_2$Cl$_2$ at 0° C. was added oxalyl chloride (1.46 mL, 16.7 mmol) dropwise. The reaction was stirred at 0° C. for 15 min and room temperature for 30 min. The solvent was removed in vacuum to dryness to give a yellow solid. The crude product was cooled to 0° C. and added a solution of 4-methyl-3-thiosemicarbazide (1.65 g, 15.76 mmol) in 15 mL of pyridine. The suspension was stirred at 0° C. for 30 min and at room temperature for 18 h. The reaction mixture was concentrated and a solution of EtOAc/hex (1:1) added. The reddish precipitate was collected by filtration and dried to give the desired product lxxxii (1.6 g) slightly impure. $^1$H NMR (DMSO-$d_6$) δ 10.87 (s, 1H), 0.94 (s, 1H), 8.71 (d, J=8.6 Hz, 1H), 8.84 (s, 1H), 8.24 (d, J=8.4 Hz, 1H), 8.1 (br s, 1H), 7.99 (br t, J=8.6 Hz, 1H), 7.88 (br t, J=8.4 Hz, 1H), 4.03 (s, 3H).

2.3 Preparation of 4-methyl-3-thiomethyl-1,2,4-triazo-5-yl-quinoline-4-carboxylic acid methyl ester.

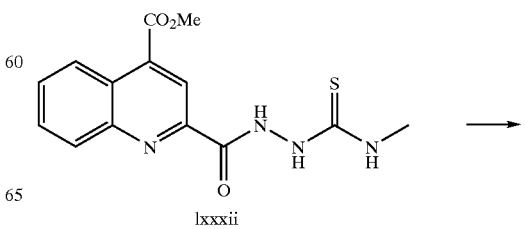

-continued

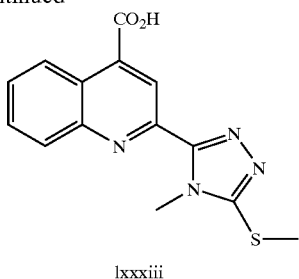

lxxxiii

Sodium metal (0.92 g, 40.2 mmol) was dissolved in 30 mL of dry MeOH. Intermediate lxxxii (1.6 g) was added and the reaction was refluxed for 18 h. The reaction was cooled to room temperature, the solvent was removed and the solid residue dissolved in water. The aqueous solution was acidified to pH 4–5 with 10% HCl, a solid precipitated which was collected by filtration, washed with water, and dried to give a triazolethione intermediate (1.09 g).

To a suspension of the triazolethione (1.09 g, 3.36 mmol) was added a 1.0 N solution of NaOH (3.63 mL, 3.63 mmol) and stirred for 10 min. Methyl iodide (0.24 mL, 3.8 mmol) was added and the reaction stirred for 18 h. The reaction was filtered and the filtrate concentrated to give the desired product lxxxiii. $^1$H NMR (DMSO-$d_6$) δ 8.74 (br d, J=8.4 Hz, 1H), 8.27 (s, 1H), 8.02 (br d, J=8.4 Hz, 1H), 7.74 (ddd, J=8.3, 6.8, 1.8 Hz, 1H), 7.56 (ddd, 8.3, 6.8, 1.3 Hz, 1H), 4.11 (s, 3H), 2.72 (s, 3H).

2.4 Preparation of Semithiocarbazone 2.1.

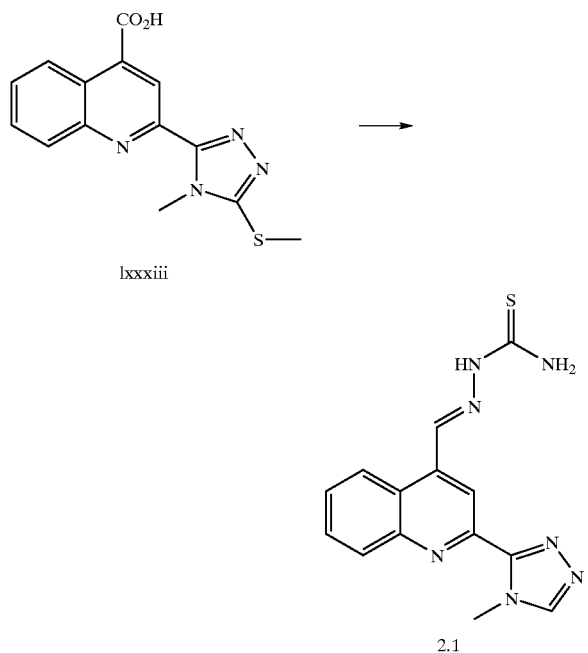

To a solution of the acid lxxxiii (750 mg, 2.5 mmol) in 20 mL of MEOH was added 2.0 mL of conc. $H_2SO_4$. The reaction was refluxed for 18 h. The reaction was cooled, the solvent removed in the rotavap, the residue diluted with water and the aqueous layer neutralized with solid $K_2CO_3$ to pH 8. The aqueous solution was extracted with EtOAc (3×) and $CH_2Cl_2$ (×). The organic layers were dried over $Na_2SO_4$, filtered and concentrated to give the corresponding methyl ester (500 mg).

A suspension of the ester (500 mg) and Raney Ni (75 mg) in 30 mL of EtOH was refluxed for 18 h. The reaction was cooled, filtered through Celite, and the filtrate was concentrated to give the desired product (300 mg).

The methyl ester (300 mg, 0.95 mmol) was dissolved in 10 mL of THF and cooled to −78° C. A 1.0 M solution of LiAlH$_4$ (3.0 mL, 3.0 mmol) in THF was added and the reaction was stirred until the ester was consumed (by TLC). The reaction quenched with 10% NH$_4$Cl at −78° C., brought to room temperature and aqueous extracted with EtOAc (3×). Organic layer dried over Na$_2$SO$_4$, filtered, and concentrated to dryness to give the desired alcohol (150 mg).

A suspension of the crude product (150 mg) and MnO$_2$ (750 mg) in 20 mL of THF was stirred at room temperature for 18 h. The suspension filtered through Celite, washed with EtOAc, and filtrate concentrated to dryness to give the desired aldehyde (60 mg).

A solution of the aldehyde (60 mg, 0.25 mmol) and semithiocarbazide (23 mg, 0.25 mmol) in 3 mL of EtOH was stirred at 70° C. for 18 h. The reaction cooled to room temperature, precipitate filtered, and dried to obtain the desired semithiocarbazone (19.2 mg). MS(ES) 312 (M$^+$+1).

Example 3

The following compounds were all prepared by similar methods to those described in Examples 1 and 2.

| Compound | Y | R$^1$ | R$^6$ | R$^7$ |
|---|---|---|---|---|
| 3.1 | S | CH$_3$ | —CH=CHCN | CH$_3$ |
| 3.2 | S | CH$_3$ | —CH=CHCN | H |
| 3.3 | S | CH$_3$ | —CH$_2$CH$_2$CN | H |
| 3.4 | S | H | —CH$_2$CH$_2$CN | H |
| 3.5 | O | H | —CH=CHCN | CH$_3$ |
| 3.6 | S | H | —CH=CHCN | CH$_3$ |
| 3.7 | S | CH$_3$ | —CH$_2$CH$_2$CN | CH$_3$ |
| 3.8 | S | H | —CH$_2$CH$_2$CN | CH$_3$ |
| 3.9 | S | H | —CH$_2$CH$_2$CN | CF$_3$ |
| 3.10 | S | CH$_3$ | —CH$_2$CH$_2$CN | CF$_3$ |
| 3.11 | S | n-butyl | —CH$_2$CH$_2$CN | CH$_3$ |
| 3.12 | S | CH$_3$ | —CH$_2$CH$_2$CN | —CH$_2$CH$_3$ |
| 3.13. | S | CH$_3$ | —CH$_2$CH$_2$SO$_2$CH$_3$ | CH$_3$ |
| 3.14 | S | CH$_3$ | —CH$_2$CH$_2$CN | Cl |
| 3.15 | S | CH$_3$ | —CH$_2$CH$_2$SO$_2$CH$_3$ | CF$_3$ |
| 3.16 | S | CH$_3$CH$_2$— | —CH$_2$CH$_2$CN | Cl |
| 3.17 | S | CF$_3$CH$_2$— | —CH$_2$CH$_2$CN | Cl |
| 3.18 | S | CH$_3$CH$_2$— | —CH$_2$CH$_2$CN | CF$_3$ |
| 3.19 | S | CH$_3$ | —CH$_2$CH$_2$CN | —CH$_2$CH$_2$CH$_3$ |
| 3.20 | S | CH$_3$ | —CH$_2$CH$_2$SO$_2$CH$_3$ | Cl |
| 3.21 | S | 2-methoxyethyl | —CH$_2$CH$_2$CN | CF$_3$ |
| 3.22 | S | 2-(4-morpholinyl)ethyl | —CH$_2$CH$_2$CN | Cl |
| 3.23 | S | 2-methoxyethyl | —CH$_2$CH$_2$CN | Cl |

-continued

Structure: quinoline with R6, R7 substituents; 2-(1-methylimidazol-5-yl); 4-position bears CH=N-N(R1)-C(=Y)-NH2

| Compound | Y | R¹ | R⁶ | R⁷ |
|---|---|---|---|---|
| 3.24 | S | 2-(4-morpholinyl)ethyl | —CH₂CH₂CN | H |
| 3.25 | S | tetrahydrofuran-3-ylmethyl | —CH₂CH₂CN | H |
| 3.26 | S | cyclopropyl-methyl | —CH₂CH₂CN | H |
| 3.27 | S | 2-(N,N-dimethyl-amino)ethyl | —CH₂CH₂CN | H |
| 3.28 | S | 2-(N,N-dimethyl-amino)ethyl | —CH₂CH₂CN | CF₃ |
| 3.29 | S | 2-(4-morpholinyl)ethyl | —CH₂CH₂CN | CF₃ |
| 3.30 | S | 3-hydroxypropyl | —CH₂CH₂CN | H |
| 3.31 | S | 2-hydroxyethyl | —CH₂CH₂CN | H |
| 3.32 | S | 2-(methoxy-carbonyl)ethyl | —CH₂CH₂CN | H |
| 3.33 | S | 2-hydroxypropyl | —CH₂CH₂CN | H |
| 3.34 | S | 2-(methyl-sulfonyl)ethyl | —CH₂CH₂CN | H |
| 3.35 | S | 2-(2-methoxy ethoxy)ethyl | —CH₂CH₂CN | CF₃ |
| 3.36 | S | 2,3-dihydroxypropyl | —CH₂CH₂CN | CF₃ |
| 3.37 | S | 2-(1-pyrrolidinyl)ethyl | —CH₂CH₂CN | CF₃ |
| 3.38 | S | 2-(N,N-dimethyl-amino)ethyl | —CH₂CH₂CN | Cl |
| 3.39 | S | 2-(1-pyrrolidinyl)ethyl | —CH₂CH₂CN | Cl |
| 3.40 | S | H | —CH₂CH₂CN | H |
| 3.41 | S | 2-(2-methoxy ethoxy)ethyl | —CH₂CH₂CN | H |
| 3.42 | S | CH₃CH₂ | —CH₂CH₂CN | H |
| 3.43 | S | CF₃CH₂ | —CH₂CH₂CN | H |
| 3.44 | S | 3-(1-piperidinyl)-prop-1-yl | —CH₂CH₂CN | H |
| 3.45 | S | 2-aminoethyl | —CH₂CH₂CN | H |
| 3.46 | S | 3-(N,N-dimethyl-amino)prop-1-yl | —CH₂CH₂CN | Cl |
| 3.47 | S | 3-(N,N-dimethyl-amino)prop-1-yl | —CH₂CH₂CN | H |
| 3.48 | S | H | F | H |
| 3.49 | S | H | CH₃ | H |
| 3.50 | S | CH₃ | F | H |
| 3.51 | S | CH₃ | CH₃ | H |
| 3.52 | S | H | CH₃O— | H |
| 3.53 | O | CH₃ | CH₃O— | H |
| 3.54 | O | CH₃ | H | H |
| 3.55 | S | H | Ph | H |
| 3.56 | O | H | Ph | H |
| 3.57 | O | H | CH₃O— | H |
| 3.58 | S | H | I | H |
| 3.59 | O | H | I | H |
| 3.60 | O | H | CN | H |
| 3.61 | S | H | —CH=CH₂ | H |
| 3.62 | S | H | H | CH₃ |
| 3.63 | O | H | H | CH₃ |
| 3.64 | O | H | —CH=CH₂ | H |
| 3.65 | S | H | 3-hydroxy-propyn-1-yl | H |
| 3.66 | S | H | Cl | H |
| 3.67 | O | H | Cl | H |
| 3.68 | S | H | 3-pyridyl | H |
| 3.69 | S | H | 2-thienyl | H |
| 3.70 | O | H | 3-hydroxy-propyn-1-yl | H |
| 3.71 | O | H | CH₃S— | H |
| 3.72 | O | H | CH₃SO₂— | H |
| 3.73 | O | H | H | CH₃O— |
| 3.74 | O | H | H | CH₃S— |
| 3.75 | O | H | H | CH₃SO₂— |
| 3.76 | O | H | H | Cl |
| 3.77 | O | H | H | F |
| 3.78 | S | H | H | Cl |
| 3.79 | NH | H | H | H |
| 3.80 | S | H | H | Br |
| 3.81 | O | H | H | Br |
| 3.82 | S | H | H | F |
| 3.83 | S | H | H | (CH₃)₂CH— |
| 3.84 | S | CH₃ | H | Cl |
| 3.85 | O | H | 1-methyl-imidazol-5-yl | H |
| 3.86 | O | H | —CH=CHCONH₂ | H |
| 3.87 | O | CH₃ | H | H |
| 3.88 | O | H | H | (CH₃)₂CH— |
| 3.89 | O | H | methylenedioxy | |
| 3.90 | S | CH₃ | H | CH₃ |
| 3.91 | O | H | NH₂ | H |
| 3.92 | O | H | —CH=CHCN | H |
| 3.93 | S | H | CH₃ | CH₃ |
| 3.94 | O | H | CH₃ | CH₃ |
| 3.95 | S | H | CH₃ | Cl |
| 3.96 | O | H | CH₃ | Cl |
| 3.97 | O | H | —CH₂CH₂CN | H |
| 3.98 | S | n-butyl | H | H |
| 3.99 | S | CH₃ | CH₃ | CH₃ |
| 3.100 | S | benzyl | H | H |
| 3.101 | S | CF₃CH₂— | H | H |
| 3.102 | S | CH₃ | 2-(4-morpholin-yl)ethoxy | H |
| 3.103 | O | H | Cl | CH₃ |
| 3.104 | S | H | Cl | CH₃ |
| 3.105 | S | CH₃ | Cl | CH₃ |
| 3.106 | S | H | 2-(4-morpholin-yl)ethoxy | H |
| 3.107 | S | 2-phenylethyl | H | H |
| 3.108 | S | CH₃ | —CH₂CH₂CN | H |
| 3.109 | S | H | CH₃SO₂CH=CH— | H |
| 3.110 | S | n-butyl | H | Cl |
| 3.111 | S | CH₃ | 1,2-dihydroxy-ethyl | |
| 3.112 | S | CH₃ | CH₃SO₂CH=CH— | H |
| 3.113 | S | CH₃ | 3-hydroxy-prop-1-yl | H |
| 3.114 | O | H | 4-hydroxy-but-1-yl | H |

-continued

[Structure: quinoline with R⁶ at 6-position, R⁷ at 7-position, 2-(1-methylimidazol-5-yl), and at 4-position a CH=N-N(R¹)-C(=Y)-NH₂ group]

| Compound | Y | R¹ | R⁶ | R⁷ |
|---|---|---|---|---|
| 3.115 | O | H | CH₃SO₂CH=CH— | H |
| 3.116 | S | CH₃ | CH₃SO₂CH₂CH₂— | H |
| 3.117 | O | H | CH₃SO₂CH₂CH₂— | H |
| 3.118 | S | CH₃ | 4-hydroxy-but-1-yn-1-yl | H |
| 3.119 | O | H | 4-hydroxy-but-1-yn-1-yl | H |
| 3.120 | S | CH₃ | 4-morpholinyl | H |
| 3.121 | S | CH₃ | 3-hydroxy-1-propenyl | H |
| 3.122 | S | n-butyl | —CH₂CH₂CN | H |
| 3.123 | S | H | 1,2-dihydroxy-ethyl | H |
| 3.124 | S | H | CH₃SO₂CH₂CH₂— | H |
| 3.125 | S | CH₃ | CH₃SO₂CH₂CH₂— | CH₃ |
| 3.126 | S | CH₃ | 2-(5-oxazolyl)-ethyl | H |

Example 4

The following compounds were all prepared by similar methods to those described in Examples 1 and 2.

[Structure: quinoline with B-ring at 2-position and at 4-position a CH=N-NH-C(=Y)-Z group]

| Compound | Y | Z | B-ring |
|---|---|---|---|
| 4.1 | S | —NHCH₃ | 1-methyl-1H-imidazol-5-yl |
| 4.2 | S | NH₂ | 1H-imidazol-5-yl |
| 4.3 | S | NH₂ | thiazol-5-yl |
| 4.4 | O | NH₂ | thiazol-5-yl |
| 4.5 | O | NH₂ | 1H-imidazol-5-yl |
| 4.6 | O | H | 1-methyl-1H-imidazol-5-yl |
| 4.7 | O | CH₃ | 1-methyl-1H-imidazol-5-yl |
| 4.8 | S | NH₂ | 1-methyl-1H-1,2,4-triazol-5-yl |

The following compounds have also been prepared:

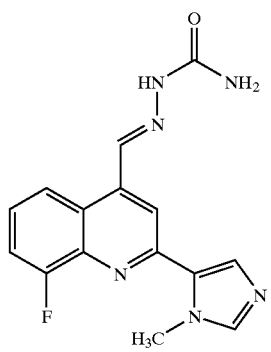

4.9

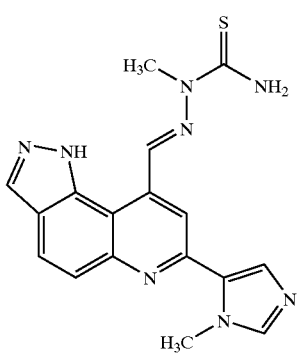

4.10

Example 5

5.1 Preparation of Hydrazine b

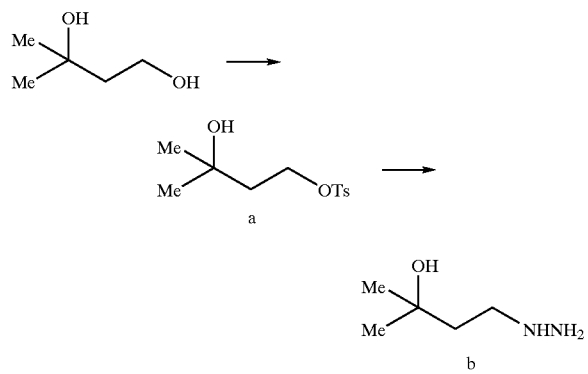

To a solution of 3-methyl-1,3-butanediol (Fluka, 6.14 mL, 57.6 mmol) in DCM (20 mL) at 0° C. under an atmosphere of nitrogen was added triethylamine (10 mL). p-Toluenesulfonyl chloride (11 g) in DCM (20 mL) was added dropwise over 4 h and the mixture was stirred for a further 3 h at 0° C., then allowed to warm to room temperature overnight. The reaction mixture was diluted with water (50 mL) and the organics were separated, washed with 1M HCl (50 mL), sat. aq. NaHCO$_3$ (50 mL) and water (20 mL). The organics were dried (Na$_2$SO$_4$), filtered and concentrated to afford tosylate a (13.4 g) as a white solid. $^1$H NMR (COCl$_3$) δ 7.81 (d, J=8 Hz, 2H), 7.37 (d, J=8 Hz, 2H), 4.22 (t, J=7 Hz, 2H), 2.47 (s, 3H), 1.88 (t, J=7 Hz, 2H), 1.23 (s, 6H).

To a solution of tosylate a (6.55 g, 25 mmol) in ethanol (10 mL) was added hydrazine monohydrate (15 mL) and the mixture was heated to 60° C. for 2 h then concentrated to approx. 10 mL volume. Saturated aq. sodium hydroxide (20 mL) and THF (50 mL) were added and the organics collected, dried (NaSO$_4$), filtered and concentrated to afford hydrazine b (1.8 g) as a colorless oil. ESI-MS m/z 119.3 (100, M+H$^+$). $^1$H NMR (CDCl$_3$) δ 4.73 (s, 1H), 3.19 (s, 3H), 3.02–3.06 (m, 2H), 1.68 (t, J=6 Hz, 2H), 1.26 (s, 6H).

5.2 Preparation of Semithiocarbazone 5

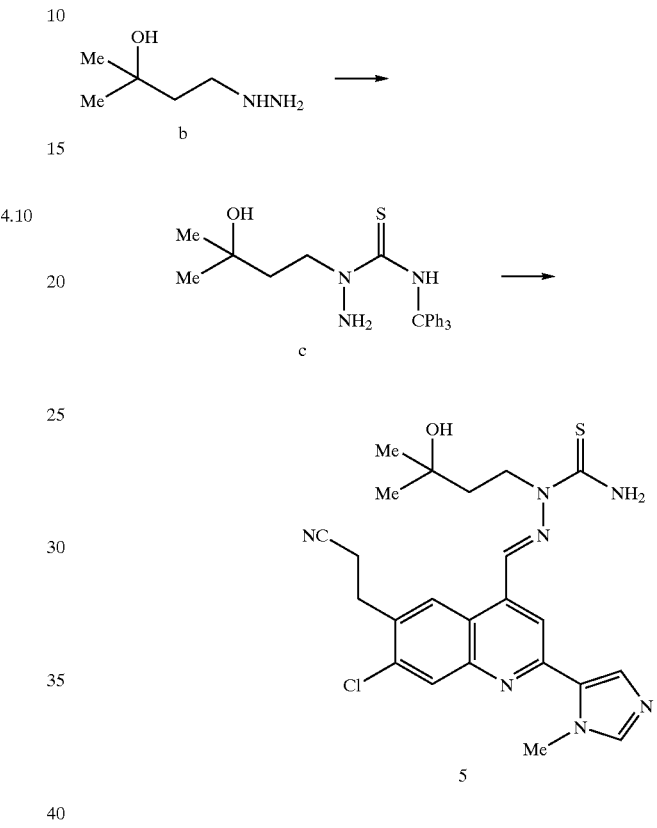

To a stirred solution of hydrazine b (0.8 g, 6.8 mmol) in diethyl ether (25 mL) was added triphenylmethylisothiocyanate (Trans World Chemicals, 1.83 g, 6.0 mmol). The mixture was stirred for 1 h and then hexanes (5 mL) was added and the mixture was filtered to afford semithiocarbazide c as a white solid (0.62 g). $^1$H NMR (CDCl$_3$) δ 9.51 (s, 1H), 7.21–7.36 (m, 15H), 4.27 (t, J=6.5 Hz, 2H), 4.01 (s, 2H), 2.43 (s, 1H), 1.82 (t, J=6.5 Hz, 2H), 1.26 (s, 6H).

To semithiocarbazide c (284 mg, 0.68 mmol) was added TFA:DCM/1:1 (5 mL). The mixture was stirred at room temperature for 2 h then concentrated in vacuo. Methanol (5 mL) was added and the mixture re-concentrated. This step was repeated 3 times until a white powder was obtained. Ethanol:water 4:1 (5 mL) and aldehyde C (prepared from 6-chloro-5-iodo-isatin by Method I and Method A) (199 mg, 0.61 mmol) were added and the reaction mixture was warmed to 65° C. overnight then cooled to room temperature and concentrated in vacuo. Flash chromatography of the residue (DCM:MeOH:NH$_3$/98:1:1 to 96:3:1; gradient elution) afforded the semithiocarbazone 5 as a yellow solid. ESI-MS m/z 484.1 (100, M+H$^+$). $^1$H NMR (DMSO-d$_6$) δ 8.72 (s, 1H), 8.69 (s, 1H), 8.60 (s, 1H), 8.53 (s, 1H), 8.43 (s, 1H), 8.17 (s, 1H), 8.07 (s, 1H), 7.88 (s, 1H) 4.95 (s, 1H), 4.79 (s, 2H), 4.15 (s, 3H), 3.24 (t, J=7 Hz, 2H), 2.98 (t, J=7 Hz, 2H), 1.73 (t, J=8 Hz, 2H), 1.27 (s, 6H).

Example 6

6.1a Preparation of 1-Methyl-2-piperidinemethanol (d)

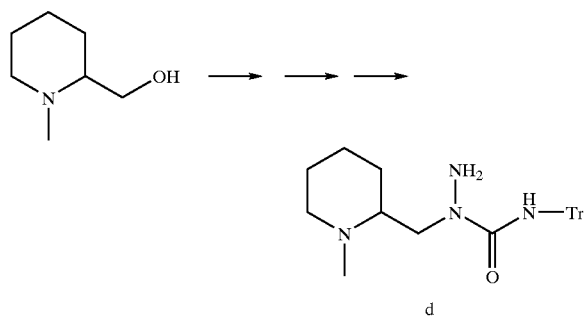

d

To a solution of 1-methyl-2-piperidinemethanol (20.75 mg, 160.6 mmol) in $CH_2Cl_2$ (100 mL) was added dropwise $SOCl_2$ (17.6 mL, 241 mmol). The solution was heated to reflux for 12 h. The solution was then concentrated under reduced pressure to provide 20 g which was used without further purification in the next step. The crude material was dissolved in EtOH (100 mL) and $NH_2NH_2$ (80 mL, 1.6 mol) was added. The solution was then heated to reflux for 12 h, cooled to room temperature and conc. NaOH solution (10 eq) was added, stirred for 1 h and extracted with ether. After evaporation of the ethereal layer the residue was distilled (reduced pressure) two fractions were recovered. Fraction 1 (95° C., 7.38 g). Fraction 2 (95–98° C., 1.39 g). The hydrazine (1.07 g, 7.5 mmol) was dissolved in THF (8 mL) and triphenylmethylisocyanate (2.16 g, 7.58 mmol) was added slowly. The solution was then stirred overnight and the product collected by filtration to provide 420 mg of the desired product as a yellow solid. $^1H$ NMR (DMSO-$d_6$): δ 1.10 (m, 2H), 1.30–1.56 (m, 4H), 1.95 (t, 1H), 2.15 (s, 1H), 2.18 (s, 3H), 2.71 (d, 1H), 3.25 (q, 1H), 3.55 (q, 1H), 4.80 (s, 2H), 7.12–7.32 (m, 15H), 8.02 (s, 1H). ESI-MS m/z 429.4 (100, M+H).

6.1b Preparation of (R)-(+)-1-Methyl-2-piperidinemethanol ((R)-d)

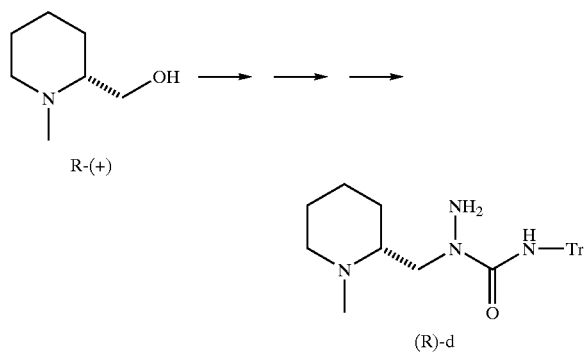

(R)-d

Following the known procedure of patent EP 0 429 984 A2 (reference example 8). The resolution was identical to the above given procedure except that 4 rounds of crystallization were performed instead of the two as sited above. To a mixture of (±)-1-methyl-2-piperidinemethanol (77 g, 596 mmol) in EtOH (615 mL) was added dibenzoyl-D-tartaric acid (205 g, 573 mmol). The resulting mixture was slowly heated until a solution was obtained at which time the solution was slowly cooled with gentle stirring. After 12 h the crystals were isolated and dried to afford 131.6 g. This process was repeated: (2) EtOH (533 mL) provided 92.5 g. (3) EtOH (225 mL) provided 68 g (4) EtOH (200 mL) provided 49 g. The resulting salt was treated with 3M HCl (200 mL) which was heated to induce it to dissolve. The still warm solution was poured into a separatory funnel and extracted with ethyl acetate. The remaining aqueous layer was adjusted to pH 10 with $K_2CO_3$. The solution was extracted with $CH_2Cl_2$, dried ($MgSO_4$) and concentrated to give 12 g of the alcohol. This alcohol (12 g, 92.8 mmol) was suspended in $CH_2Cl_2$ (200 mL) and $SOCl_2$ added. After stirring for 12 h, the solvent was removed to provide a crude HCl salt. This salt was dissolved in EtOH (100 mL) and treated with $NH_2NH_2$ (89 mL, 1.86 mol) and heated to reflux for 12 h. NaOH (74 g) in H2O (30 mL) was added and stirred for 1 h. Half the solvent was removed and the residue extracted with ether to give a crude oil. After distillation under reduced pressure (50–60° C.) the pure hydrazine product (4.87 g) was obtained. This hydrazine (1.6 g, 11.2 mmol) was dissolved in THF (10 mL) and triphenylmethylisocyanate (3.19 g, 11.2 mmol) was added slowly. The solution was then stirred overnight and filtered to provide 650 mg of the desired product in good purity. $^1H$ NMR (DMSO-$d_6$): δ 1.10 (m, 2H), 1.30–1.56 (m, 4H), 1.95 (t, 1H), 2.15 (s, 1H), 2.18 (s, 3H), 2.71 (d, 1H), 3.25 (q, 1H), 3.55 (q, 1H), 4.80 (s, 2H), 7.12–7.32 (m, 15H), 8.02 (s, 1H). ESI-MS m/z 429.2 (100, M+H).

6.1c Preparation of (S)-(−)-1-Methyl-2-piperidinemethanol ((S)-d)

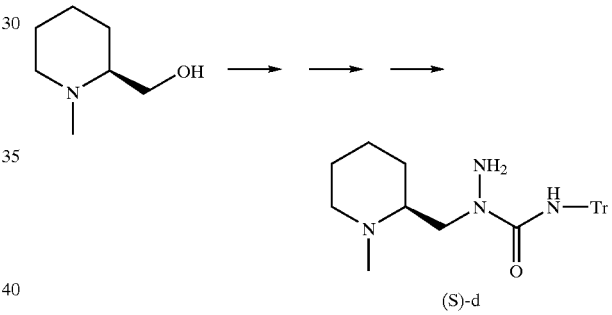

(S)-d

Following the known procedure of patent EP 0 429 984 A2 (reference example 8). The resolution was identical to the procedure described above except 3 rounds of crystallization were performed. To a mixture of (±)-1-methyl-2-piperidinemethanol (95.6 g, 740 mmol) in EtOH (840 mL) was added dibenzoyl-L-tartaric acid (255 g, 711 mmol). The resulting mixture was slowly heated until a solution was obtained at which time the solution was slowly cooled with gentle stirring. After 12 h the crystals were isolated and dried to provide 79.6 g. This process was repeated: (2) EtOH (335 mL) provided 50.4 g. (3) EtOH (345 mL) provided 35 g. The resulting salt was treated with 3M HCl (134 mL) which was heated to induce it to dissolve. The still warm solution was poured into a separatory funnel and extracted with ethyl acetate. The remaining aqueous layer was adjusted to pH 10 with $K_2CO_3$. The solution was extracted with $CH_2Cl_2$, dried ($MgSO_4$) and concentrated to give 6 g of the alcohol. This alcohol (6 g, 46.7 mmol) was suspended in $CH_2Cl_2$ (100 mL) and $SOCl_2$ (6.8 mL, 93.3 mmol) added dropwise. After stirring for 12 h, the solvent was removed to provide a crude HCl salt. This salt (5.98 g) was dissolved in EtOH (100 mL) and treated with $NH_2NH_2$ (19.5 mL, 405 mmol) and heated to reflux for 3 h. Half the solvent was removed, the residue extracted with ether and the extracts dried and concentrated to give 4.55 g of a crude oil. This crude hydrazine (2.01 g, 14.06 mmol) was dissolved in THF (100 mL) and triphenyl-methylisocyanate (4.0 g, 14.1 mmol) was added slowly. The solution was then stirred overnight and the solvent removed under reduced pressure and the residue was purified by flash chromatography (CH$_2$Cl$_2$/MeOH/NH$_4$OH) to provide 350 mg of the desired product. $^1$H NMR (DMSO-d$_6$) δ 1.10 (m, 2H), 1.30–1.56 (m, 4H), 1.95 (t, 1H), 2.15 (s, 1H), 2.18 (s, 3H), 2.71 (d, 1H), 3.25 (q, 1H), 3.55 (q, 1H), 4.80 (s, 2H), 7.12–7.32 (m, 15H), 8.02 (s, H). ESI-MS m/z 429.2 (100, M+H).

6.2a. Preparation of Semicarbazide 6

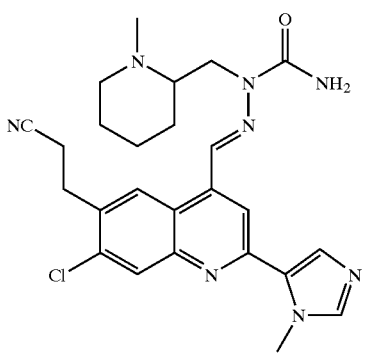

6

Compound 6 was prepared from carbazide d and aldehyde C (prepared from 6-chloro-5-iodo-isatin by Method I and Method A) by the procedure described in Example 5. $^1$H NMR (DMSO-d$_6$) δ 1.10–1.20 (m, 2H), 1.49 (m, 3H), 1.65 (m, 1H), 2.15 (t, 1H), 2.43 (s, 3H), 2.83 (d, 1H), 3.00 (t, 2H), 3.23 (t, 2H), 4.09 (s, 1H), 4.13 (s, 3H), 4.23 (q, 1H), 4.31 (q, 1H), 6.80–7.40 (s, 2H), 7.85 (s, 1H), 8.04 (s, 1H), 8.14 (s, 1H), 8.38 (s, 1H), 8.41 (s, 1H), 8.45 (s, 1H). ESI-MS m/z 493.2 (100, M+H).

6.2b Preparation of Semicarbazide (S)-(−)-6

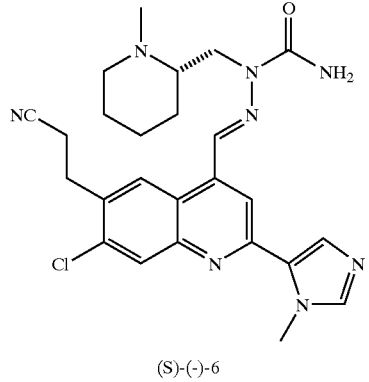

(S)-(−)-6

Compound (S)-(−)-6 was prepared from carbazide (S)-d and aldehyde C (prepared from 6-chloro-5-iodo-isatin by Method I and Method A) by the procedure described in Example 5. $^1$H NMR (DMSO-d$_6$) δ 1.10–1.30 (m, 2H), 1.49 (m, 3H), 1.64 (m, 1H), 2.09 (t, 1H), 2.38 (s, 1H), 2.41 (s, 3H), 2.83 (d, 1H), 3.00 (dd, 2H), 3.23 (dd, 2H), 4.13 (s, 3H), 4.18 (q, 1H), 4.31 (q, 1H), 6.90 (s, 1H), 7.30 (s, 1H), 7.85 (s, 1H), 8.04 (s, 1H), 8.14 (s, 1H), 8.38 (s, 1H), 8.41 (s, 1H), 8.45 (s, 1H). ESI-MS m/z 493.2 (100, M+H).

6.2c Preparation of Semicarbazide (R)-(+)-6

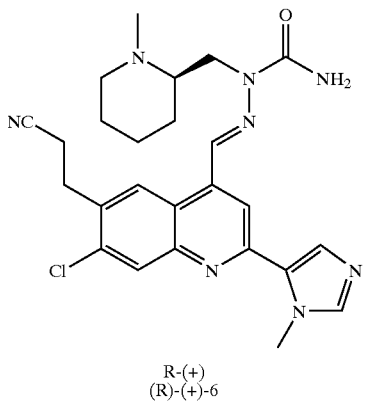

R-(+)
(R)-(+)-6

Compound (R)-(+)-6 was prepared from carbazide (R)-d and aldehyde C (prepared from 6-chloro-5-iodo-isatin by Method I and Method A) by the procedure described in Example 5. $^1$H NMR (DMSO-d$_6$) δ 1.10–1.30 (m, 2H), 1.49 (m, 3H), 1.64 (m, 1H), 2.09 (t, 1H), 2.38 (s, 1H), 2.41 (s, 3H), 2.83 (d, 1H), 3.00 (dd, 2H), 3.23 (dd, 2H), 4.13 (s, 3H), 4.18 (q, 1H), 4.31 (q, 1H), 6.90 (s, 1H), 7.30 (s, 1H), 7.85 (s, 1H), 8.04 (s, 1H), 8.14 (s, 1H), 8.38 (s, 1H), 8.41 (s, 1H), 8.45 (s, 1H). ESI-MS m/z 493.2 (100, M+H).

Example 7

7.1 Preparation of Ester f

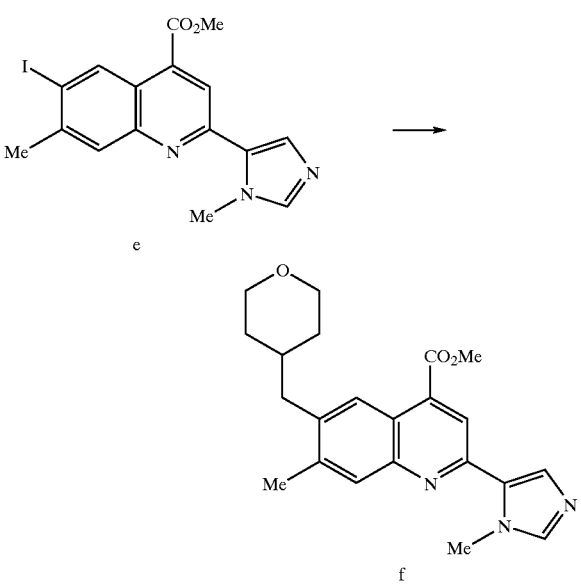

A suspension of zinc metal (1.70 g, 26.2 mmol) in THF (2 mL) containing 1,2-dibromoethane (190 mg, 1.0 mmol) was heated to 65° C. for one minute, cooled to room temperature and treated with TMSCl (0.10 mL, 0.80 mmol). After 15 min at room temperature, a warm solution of 4-iodomethyltetrahydropyran (5.65 g, 25.0 mmol) in THF (10 mL) was added dropwise. Upon completion of the addition, the reaction mixture was heated to 40° C. for 12 h and then cooled to room temperature. The resulting clear solution was transferred via cannula to a solution of iodoquinoline e (2.0 g, 5.0 mmol) in THF (100 mL) containing (dppf)$_2$PdCl$_2$ (600 mg) and heated to reflux for 10 h.

The reaction mixture was treated with aq. disodium EDTA, extracted with DCM (4×100 mL) and dried (Na₂SO₄). Concentration followed by flash chromatography (EtOAc:hexanes:MeOH/4:4:1) afforded f as a yellow solid (1.28 g). MS (M+1)⁺: 380. ¹H NMR (CDCl₃): δ 8.51 (s, 1H), 8.12 (s, 1H), 7.90 (s, 1H), 4.34 (s, 3H), 4.07 (s, 3H), 3.97 (dd, J=11.0, 2.7 Hz, 2H), 3.35 (t, J=10.1 Hz, 2H), 2.79 (d, J=7.0 Hz, 2H), 2.55 (s, 3H), 1.80–1.90 (m, 1H), 1.60–1.63 (m, 2H), 1.40–1.50 (m, 2H).

7.2 Preparation of Semithiocarbazone 7

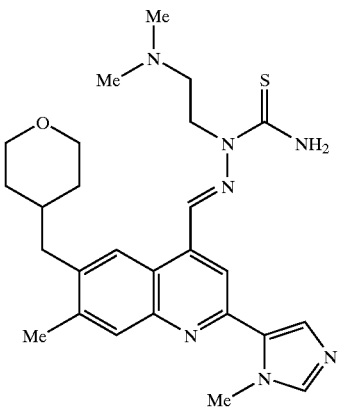

Ester f was converted into compound 7. MS (M+1)⁺: 494. ¹H NMR (DMSO-d₆): δ 8.69 (s, 1H), 8.67 (s, 1H), 8.49 (s, 1H), 8.37 (s, 1H), 8.05 (s, 1H), 7.92 (s, 1H), 7.84 (s, 1H), 7.81 (s, 1H), 4.75–4.85 (m, 2H), 4.11 (s, 3H), 3.80–3.83 (m, 2H), 3.20–3.24 (m, 2H), 2.73 (d, J=6.5 Hz, 2H), 2.34 (s, 6H), 1.77–1.85 (m, 1H), 1.33–1.51 (m, 2H), 1.29–1.32 (m, 2H).

Example 8

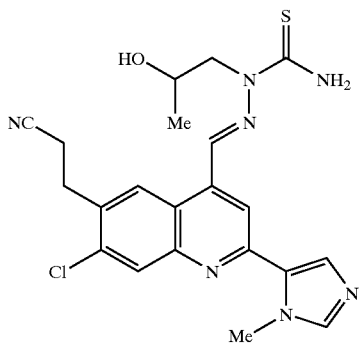

Compound 8 was prepared from 2-hydroxypropylhydrazine (obtained following the method of Gever *J. Am. Chem. Soc.* 1954, 76, 1283) and aldehyde C (prepared from 6-chloro-5-iodo-isatin by Method I and Method A) following the methods in Example 5. MS (M+1)⁺: 456. ¹H NMR (DMSO-d₆): δ 8.91 (s, 1H), 8.68 (s, 1H), 8.53 (s, 1H), 8.43 (s, 1H), 8.39 (s, 1H), 8.15 (s, 1H), 8.01 (s, 1H), 7.86 (s, 1H), 5.13 (d, J=4.6 Hz, 1H), 4.81–4.88 (m, 1H), 4.42–4.48 (m, 1H), 4.15–4.19 (m, 1H), 4.12 (s, 3H), 3.23 (t, J=7.1 Hz, 2H), 2.96 (t, J=7.8 Hz, 2H), 1.20 (d, J=6.2 Hz, 3H).

Example 9

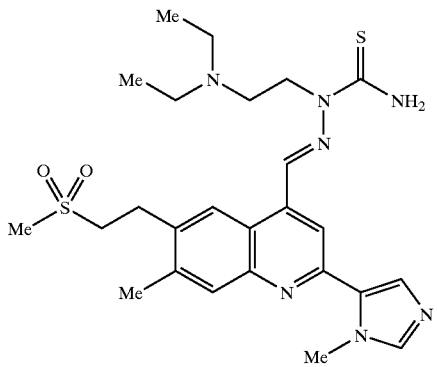

Compound 9 was obtained as a yellow solid. ESI-MS m/z 530.3 (100, M+H⁺). ¹H NMR (DMSO-d₆) δ 8.75 (s, 1H), 8.73 (s, 1H), 8.58 (s, 1H), 8.43 (s, 1H), 8.22 (s, 1H), 7.97 (s, 1H), 7.89 (s, 1H), 7.84 (s, 1H), 4.76 (t, J=6 Hz, 2H), 4.14 (s, 3H), 3.38–3.48 (m, 2H), 3.19–3.27 (m, 2H), 3.08 (s, 3H), 2.71 (t, J=6 Hz, 2H), 2.60 (q, J=7 Hz, 4H), 2.56 (s, 3H), 1.05 (t, J=7 Hz, 6H).

Example 10

10.1 Preparation of Hydrazine h

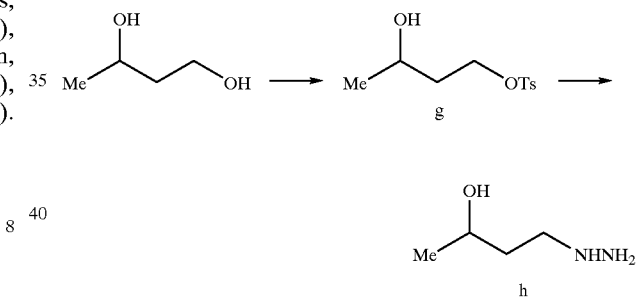

To a stirred solution of R-(–)-1,3-butanediol (Aldrich, 5.00 g, 55.5 mmol) in dichloromethane (20 mL) at –20° C. under an atmosphere of nitrogen was added triethylamine (10 mL). p-Toluenesulfonyl chloride (10.6 g) in a solution in dichloromethane (30 mL) was added dropwise over 2 h and the mixture was stirred for a further 2 h at –20° C. then allowed to warm to room temperature overnight. The mixture was diluted with water (50 mL) and the organics were separated, washed with 1M HCl (50 mL), sat. aq. sodium bicarbonate (50 mL) and brine (20 mL). The organics were dried (Na₂SO₄); filtered and concentrated to afford the crude tosylate g. Tosylate g was added dropwise over 30 min to a stirred solution of hydrazine monohydrate (30 mL) and ethanol (30 mL) at 75° C. The mixture was stirred at 75° C. overnight and then concentrated in vacuo. Water (20 mL) was added and the mixture extracted with DCM by continuous extraction for 48 h. The organics extracts were concentrated in vacuo to afford hydrazine b (3.0 g for 2 steps) as a colorless oil. ¹H NMR (CDCl₃) δ 3.95–3.98 (m, 2H), 3.43 (br s, 4H), 2.97–3.04 (m, 2H), 1.61–1.68 (m, 2H), 1.91–1.20 (s, 3H). ESI-MS m/z 105.2 (100, M+H⁺).

10.2 Preparation of Semithiocarbazone 10

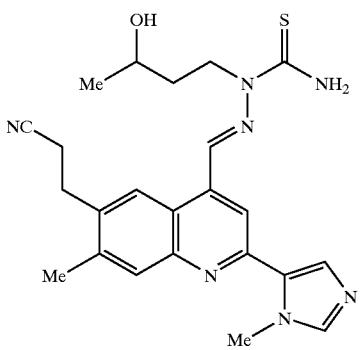

Hydrazine h and aldehyde M (prepared from 6-chloro-5-iodo-isatin by Method I and Method A) were converted in to semithiocarbazone 10 as described in Example 5. $^1$H NMR (DMSO-$d_6$) δ 1.19 (d, J=7 Hz, 3H), 1.55–1.85 (m, 2H), 2.98 (t, J=7 Hz, 2H), 3.23 (t, J=7 Hz, 2H), 3.75–3.85 (m, 1H), 4.14 (s, 3H), 4.55–4.69 (m, 1H), 4.80–4.95 (m, 1H), 5.02 (d, J=4 Hz, 1H) 7.39 (s, 1H), 7.85 (s, 1H), 7.98 (s, 1H), 8.25 (s, 1H), 8.40 (s, 1H), 8.52 (s, 1H), 8.59 (s, 1H), 8.73 (s, 1H). ESI-MS m/z 450.2 (100, M+H$^+$).

Example 11

11.1 Preparation of Acid j

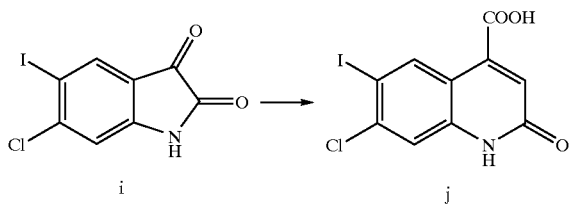

To a stirred solution of isatin i (30.0 g, 96.7 mmol) in glacial acetic acid (500 mL) at room temperature was added malonic acid (104 g, 387 mmol). The mixture was heated at 100° C. for 18 h then cooled to room temperature, filtered and washed with acetone (3×100 mL) to yield acid j as an orange solid (14.4 g). $^1$H NMR (DMSO-$d_6$) δ 12.18 (s, 1H), 8.82 (s, 1H), 7.50 (s, 1H), 6.92 (s, 1H).

11.2 Preparation of Ester k

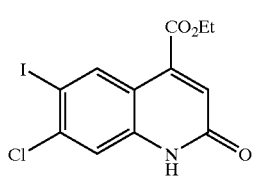

To a stirred solution of acid j (9.0 g, 26 mmol) and K$_2$CO$_3$ (5.3 g, 39 mmol) in anhydrous DMF (200 mL) under an atmosphere of nitrogen was added iodoethane (8.0 g, 52 mmol). The mixture was stirred at room temperature for 18 h then poured into saturated sodium bicarbonate solution (250 mL), filtered and washed with H$_2$O (3×150 mL) to yield ester k as a brown solid (7.0 g, 72%). $^1$H NMR (DMSO-$d_6$) δ 8.65 (s, 1H), 7.52 (s, 1H), 6.98 (s, 1H) 4.20 (q, J=7 Hz, 2H), 1.18 (t, J=7 Hz, 3H).

11.3 Preparation of Chloride I

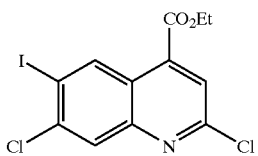

To a stirred solution of ester k (10.0 g, 26.5 mmol) in toluene (300 mL) was added phosphorous oxychloride (16.2 g, 106 mmol). The mixture was heated to 100° C. under an atmosphere of nitrogen for 18 h then allowed to cool to room temperature, poured into ice water (500 mL), filtered and washed with H$_2$O (2×250 mL) to yield chloride I as a brown solid (5.3 g). $^1$H NMR (DMSO$_6$) δ 9.25 (s, 1H), 8.24 (s, 1H), 7.99 (s, 1H), 4.43 (q, J=7 Hz, 2H), 1.38 (t, J=7 Hz, 3H). ESI-MS: m/z 395.9 (100%, M+H$^+$).

11.4 Preparation of Intermediate m

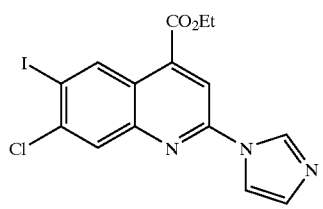

To a stirred solution of chloride I (4.0 g, 10 mmol) in anhydrous DMF (15 mL) was added imidazole (3.4 g, 51 mmol) and the mixture heated at 140° C. for 18 h under an atmosphere of nitrogen. The mixture was cooled to room temperature and then concentrated in vacuo to afford a dark oil. The residue was dissolved in CHCl$_3$ (150 mL) washed with H$_2$O, saturated sodium bicarbonate solution, brine, dried over MgSO$_4$, filtered and concentrated. The residue was purified by flash chromatography (eluting with 2% MeOH in DCM) to yield m as a red brown solid (3.5 g, 81%). $^1$H NMR (DMSO-$d_6$) δ 9.17 (s, 1H), 8.81 (s, 1H), 8.39 (s, 1H), 8.22 (s, 1H), 8.18 (s, 1H), 7.21 (s, 1H), 4.56 (q, J=7 Hz, 2H), 1.48 (t, J=7 Hz, 3H).

11.5 Preparation of Intermediate n

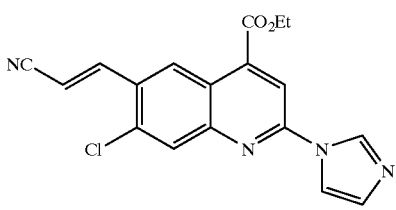

To a stirred solution of m (2.0 g, 4.7 mmol), Pd(OAc)$_2$ (210 mg, 0.94 mmol) and tri-o-tolylphosphine (640 mg, 2.10 mmol) in 1:1/triethylamine:DMF (20 mL) under an atmosphere of nitrogen at room temperature was added acrylonitrile (1.24 g, 23.4 mmol). The mixture was heated to 60° C. for 18 h, cooled to room temperature, concentrated in vacuo and the residue purified by flash chromatography (gradient elution 0 to 5% MeOH in DCM) to yield product n (730 mg) as a yellow solid and a mixture of 1:5 cis:trans isomers. $^1$H NMR (DMSO-$d_6$) δ 9.15 (cis, s, 2H), 8.85 (trans, s, 2H), 8.45 (cis, s, 1H), 8.42 (trans, s, 1H), 8.29 (cis, s, 1H), 8.25–8.20 (cis+trans, m, 1H cis, 2H trans), 8.00 (trans, d, J=16 Hz, 1H), 7.81 (cis, d, J=12 Hz, 1H), 7.23 (cis+trans, s, 1H cis, 1H trans), 6.62 (trans, d, J=16 Hz, 1H), 6.3 (cis, d, J=12 Hz, 1H), 4.58–4.5 (cis+trans, m, 2H cis, 2H trans), 1.5–1.41 (cis+trans, m, 3H cis, 3H trans).

11.6 Preparation of Intermediate o

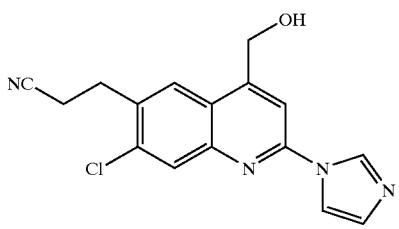

To a stirred solution of n (740 mg, 2.10 mmol) in DME (10 mL) and MeOH (1 mL) under an atmosphere of nitrogen at room temperature was added sodium borohydride powder (800 mg, 21.0 mmol) portionwise over 1 h. The mixture was allowed to stir for 20 h then cooled to 0° C., quenched with 1N NaOH (10 mL), diluted with $H_2O$ (10 mL) and allowed to stir at room temperature for 2 h. The mixture was filtered, and the filtrate extracted with 10% isopropyl alcohol in DCM (×3). The organics were combined, dried over $MgSO_4$, filtered and concentrated. The residue was purified by flash chromatography (gradient elution 0 to 5% MeOH in DCM) to yield alcohol o as a pale yellow solid (260 mg). $^1$H NMR (DMSO-$d_6$) δ 8.70 (s, 1H), 8.14 (s, 1H), 8.13 (s, 1H), 8.09 (s, 1H), 7.20 (s, 1H), 5.08 (s, 2H), 3.25 (t, J=7 Hz, 2H), 2.99 (t, J=7 Hz, 2H). ESI-MS m/z 313.0 (100%, M+H$^+$).

11.7 Preparation of Intermediate p

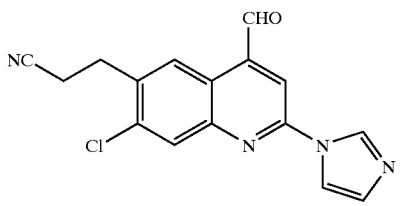

To a stirred solution of alcohol o (260 mg, 0.83 mmol) in DCM (10 mL) under an atmosphere of nitrogen at room temperature was added Dess-Martin periodinane (707 mg, 1.66 mmol). After 2 h the mixture was diluted with 5 mL saturated ammonium chloride solution and extracted with DCM (3×). The combined organic extracts were washed with saturated sodium thiosulfate solution (2×10 mL), $H_2O$, brine, dried over $MgSO_4$, filtered and concentrated. The residue was purified by flash chromatography (gradient elution 0 to 5% MeOH in DCM) to yield 80 mg of aldehyde p as a yellow solid. $^1$H NMR (DMSO-$d_6$) δ 10.52 (s, 1H), 8.96 (s, 1H), 8.61 (s, 1H), 8.20 (s, 1H), 7.95 (s, 1H), 7.89 (s, 1H), 7.38 (s, 1H), 3.34 (t, J=7 Hz, 2H), 2.81 (t, J=7 Hz, 2H).

11.8 Preparation of Semiothiocarbazone 11

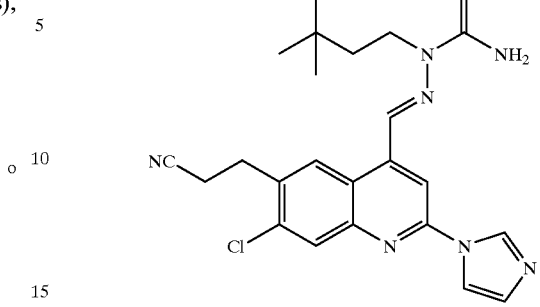

Compound 11 was prepared following the procedure described in Example 5. $^1$H NMR (DMSO-$d_6$) δ 8.32 (s, 1H), 8.86 (s, 1H), 8.67 (s, 1H), 8.61 (s, 1H), 8.5 (s, 1H), 8.36 (s, 1H), 8.32 (s, 1H), 8.18 (s, 1H), 7.44 (s, 1H), 5.05 (s, 1H), 4.81–4.79 (m, 2H), 3.24 (t, J=7 Hz, 2H), 2.99 (t, J=7 Hz, 2H), 1.72 (t, J=7 Hz, 2H), 1.28 (s, 6H). ESI-MS m/z 470.2 (150, M+H$^+$)

Example 12

This example provides an assay that is useful in evaluating and selecting a compound that modulates IKK.

Assay Protocol for Measuring IKKβ Enzyme Inhibition 96 well polystyrene microtiter plates were coated with Neutravidin (10 μg/mL in PBS, overnight at 4° C.). The coating solution was removed and in 80 μL/well a kinase reaction mixture was added (20 mM Tris-HCl, pH 7.5, 10 mM $MgCl_2$, 2 mM EGTA, 1 mM NaF, 0.5 mM benzamidine, 1 mM DTT, 0.1% NP-40, 10 μM ATP, 1μM of biotinylated substrate peptide KKERLLDDRHDSGLDSMKDEE YEQGK-bio, sequence derived from IκBα). In 10 μL/well in DMSO test compounds were added covering a final concentration range from 1 nM to 30 μM. Recombinant full-length IKKβ enzyme produced in a baculovirus system in insect cells was added in 10 μL buffer containing Tris-HCl pH 7.5 20 mM, EGTA 2 mM, benzamidine 0.5 mM, DTT 1 mM, NP-40 0.1%, $MgCl_2$ 10 mM to initiate the kinase reaction. The reaction mixture was incubated at room temperature for 45 min. During this incubation the substrate peptide gets phosphorylated by IKKβ and gets captured onto the well's surface by Neutravidin. The plate was washed 3× with 150 μL distilled water to terminate the reaction and remove components of the reaction mixture.

A conventional chemiluminescent ELISA detection technique was initiated by adding 100 μL/well primary antibody (custom-made monoclonal antibody generated to recognize the phosphorylated epitope in the substrate peptide; used at 1:10,000 dilution) premixed with horseradish peroxidase (HRP) conjugated anti-mouse secondary antibody (commercially available from several sources; used at 1:10,000 dilution) in PBS containing 2% BSA. The solution was incubated at room temperature for 40 min on a shaker, then washed 3× with 150 μL of water. 100 μL/well 10× diluted SuperSignal HRP substrate (from Pierce) was added and after 5 min incubation the chemiluminescent signal was captured by a Labsystems LuminoSkan luminometer. The point of 50% inhibition of IKKβ enzyme activity ($IC_{50}$) was determined by curve fitting with the LSW data analysis software (MDL, San Leandro, Calif.).

The compounds provided in Examples 1–4 all displayed $IC_{50}$ values of less than or equal to about 30 μM in the above assay.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

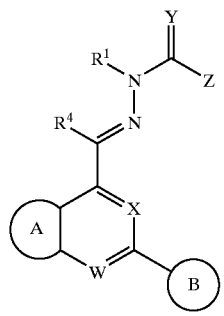

wherein

W is N;

X is CH;

Y is selected from the group consisting of O, S and N(R);

wherein R is selected from the group consisting of H, CN, $NO_2$, $(C_1-C_{10})$alkyl, $(C_3-C_{10})$cycloalkyl, $(C_4-C_{10})$cycloalkyl-alkyl, $(C_3-C_{10})$alkenyl and $(C_2-C_{10})$alkynyl;

Z is selected from the group consisting of H, $(C_1-C_{10})$alkyl, $(C_3-C_{10})$cycloalkyl, $(C_4-C_{10})$cycloalkyl-alkyl, $(C_2-C_{10})$alkenyl, $(C_2-C_{10})$alkynyl and $NR^2R^3$;

$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_1-C_{10})$heteroalkyl, $(C_3-C_{10})$cycloalkyl, $(C_4-C_{10})$cycloalkyl-alkyl, $(C_3-C_{10})$cycloheteroalkyl-alkyl, $(C_3-C_{10})$cycloheteroalkyl, aryl, aryl$(C_1-C_4)$alkyl, aryl$(C_1-C_4)$heteroalkyl, heteroaryl$(C_1-C_4)$alkyl, heteroaryl$(C_1-C_4)$heteroalkyl and perfluoro$(C_1-C_6)$alkyl; and wherein when Z is $NR^2R^3$, $R^2$ and $R^3$ can be combined to form a 5- to 7-membered heterocyclyl ring;

$R^4$ is selected from the group consisting of H, $(C_1-C_6)$alkyl, $(C_3-C_6)$cycloalkyl, $(C_4-C_7)$cycloalkyl-alkyl, $(C_2-C_6)$alkenyl and $(C_2-C_6)$alkynyl;

A is a substituted or unsubstituted 6-membered fused carbocyclic or heterocyclic aromatic ring system, wherein the heterocyclic aromatic ring system contains 1–2 N atoms; and B is a substituted or unsubstituted five- or six-membered ring which is aromatic, containing at least one nitrogen atom, and from 0 to 3 additional heteroatoms, wherein the B ring substituents are selected from the group consisting of halogen, $CF_3$, $CF_3O$, $(C_1-C_6)$alkyl, perfluoro$(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_4-C_{10})$cycloalkyl-alkyl, $(C_3-C_{10})$cycloheteroalkyl, cyano, nitro, sulfonamido, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, carboxamido and $(C_1-C_6)$heteroalkoxyl;

or pharmaceutically acceptable salts thereof.

2. A compound of claim 1, wherein Y is selected from the group consisting of O and S.

3. A compound of claim 1, wherein Y is O.

4. A compound of claim 1, wherein Y is S.

5. A compound of claim 1, wherein Z is $NR^2R^3$.

6. A compound of claim 2, wherein $R^4$ is H.

7. A compound of claim 1, wherein A is selected from the group consisting of:

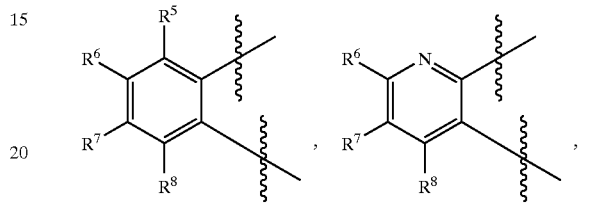

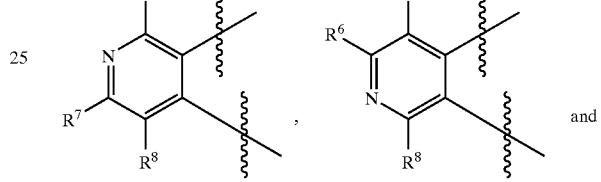

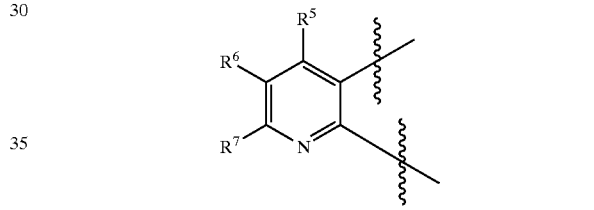

wherein $R^5$, $R^6$, $R^7$ and $R^8$ are independently selected from the group consisting of H, halogen, $CF_3$, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$alkylamino, di$(C_1-C_6)$alkylamino, $(C_3-C_{10})$cycloalkyl, $(C_4-C_{10})$cycloalkyl-alkyl, $(C_3-C_{10})$cycloheteroalkyl, $(C_3-C_{10})$cycloheteroalkyl-alkyl, cyano, nitro, $(C_1-C_6)$acyl, $(C_1-C_6)$acylamino, $(C_1-C_6)$alkoxycarbonyl, $(C_1-C_6)$alkoxycarbonyl $(C_1-C_6)$alkyl, $CONH_2$, $CO-NH-(C_1-C_6)$alkyl, $CO-N[(C_1-C_6)$alkyl$]_2$, $SO_2NH_2$, $SO_2NH-(C_1-C_6)$alkyl, $SO_2N-[(C_1-C_6)$alkyl$]_2$ and $(C_1-C_6)$heteroalkoxy; or two adjacent R groups selected from $R^5$, $R^6$, $R^7$ and $R^8$, can be linked together to form a new 5- or 6-membered carbocyclic or heterocyclic ring.

8. A compound of claim 7, wherein Y is O or S; and A is selected from the group consisting of:

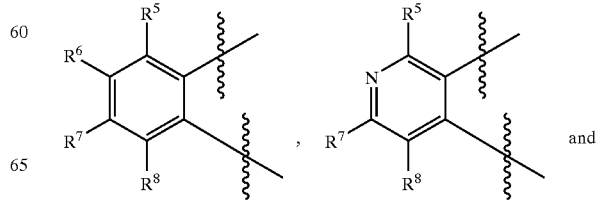

-continued

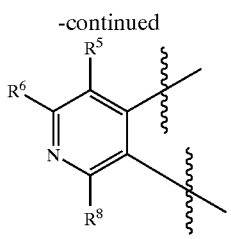

9. A compound of claim 1, wherein B contains a nitrogen atom at a position two atoms away from the atom attaching B to the remainder of the molecule.

10. A compound of claim 1, wherein B contains a nitrogen atom at the point of attachment of B to the remainder of the molecule.

11. A compound of claim 1, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

12. A compound of claim 1, wherein B is selected from the group consisting of substituted or unsubstituted imidazolyl, substituted or unsubstituted thiazolyl and substituted or unsubstituted triazolyl.

13. A compound of claim 8, wherein B contains a nitrogen atom at a position two atoms away from the atom attaching B to the remainder of the molecule.

14. A compound of claim 8, wherein B contains a nitrogen atom at the point of attachment of B to the remainder of the molecule.

15. A compound of claim 8, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

16. A compound of claim 8, wherein B is selected from the group consisting of substituted or unsubstituted imidazolyl, substituted or unsubstituted thiazolyl and substituted or unsubstituted triazolyl.

17. A compound of claim 1, wherein Y is O or S; Z is H, $CH_3$, $NH_2$ or $NHCH_3$; $R^1$ is H, $(C_1-C_6)$alkyl, $(C_1-C_{10})$heteroalkyl, $(C_4-C_{10})$cycloheteroalkyl-alkyl, $(C_3-C_{10})$cycloheteroalkyl, aryl$(C_1-C_4)$alkyl, aryl$(C_1-C_4)$heteroalkyl, heteroaryl$(C_1-C_4)$alkyl, heteroaryl$(C_1-C_4)$heteroalkyl, or perfluoro$(C_1-C_6)$alkyl; $R^4$ is H; A represents

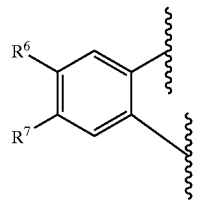

wherein $R^6$ and $R^7$ are independently selected from the group consisting of H, halogen, $CF_3$, $CF_3O$, $(C_1-C_4)$alkyl, $(C_2-C_4)$alkenyl, $(C_2-C_4)$alkynyl, $(C_1-C_4)$heteroalkyl, $(C_3-C_{10})$cycloheteroalkyl-alkyl and cyano; and B is a five-membered aromatic ring system containing at least one nitrogen atom.

18. A compound of claim 17, wherein Y is S.

19. A compound of claim 17, wherein Z is $NR^2R^3$.

20. A compound of claim 17, wherein Z is $NH_2$.

21. A compound of claim 17, wherein $R^1$ is $(C_1-C_6)$alkyl, $(C_1-C_6)$heteroalkyl or $(C_3-C_{10})$cycloheteroalkyl-alkyl.

22. A compound of claim 17, wherein B is a five-membered aromatic ring system containing 1–2 nitrogen atoms and 0–1 sulfur atoms.

23. A compound of claim 22, wherein B is unsubstituted or substituted by $(C_1-C_3)$alkyl, $CF_3$, cyano, or halogen.

24. A compound of claim 17, wherein Z is $NH_2$; $R^6$ is selected from the group consisting of H, halogen, $CF_3$, $CF_3O$, $(C_1-C_4)$alkyl, $(C_2-C_4)$alkenyl, $(C_1-C_4)$heteroalkyl, $(C_3-C_{10})$cycloheteroalkyl-alkyl and cyano, wherein the alkyl, alkenyl and heteroalkyl groups optionally bear additional substituents selected from cyano, carboxamido, $(C_1-C_3)$alkylsulfonyl or $(C_1-C_3)$alkoxy; and $R^7$ is selected from the group consisting of H, halogen, $CF_3$, $CF_3O$, $(C_1-C_4)$alkyl, $(C_2-C_4)$alkenyl, $(C_2-C_4)$alkynyl, $(C_1-C_4)$heteroalkyl and cyano.

25. A compound of claim 24, wherein $R^6$ is selected from the group consisting of $CH_2(CH_2)[[_m]]_nCN$, $CH_2(CH_2)_n SO_2CH_3$ and $CH_2(CH_2)_nOCH_3$, wherein the subscript n is an integer from 0 to 2.

26. A compound of claim 24 wherein $R^7$ is selected from the group consisting of H, halogen, $CF_3$ and $(C_1-C_4)$alkyl.

27. A compound of claim 24, wherein $R^7$ is methyl.

28. A compound of claim 1, having the formula:

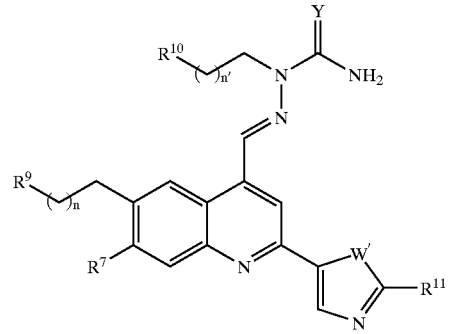

wherein Y is O, S or N—CN; W' is $N(CH_3)$, $N(CF_3)$, $N(CH_2CH_3)$, O or S; the subscripts n and n' are independently integers from 0 to 3; $R^7$ is H, halogen, $CF_3$, $CF_3O$, $(C_1-C_4)$alkyl, $(C_2-C_4)$alkenyl, $(C_2-C_4)$alkynyl, $(C_1-C_4)$heteroalkyl or cyano; $R^9$ is CN, $CONH_2$, CO—NH—$(C_1-C_6)$alkyl, CO—N[$(C_1-C_6)$alkyl]$_2$, CO—NH—$(C_1-C_6)$heteroalkyl, CO—N[$(C_1-C_6)$heteroalkyl]$_2$, $S(O)_{n''}$—$(C_1-C_6)$alkyl, $S(O)_{n''}$—$(C_1-C_6)$heteroalkyl, heteroaryl, $(C_1-C_6)$alkoxy or $(C_3-C_6)$cycloheteroalkyl, wherein each n" is independently an integer of 0 to 2; $R^{10}$ is $NH_2$, NH—$(C_1-C_6)$alkyl, N[$(C_1-C_6)$alkyl]$_2$, NH—$(C_1-C_6)$heteroalkyl, N[$(C_1-C_6)$heteroalkyl]$_2$, $(C_1-C_6)$heteroalkyl, $S(O)_{n''}$—$(C_1-C_6)$alkyl, $S(O)_{n''}$—$(C_1-C_6)$heteroalkyl, aryl, heteroaryl, O—$(C_1-C_6)$alkyl, O—$(C_1-C_6)$heteroalkyl or $(C_3-C_8)$cycloheteroalkyl; and $R^{11}$ is H, $CF_3$, $NH_2$, NH—$(C_1-C_6)$alkyl, N[$(C_1-C_6)$alkyl]$_2$, halogen or $(C_1-C_3)$alkyl.

29. A compound of claim 28, wherein Y is O or S; W' is N—$CH_3$; n is 2; n' is 1–3; $R^9$ is cyano, $CONH_2$, $SO_2$—$(C_1-C_6)$alkyl, $(C_1-C_6)$alkoxy or $(C_3-C_6)$cycloheteroalkyl; $R^{10}$ is NH—$(C_1-C_6)$alkyl, N[$(C_1-C_6)$alkyl]$_2$, NH—$(C_1-C_6)$heteroalkyl, N[$(C_1-C_6)$heteroalkyl]$_2$, O—$(C_1-C_6)$alkyl, O—$(C_1-C_6)$heteroalkyl, $(C_1-C_6)$alkoxy or $(C_3-C_8)$cycloheteroalkyl; and $R^{11}$ is H.

30. A compound of claim 17, wherein B contains a nitrogen atom at a position two atoms away from the atom attaching B to the remainder of the molecule.

31. A compound of claim 17, wherein B contains a nitrogen atom at the point of attachment of B to the remainder of the molecule.

32. A compound of claim 17, wherein B is selected from the group consisting of substituted or unsubstituted imidazolyl, substituted or unsubstituted thiazolyl and substituted or unsubstituted triazolyl.

33. A compound of claim 17, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

34. A compound of claim 1, wherein Y is S; Z is $NH_2$ and $R^1$ is $(C_1-C_6)$alkyl.

35. A compound of claim 34 wherein $R^1$ is methyl.

36. A compound of claim 1, wherein said compound is selected from the group consisting of:

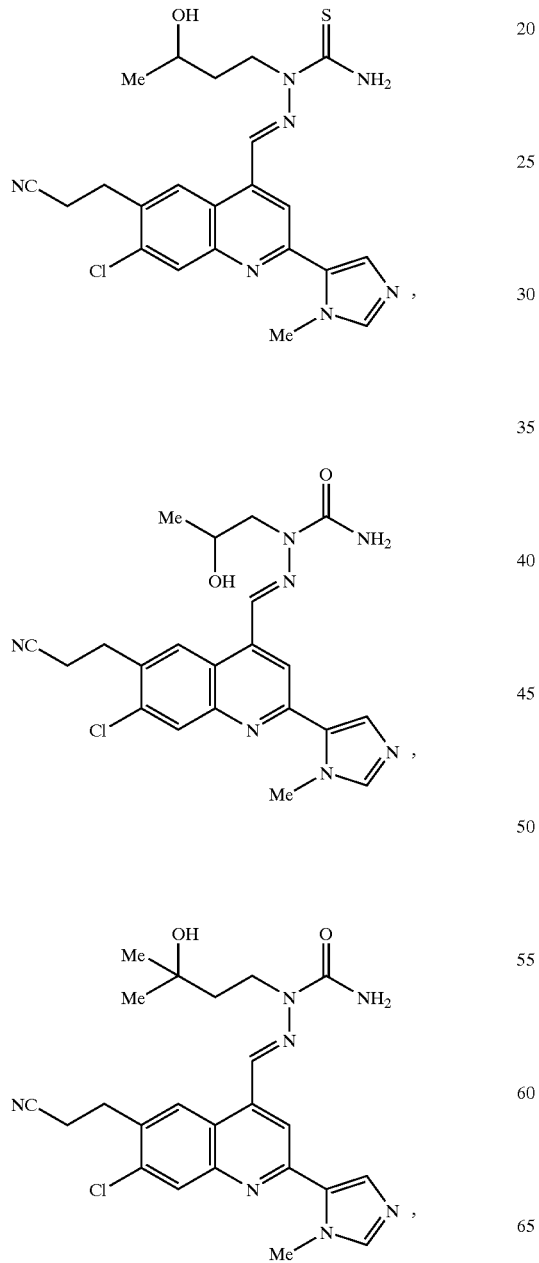

-continued

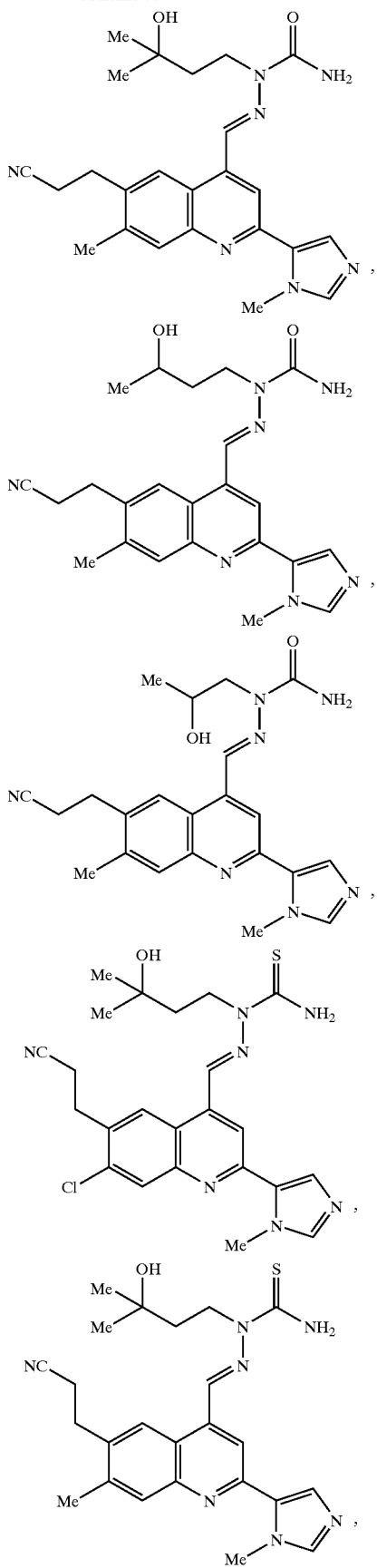

95
-continued
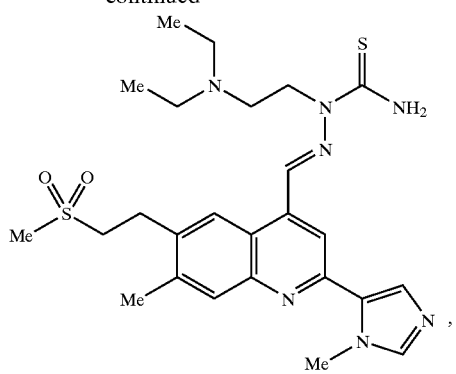
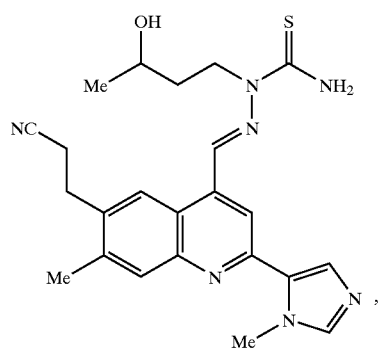
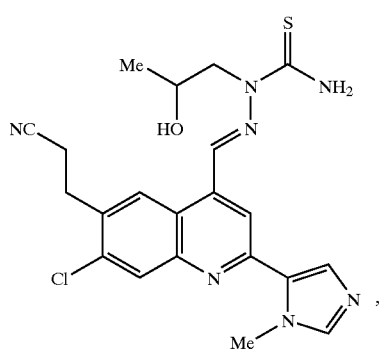
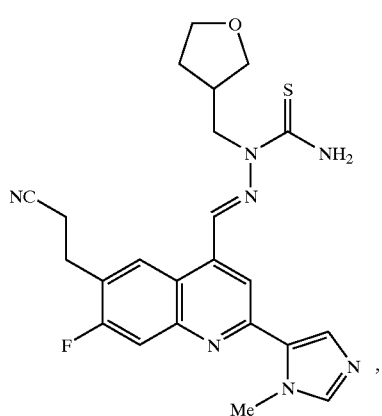
96
-continued
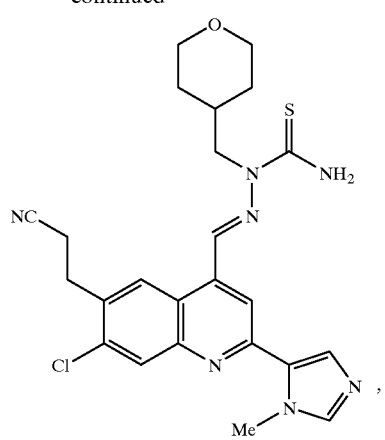
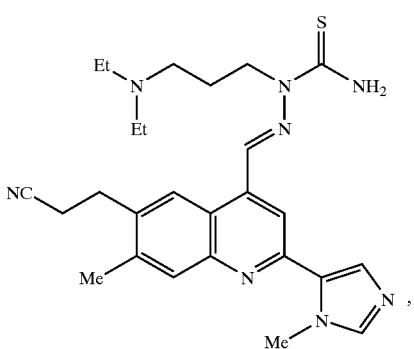
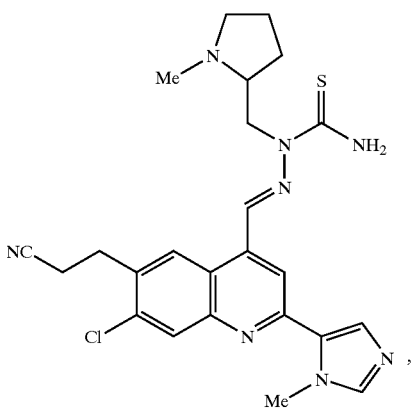
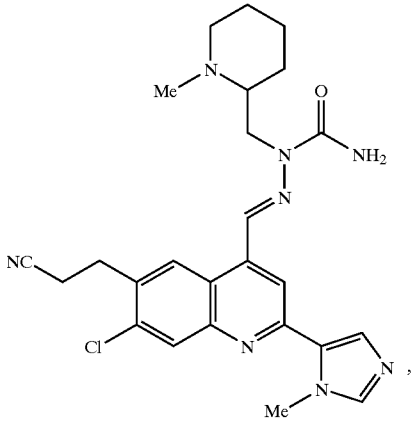

-continued

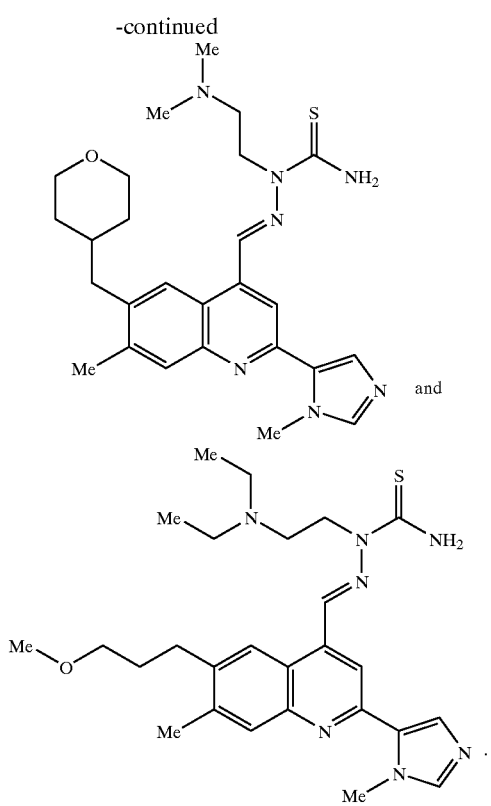

and

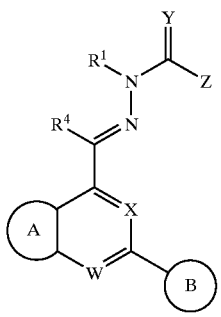

37. A composition comprising a pharmaceutically acceptable excipient and a compound having the formula:

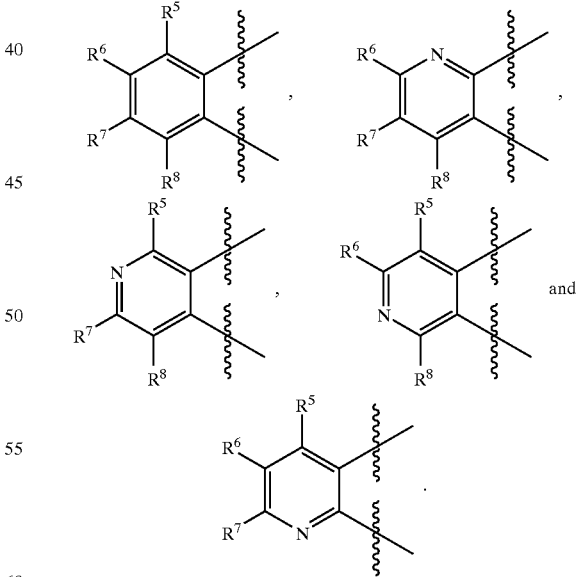

wherein
W is N;
X is CH;
Y is selected from the group consisting of O, S and N(R);
wherein R is selected from the group consisting of H, CN, $NO_2$, $(C_1-C_{10})$alkyl, $(C_3-C_{10})$cycloalkyl, $(C_4-C_{10})$ cycloalkyl-alkyl, $(C_3-C_{10})$alkenyl and $(C_2-C_{10})$ alkynyl;
Z is selected from the group consisting of H, $(C_1-C_{10})$ alkyl, $(C_3-C_{10})$cycloalkyl, $(C_4-C_{10})$cycloalkyl-alkyl, $(C_2-C_{10})$alkenyl, $(C_2-C_{10})$alkynyl and $NR^2R^3$;
$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_2-C_{10})$heteroalkyl, $(C_3-C_{10})$ cycloalkyl, $(C_4-C_{10})$cycloalkyl-alkyl, $(C_3-C_{10})$ cycloheteroalkyl-alkyl, $(C_3-C_{10})$cycloheteroalkyl, aryl, aryl$(C_1-C_4)$alkyl, aryl$(C_2-C_4)$heteroalkyl, heteroaryl$(C_2-C_4)$alkyl, heteroaryl$(C_2-C_4)$heteroalkyl and perfluoro$(C_1-C_6)$alkyl; and wherein when Z is $NR^2R^3$, $R^2$ and $R^3$ can be combined to form a 5- to 7-membered ring; and wherein when Y is N(R), R and $R^1$ are optionally combined to form a 5- to 7-membered ring;
$R^4$ is selected from the group consisting of H, $(C_1-C_6)$ alkyl, $(C_3-C_6)$cycloalkyl, $(C_4-C_7)$cycloalkyl-alkyl, $(C_2-C_6)$alkenyl and $(C_2-C_6)$alkynyl;
A is a substituted or unsubstituted 6-membered fused carbocyclic or heterocyclic aromatic ring system, wherein the heterocyclic aromatic ring system contains 1–2 N atoms; and
B is a substituted or unsubstituted five- or six-membered ring which is aromatic, containing at least one nitrogen atom, and from 0 to 3 additional heteroatoms, wherein the B ring substituents are selected from the group consisting of halogen, $CF_3$, $CF_3O$, $(C_1-C_6)$alkyl, perfluoro$(C_1-C_6)$alkyl, $(C_2-C_6)$alkenyl, $(C_2-C_6)$ alkynyl, $(C_1-C_6)$heteroalkyl, $(C_1-C_6)$alkoxy, $(C_1-C_6)$ thioalkoxy, amino, $(C_1-C_6)$alkylamino, di$(C_1-C_6)$ alkylamino, $(C_3-C_{10})$cycloalkyl, $(C_4-C_{10})$cycloalkyl-alkyl, $(C_3-C_{10})$cycloheteroalkyl, cyano, nitro, sulfonamido, $(C_1-C_6)$acyl, $(C_1-C_6)$acylamino, $(C_2-C_6)$alkoxycarbonyl, $(C_2-C_6)$alkoxycarbonyl $(C_1-C_6)$alkyl, carboxamido and $(C_1-C_6)$heteroalkoxyl;
or pharmaceutically acceptable salts thereof.

38. A composition in accordance with claim 37, wherein Y is selected from the group consisting of O and S.

39. A composition in accordance 37, wherein Y is O.

40. A composition in accordance claim 37, wherein Y is S.

41. A composition in accordance claim 37, wherein Z is $NR^2R^3$.

42. A composition in accordance claim 38, wherein $R^4$ is H.

43. A composition in accordance with claim 37, wherein A is selected from the group consisting of:

wherein
$R^5$, $R^6$, $R^7$ and $R^8$ are independently selected from the group consisting of H, halogen, $CF_3$, $(C_1-C_6)$alkyl, $(C_2-C_6)$alkenyl, $(C_2-C_6)$alkynyl, $(C_1-C_6)$heteroalkyl, $(C_1-C_6)$alkoxy, $(C_1-C_6)$thioalkoxy, amino, $(C_1-C_6)$ alkylamino, di$(C_1-C_6)$alkylamino, $(C_3-C_{10})$ cycloalkyl, $(C_4-C_{10})$cycloalkyl-alkyl, $(C_3-C_{10})$ cycloheteroalkyl, $(C_3-C_{10})$cycloheteroalkyl-alkyl, cyano, nitro, $(C_1-C_6)$acyl, $(C_1-C_6)$acylamino, $(C_2-C_6)$ alkoxycarbonyl, $(C_3-C_6)$alkoxycarbonylalkyl, $CONH_2$, $CO-NH-(C_1-C_6)$alkyl, $CO-N[(C_1-C_6)$ alkyl$]_2$, $SO_2NH_2$, $SO_2NH-(C_1-C_6)$alkyl, $SO_2N-[(C_1-C_6)$alkyl$]_2$ and $(C_1-C_6)$heteroalkoxy; or two adjacent R groups can be linked together to form a new 5- or 6-membered carbocyclic or heterocyclic ring.

44. A composition in accordance with claim 37, wherein Y is O or S; and A is selected from the group consisting of:

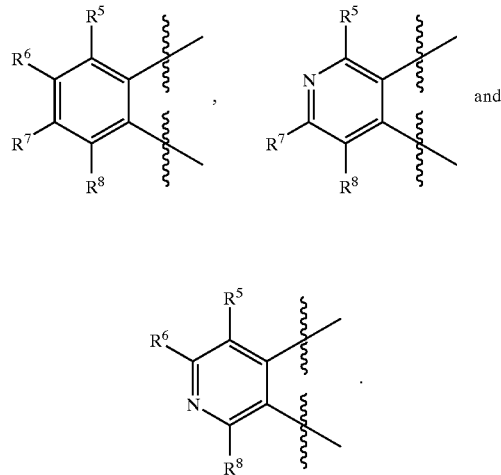

45. A composition in accordance with claim 37, wherein B contains a nitrogen atom at a position two atoms away from the atom attaching B to the remainder of the molecule.

46. A composition in accordance with claim 37, wherein B contains a nitrogen atom at the point of attachment of B to the remainder of the molecule.

47. A composition in accordance with claim 37, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

48. A composition in accordance with claim 37, wherein B is selected from the group consisting of substituted or unsubstituted imidazolyl, substituted or unsubstituted thiazolyl and substituted or unsubstituted triazolyl.

49. A composition in accordance with claim 44, wherein B contains a nitrogen atom at a position two atoms away from the atom attaching B to the remainder of the molecule.

50. A composition in accordance with claim 44, wherein B contains a nitrogen atom at the point of attachment of B to the remainder of the molecule.

51. A composition in accordance with claim 44, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

52. A composition in accordance with claim 44, wherein B is selected from the group consisting of substituted or unsubstituted imidazolyl, substituted or unsubstituted thiazolyl and substituted or unsubstituted triazolyl.

53. A method for treating rheumatoid arthritis said method comprising administering to a subject in need of such treatment, an effective amount of a compound having the formula:

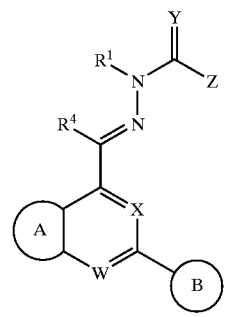

wherein
W is N;
X is CH;
Y is selected from the group consisting of O, S and N(R);
    wherein R is selected from the group consisting of H, CN, $NO_2$, $(C_1-C_{10})$alkyl, $(C_3-C_{10})$cycloalkyl, $(C_4-C_{10})$cycloalkyl-alkyl, $(C_3-C_{10})$alkenyl and $(C_2-C_{10})$alkynyl;
Z is selected from the group consisting of H, $(C_1-C_{10})$ alkyl, $(C_3-C_{10})$cycloalkyl, $(C_4-C_{10})$cycloalkyl-alkyl, $(C_2-C_{10})$alkenyl, $(C_2-C_{10})$alkynyl and $NR^2R^3$;
$R^1$, $R^2$ and $R^3$ are independently selected from the group consisting of H, $(C_1-C_{10})$alkyl, $(C_3-C_{10})$alkenyl, $(C_2-C_{10})$alkynyl, $(C_2-C_{10})$heteroalkyl, $(C_3-C_{10})$ cycloalkyl, $(C_4-C_{10})$cycloalkyl-alkyl, $(C_3-C_{10})$ cycloheteroalkyl-alkyl, $(C_3-C_{10})$cycloheteroalkyl, aryl, aryl$(C_1-C_4)$alkyl, aryl$(C_2-C_4)$heteroalkyl, heteroaryl$(C_2-C_4)$alkyl, heteroaryl$(C_2-C_4)$heteroalkyl and perfluoro$(C_1-C_6)$alkyl; and wherein when Z is $NR^2R^3$, $R^2$ and $R^3$ can be combined to form a 5- to 7-membered ring; and wherein when Y is N(R), R and $R^1$ are optionally combined to form a 5- to 7-membered ring;
$R^4$ is selected from the group consisting of H, $(C_1-C_6)$ alkyl, $(C_3-C_6)$cycloalkyl, $(C_4-C_7)$cycloalkyl-alkyl, $(C_2-C_6)$alkenyl and $(C_2-C_6)$alkynyl;
A is a substituted or unsubstituted 6-membered fused carbocyclic or heterocyclic aromatic ring system, wherein the heterocyclic aromatic ring system contains 1–2 N atoms; and
B is a substituted or unsubstituted five- or six-membered ring which is aromatic, containing at least one nitrogen atom, and from 0 to 3 additional heteroatoms, wherein the B ring substituents are selected from the group consisting of halogen, $CF_3$, $CF_3O$, $(C_1-C_6)$alkyl, perfluoro$(C_1-C_6)$alkyl, $(C_2-C_6)$alkenyl, $(C_2-C_6)$ alkynyl, $(C_1-C_6)$heteroalkyl, $(C_1-C_6)$alkoxy, $(C_1-C_6)$ thioalkoxy, amino, $(C_1-C_6)$alkylamino, di$(C_1-C_6)$alkyl amino, $(C_3-C_{10})$cycloalkyl, $(C_4-C_{10})$cycloalkyl-alkyl, $(C_3-C_{10})$cycloheteroalkyl, cyano, nitro, sulfonamido, $(C_1-C_6)$acyl, $(C_1-C_6)$acylamino, $(C_2-C_6)$ alkoxycarbonyl, $(C_2-C_6)$alkoxycarbonyl$(C_1-C_6)$alkyl, carboxamido and $(C_1-C_6)$heteroalkoxy;
or pharmaceutically acceptable salts thereof.

54. A method in accordance with claim 53 wherein Y is selected from the group consisting of O and S.

55. A method in accordance with claim 53, wherein Y is O.

56. A method in accordance with claim 53 wherein Y is S.

57. A method in accordance with claim 53 wherein Z is $NR^2R^3$.

58. A method in accordance with claim 54, wherein R⁴ is H.

59. A method in accordance with claim 53, wherein A is selected from the group consisting of:

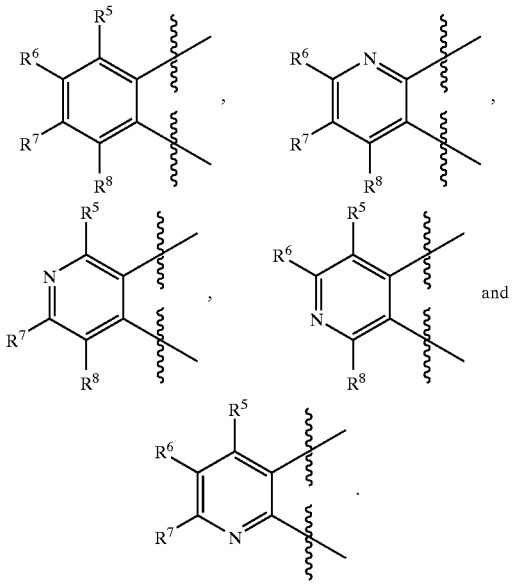

wherein

R⁵, R⁶, R⁷ and R⁸ are independently selected from the group consisting of H, halogen, CF₃, (C₁–C₆)alkyl, (C₂–C₆)alkenyl, (C₂–C₆)alkynyl, (C₁–C₆)heteroalkyl, (C₁–C₆)alkoxy, (C₁–C₆)thioalkoxy, amino, (C₁–C₆) alkylamino, di(C₁–C₆)alkylamino, (C₃–C₁₀) cycloalkyl, (C₄–C₁₀)cycloalkyl-alkyl, (C₃–C₁₀) cycloheteroalkyl, (C₃–C₁₀)cycloheteroalkyl-alkyl, cyano, nitro, (C₁–C₆)acyl, (C₁–C₆)acylamino, (C₂–C₆) alkoxycarbonyl, (C₃–C₆)alkoxycarbonylalkyl, CONH₂, CO—NH—(C₁–C₆)alkyl, CO—N[(C₁–C₆) alkyl]₂, SO₂NH₂, SO₂NH—(C₁–C₆)alkyl, SO₂N—[(C₁–C₆)alkyl]₂ and (C₁–C₆)heteroalkoxy; or two adjacent R groups can be linked together to form a new 5- or 6-membered carbocyclic or heterocyclic ring.

60. A method in accordance with claim 53, wherein Y is O or S; and A is selected from the group consisting of:

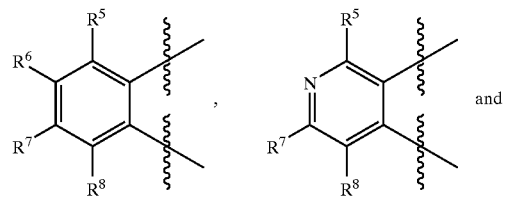

-continued

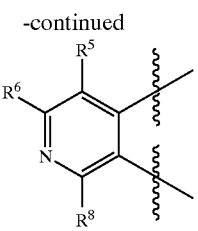

61. A method in accordance with claim 53, wherein B contains a nitrogen atom at a position two atoms away from the atom attaching B to the remainder of the molecule.

62. A method in accordance with claim 53, wherein B contains a nitrogen atom at the point of attachment of B to the remainder of the molecule.

63. A method in accordance with claim 53, wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

64. A method in accordance with claim 53, wherein B is selected from the group consisting of substituted or unsubstituted imidazolyl, substituted or unsubstituted thiazolyl and substituted or unsubstituted triazolyl.

65. A method in accordance with claim 60, wherein B contains a nitrogen atom at a position two atoms away from the atom attaching B to the remainder of the molecule.

66. A method in accordance with claim 60, wherein B contains a nitrogen atom at the point of attachment of B to the remainder of the molecule.

67. A method in accordance with claim 60 wherein B is selected from the group consisting of 1-methylimidazol-5-yl, 1-(trifluoromethyl)imidazol-5-yl, 5-methylimidazol-1-yl, 5-(trifluoromethyl)imidazol-1-yl, thiazol-5-yl, imidazol-1-yl, 1-methyl-1,3,4-triazolyl, and 4-methyl-1,2,4-triazol-3-yl.

68. A method in accordance with claim 60, wherein B is selected from the group consisting of substituted or unsubstituted imidazolyl, substituted or unsubstituted thiazolyl and substituted or unsubstituted triazolyl.

69. A method in accordance with claim 53, wherein said compound is administered orally.

70. A method in accordance with claim 53, wherein said compound is administered topically.

71. A method in accordance with claim 53, wherein said compound is administered intravenously or intramuscularly.

72. A method in accordance with claim 53, wherein said compound is administered in combination with a second therapeutic agent, said second therapeutic agent being a member selected from the group consisting of prednisone, dexamethasone, beclomethasone, methylprednisone, betamethasone, hydrocortisone, methotrexate, cyclosporin, rapamycin, tacrolimus, antihistamine drugs, TNF antibodies, IL-1 antibodies, soluble TNF receptors, soluble IL-1 receptors, TNF or IL-1 receptor antagonists, non-steroidal antiinflammatory agents, COX-2 inhibitors.

73. A method in accordance with claim 72, wherein said administering is seqential.

* * * * *

UNITED STATES PATENT AND TRADEMARK OFFICE
CERTIFICATE OF CORRECTION

PATENT NO. : 6,846,834 B2
DATED : January 25, 2005
INVENTOR(S) : Browner et al.

It is certified that error appears in the above-identified patent and that said Letters Patent is hereby corrected as shown below:

Title page,
Item [73], Assignee, please replace "So. San Francisco, CA" with -- Thousand Oaks, CA --.

Column 90,
Line 3, please replace "$(C_{1-6})$heteroalkoxyl" with -- $(C_{1-6})$heteroalkoxy --.
Line 4, please replace "salts" with -- salt --.

Column 98,
Line 24, please replace "$(C_{1-6})$heteroalkoxyl" with -- $(C_{1-6})$heteroalkoxy --.
Line 25, please replace "salts" with -- salt --.

Column 100,
Line 60, please replace "salts" with -- salt --.

Signed and Sealed this

Thirteenth Day of September, 2005

JON W. DUDAS
*Director of the United States Patent and Trademark Office*